(12) United States Patent
Fyfe

(10) Patent No.: US 9,771,353 B2
(45) Date of Patent: Sep. 26, 2017

(54) KINASE INHIBITORS BASED UPON N-ALKYL PYRAZOLES

(71) Applicants: RESPIVERT LIMITED, High Wycombe, Buckinghamshire (GB); TOPIVERT PHARMA LIMITED, London (GB)

(72) Inventor: Matthew Colin Thor Fyfe, London (GB)

(73) Assignees: TOPIVERT PHARMA LIMITED, London (GB); RESPIVERT LIMITED, High Wycombe, Buckinghamshire (GB)

(*) Notice: Subject to any disclaimer, the term of this patent is extended or adjusted under 35 U.S.C. 154(b) by 0 days.

(21) Appl. No.: 14/781,844

(22) PCT Filed: Apr. 1, 2014

(86) PCT No.: PCT/GB2014/051017
§ 371 (c)(1),
(2) Date: Oct. 1, 2015

(87) PCT Pub. No.: WO2014/162121
PCT Pub. Date: Oct. 9, 2014

(65) Prior Publication Data
US 2016/0039797 A1  Feb. 11, 2016

(30) Foreign Application Priority Data

Apr. 2, 2013 (GB) .................... 1305946.4
Dec. 20, 2013 (GB) .................... 1322681.6

(51) Int. Cl.
| C07D 403/12 | (2006.01) |
| C07D 401/12 | (2006.01) |
| C07D 403/14 | (2006.01) |
| A61K 31/4439 | (2006.01) |
| A61K 31/506 | (2006.01) |
| A61K 31/5377 | (2006.01) |

(52) U.S. Cl.
CPC ........ *C07D 403/12* (2013.01); *A61K 31/4439* (2013.01); *A61K 31/506* (2013.01); *A61K 31/5377* (2013.01); *C07D 401/12* (2013.01); *C07D 403/14* (2013.01)

(58) Field of Classification Search
CPC .. C07D 401/12; C07D 401/14; C07D 403/12; C07D 403/14; A61K 31/506
See application file for complete search history.

(56) References Cited

U.S. PATENT DOCUMENTS

| 6,319,921 B1 | 11/2001 | Cirillo et al. |
| 6,492,393 B1 | 12/2002 | Breitfelder et al. |
| 6,492,529 B1 | 12/2002 | Kapadia et al. |
| 6,525,046 B1 | 2/2003 | Cirillo et al. |
| 6,852,717 B2 | 2/2005 | Cirillo et al. |
| 6,894,173 B2 | 5/2005 | Zhang et al. |
| 6,916,814 B2 | 7/2005 | Moss et al. |
| 7,041,669 B2 | 5/2006 | Cirillo et al. |
| 7,241,758 B2 | 7/2007 | Sun et al. |
| 7,750,160 B2 | 7/2010 | Milanov et al. |
| 7,767,670 B2 | 8/2010 | Mehta et al. |
| 7,838,541 B2 | 11/2010 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |

(Continued)

FOREIGN PATENT DOCUMENTS

| WO | WO 99/23091 | 5/1999 |
| WO | WO 00/43384 | 7/2000 |
| WO | WO 00/55139 | 9/2000 |
| WO | WO 01/04115 | 1/2001 |
| WO | WO 01/36403 | 5/2001 |

(Continued)

OTHER PUBLICATIONS

Kinase Inhibitors, Methods in Molecular Biology 795 (B. Kuster ed., 2012).*
R. Singh et al., 42 Annual Reports in Medicinal Chemistry, 379-391 (2007).*
M.E. Weinblatt et al., 363 The New England Journal of Medicine 1303-1312 (2010).*

(Continued)

*Primary Examiner* — Alexander R Pagano
(74) *Attorney, Agent, or Firm* — Knobbe, Martens, Olson & Bear, LLP

(57) ABSTRACT

Compounds are of formula (I):

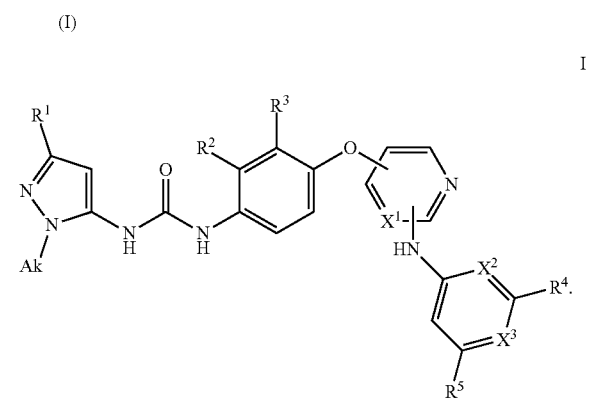

The compounds have antiinflammatory activity (e.g., through inhibition of one or more of members of: the family of p38 mitogen-activated protein kinase enzymes; Syk kinase; and members of the Src family of tyrosine kinases) and have use in therapy, including in pharmaceutical combinations, especially in the treatment of inflammatory diseases, including inflammatory diseases of the lung, eye and intestines.

19 Claims, No Drawings

(56) References Cited

U.S. PATENT DOCUMENTS

| | | | |
|---|---|---|---|
| 8,299,074 B2 | 10/2012 | Ito et al. | |
| 8,618,140 B2 | 12/2013 | Ito et al. | |
| 8,642,773 B2 | 2/2014 | Ito et al. | |
| 8,927,563 B2 | 1/2015 | Fyfe | |
| 8,933,228 B2 | 1/2015 | Murray et al. | |
| 8,975,285 B2 | 3/2015 | Ito et al. | |
| 9,024,041 B2 | 5/2015 | King-Underwood | |
| 9,079,893 B2 | 7/2015 | Cass | |
| 9,108,950 B2* | 8/2015 | Ito | C07D 491/10 |
| 9,249,125 B2 | 2/2016 | Duffy et al. | |
| 9,447,076 B2 | 9/2016 | Longshaw et al. | |
| 9,481,648 B2 | 11/2016 | Baker et al. | |
| 9,624,196 B2 | 4/2017 | Longshaw et al. | |
| 9,701,670 B2 | 7/2017 | Cariou et al. | |
| 2003/0125354 A1 | 7/2003 | Hao et al. | |
| 2003/0130309 A1 | 7/2003 | Moss et al. | |
| 2003/0232865 A1 | 12/2003 | Cirillo et al. | |
| 2004/0152725 A1 | 8/2004 | Moss et al. | |
| 2005/0148605 A1 | 7/2005 | Grotzfeld et al. | |
| 2005/0165024 A1 | 7/2005 | Milanov et al. | |
| 2005/0165031 A1 | 7/2005 | Grotzfeld et al. | |
| 2005/0165074 A1 | 7/2005 | Grotzfeld et al. | |
| 2005/0171171 A1 | 8/2005 | Mehta et al. | |
| 2005/0171172 A1 | 8/2005 | Lai et al. | |
| 2005/0192314 A1 | 9/2005 | Mehta et al. | |
| 2005/0197371 A1 | 9/2005 | Milanov et al. | |
| 2005/0261315 A1 | 11/2005 | Mehta et al. | |
| 2005/0267182 A1 | 12/2005 | Milanov et al. | |
| 2010/0173917 A1 | 7/2010 | Grotzfeld et al. | |
| 2011/0118245 A1 | 5/2011 | Abraham et al. | |
| 2012/0244120 A1 | 9/2012 | Charron et al. | |
| 2013/0029990 A1 | 1/2013 | King-Underwood et al. | |
| 2013/0040962 A1 | 2/2013 | King-Underwood et al. | |
| 2013/0040995 A1 | 2/2013 | King-Underwood et al. | |
| 2013/0102607 A1 | 4/2013 | Cass et al. | |
| 2013/0123260 A1 | 5/2013 | Charron et al. | |
| 2013/0150343 A1 | 6/2013 | Van Niel et al. | |
| 2013/0156826 A1 | 6/2013 | Murray et al. | |
| 2014/0057915 A1* | 2/2014 | Cariou | A61K 31/506 514/236.5 |
| 2014/0114064 A1 | 4/2014 | Ito et al. | |
| 2014/0228410 A1 | 8/2014 | Ito et al. | |
| 2014/0249169 A1 | 9/2014 | Ito et al. | |
| 2014/0296208 A1* | 10/2014 | Baker | A61K 31/5377 514/211.15 |
| 2014/0296271 A1 | 10/2014 | Fyfe | |
| 2015/0166483 A1 | 6/2015 | Fyfe | |
| 2015/0203475 A1 | 7/2015 | Duffy et al. | |
| 2015/0210722 A1* | 7/2015 | Fyfe | C07F 9/65583 514/63 |
| 2015/0218137 A1 | 8/2015 | Cariou et al. | |
| 2015/0225373 A1* | 8/2015 | Fyfe | C07D 403/12 514/236.5 |
| 2015/0225427 A1* | 8/2015 | Fyfe | A61K 31/695 514/63 |
| 2015/0232450 A1 | 8/2015 | Longshaw et al. | |
| 2015/0252024 A1 | 9/2015 | Ito et al. | |
| 2015/0329523 A1* | 11/2015 | Frickel | C07D 401/14 514/235.2 |
| 2016/0009695 A1 | 1/2016 | Ito et al. | |
| 2016/0016934 A1* | 1/2016 | Fyfe | C07D 403/12 514/272 |
| 2016/0096805 A1* | 4/2016 | Fyfe | A61K 31/4412 514/349 |
| 2016/0102059 A1 | 4/2016 | Baker et al. | |
| 2016/0318909 A1 | 11/2016 | Fyfe | |
| 2016/0318958 A1 | 11/2016 | Fyfe et al. | |
| 2016/0340343 A1 | 11/2016 | Fyfe et al. | |
| 2016/0340375 A1 | 11/2016 | Fyfe et al. | |
| 2016/0368896 A1 | 12/2016 | Longshaw et al. | |
| 2016/0376232 A1 | 12/2016 | Thom | |
| 2017/0057945 A1 | 3/2017 | Longshaw et al. | |

FOREIGN PATENT DOCUMENTS

| | | |
|---|---|---|
| WO | WO 02/092576 | 11/2002 |
| WO | WO 03/005999 | 1/2003 |
| WO | WO 03/068228 | 8/2003 |
| WO | WO 03/072569 | 9/2003 |
| WO | WO 03/072569 A1 | 9/2003 |
| WO | WO 2004/113352 | 12/2004 |
| WO | WO 2005/018624 | 3/2005 |
| WO | WO 2005/048948 | 6/2005 |
| WO | WO 2007/053394 | 5/2007 |
| WO | WO 2010/038085 | 4/2010 |
| WO | WO 2010/038086 | 4/2010 |
| WO | WO 2010/067130 | 6/2010 |
| WO | WO 2010/067131 | 6/2010 |
| WO | WO 2010/112936 | 10/2010 |
| WO | WO 2011/070368 | 6/2011 |
| WO | WO 2011/070369 | 6/2011 |
| WO | WO 2011/121366 | 10/2011 |
| WO | WO 2011/124923 | 10/2011 |
| WO | WO 2011/124924 | 10/2011 |
| WO | WO 2011/158039 | 12/2011 |
| WO | WO 2011/158042 | 12/2011 |
| WO | WO 2011/158044 | 12/2011 |
| WO | WO 2013/050756 | 4/2013 |
| WO | WO 2013/050757 | 4/2013 |
| WO | WO 2013/083604 A1 | 6/2013 |
| WO | WO 2014/027209 | 2/2014 |
| WO | WO 2014/027209 A1 | 2/2014 |
| WO | WO 2014/033446 | 3/2014 |
| WO | WO 2014/033447 | 3/2014 |
| WO | WO 2014/033448 | 3/2014 |
| WO | WO 2014/033449 | 3/2014 |
| WO | WO 2014/076484 | 5/2014 |
| WO | WO 2014/140582 | 9/2014 |
| WO | WO 2014/162122 | 10/2014 |
| WO | WO 2014/162126 | 10/2014 |
| WO | WO 2015/121444 | 8/2015 |
| WO | WO 2015/121660 | 8/2015 |

OTHER PUBLICATIONS

N. Yamamoto et al., 306 The Journal of Pharmacology and Experimental Therapeutics, 1174-1181 (2003).*
E.S. Masuda et al., 21 Pulmonary Pharmacology & Therapeutics, 461-467 (2008).*
D. Singh et al., 50 The Journal of Clinical Pharmacology, 94-100 (2010).*
A.C. Brando et al., 63 Pharmacological Reports, 1029-1039 (2011).*
R.S. Jope et al., 32 Neurochemical Research, 577-595 (2007).*
P. Kim et al., 335 Cell and Tissue Research, 249-259 (2009).*
U. McDermott et al., 27 Journal of Clinical Oncology, 5650-5659 (2009).*
C.L. Sawyers, Nature, 548-552 (2008).*
C.M. Coughlin et al., Breast Cancer Research Treatment, 1-11 (2010).*
G. Liu et al., 31 Arteriosclerosis, Thrombosis and Vascular Biology, 1342-1350 (2011).*
E. R. Sutherland et al., 350 The New England Journal of Medicine, 2689-2697 (2004).*
S. Judge et al., 111 Pharmacology & Therapeutics, 224-259 (2006).*
V. Brinkmann et al., 9 Nature Reviews | Drug Discovery, 883-897 (2010).*
Dumas, J. 2002 "Protein kinase inhibitors from the urea class" *Current Opinion in Drug Discovery & Development* 5(5): 718-727.
U.S. Appl. No. 14/561,290, filed Dec. 5, 2014, Murray.
U.S. Appl. No. 14/872,527, filed Oct. 1, 2015, Baker, et al.
U.S. Appl. No. 14/872,807, filed Oct. 1, 2015, Fyfe.
U.S. Appl. No. 14/883,464, filed Oct. 14, 2015, Catherine Elisabeth Charron.
U.S. Appl. No. 14/924,541, filed Jan. 4, 2016, Catherine Elisabeth Charron.

(56) References Cited

OTHER PUBLICATIONS

U.S. Appl. No. 14/988,824, filed Jan. 6, 2016, John King-Underwood.
Barnes, et al. 2007 "Trimethylsilylpyrazoles as novel inhibitors of p38 MAP kinase: A new use of silicon bioisosteres in medicinal chemistry" *Bioorganic & Medicinal Chemistry* 17; 354-357.
CAS Registry No. 1379397-83-7, 2012 American Chemical Society.
CAS Registry No. 1384608-34-7, 2012 American Chemical Society.
Dumas; et al. 2004 "Recent developments in the discovery of protein kinase inhibitors from the urea class" *Current Opinion in Drug Discovery & Development* 7(5):600-616.
Dumas, et al. 2000 "1-Phenyl-5-pyrazolyl Ureas: Potent and Selective p38 Kinase Inhibitors" *Bioorganic & Medicinal Chemistry Letters* 10: 2051-2054.
Dumas, et al. 2002 "Synthesis and Pharmacological Characterization of a Potent, Orally Active p38 Kinase Inhibitor" *Bioorganic & Medicinal Chemistry Letters* 12: 1559-1562.
Dumas, et al. 2002 "Protein kinase inhibitors from the urea class" *Current Opinion in Drug Discovery & Development* 5(5): 718-727.
Kroe, et al. 2003 "Thermal Denaturation: A Method to Rank Slow Binding, High-Affinity P38α MAP Kinase Inhibitors" *Journal of Medicinal Chemistry* 46: 4669-4675.
Moss, et al. 2007 "New modifications to the area of pyrazole-naphthyl urea based p38 MAP kinase inhibitors that bind to the adenine/ATP site" *Bioorganic & Medicinal Chemistry Letters* 17: 4242-4247.
Pettus, et al. 2008 "Small molecule p38 MAP kinase inhibitors for the treatment of inflammatory diseases: Novel structures and developments during 2006-2008" *Current Topics in Medicinal Chemistry* 8(16):1452-1467.
Regan, et al. 2003 "The Kinetics of Binding to p38MAP Kinase by Analogues of BIRB 796" *Bioorganic & Medicinal Chemistry Letters* 13: 3101-3104.
Regan, et al. 2003 "Structure-Activity Relationships of the p38α MAP Kinase Inhibitor 1-(5-tert-Butyl-2-p-tolyl-2H-pyrazol-3-yl)-3-[4-(2-morpholin-4-yl-ethoxy)naphthalen-1-yl]urea (BIRB 796)" *Journal of Medicinal Chemistry* 46: 4676-4686.
Boehm, et al. 2000 "New inhibitors of p38 kinase" *Exp. Opin. Ther. Patents* 10(1): 25-37.
Dodeller, et al. 2006 "The p38 mitogen-activated protein kinase signaling cascade in CD4 T cells" *Arthritis Research & Therapy* 8(2): 1-11.
U.S. Appl. No. 15/457,810, filed Mar. 13, 2017, Lonshaw et al.

* cited by examiner

KINASE INHIBITORS BASED UPON N-ALKYL PYRAZOLES

This invention relates, inter alia, to compounds which are antiinflammatory agents (e.g. through inhibition of one or more of members of: the family of p38 mitogen-activated protein kinase enzymes (referred to herein as p38 MAP kinase inhibitors), for example the alpha kinase sub-type thereof; Syk kinase; and the Src family of tyrosine kinases). The invention also relates to the use of such compounds in therapy, including in mono- and combination therapies, especially in the treatment of inflammatory diseases, including inflammatory diseases of the lung (such as asthma and chronic obstructive pulmonary disease (COPD)), eye (such as uveitis) and gastrointestinal tract (such as Crohn's disease and ulcerative colitis).

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively) have been identified, each displaying different patterns of tissue expression. The p38 MAPK alpha and beta isoforms are found ubiquitously throughout the body; are present in many different cell types and are inhibited by a number of previously described small molecular weight compounds. Early classes of inhibitors were highly toxic due to the broad tissue distribution of these isoforms which resulted in off-target effects of the compounds. Some of the more recently identified inhibitors show improved selectivity for p38 MAPK alpha and beta isoforms and have wider safety margins.

p38 MAP kinase is believed to play a pivotal role in many of the signalling pathways that are involved in initiating and maintaining chronic, persistent inflammation in human disease, for example, in severe asthma, COPD and inflammatory bowel disease (IBD). There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith describes the inhibitory effect of p38 MAP kinase inhibitors on TNFα (but not IL-8) release from human PBMCs (Smith, S. J., *Br. J. Pharmacol.*, 2006, 149:393-404).

The use of inhibitors of p38 MAP kinase in the treatment of COPD and IBD has also been proposed. Small molecule inhibitors targeted to p38 MAPKα/β have proved to be effective in reducing various parameters of inflammation in:
- cells and tissues obtained from patients with COPD, who are generally corticosteroid insensitive (Smith, S. J., *Br. J. Pharmacol.*, 2006, 149:393-404);
- biopsies from IBD patients (Docena, G. et al., *J. of Trans. Immunol.*, 2010, 162:108-115); and
- in vivo animal models (Underwood, D. C. et al., *Am. J. Physiol.*, 2000, 279:L895-902; Nath, P. et al., *Eur. J. Pharmacol.*, 2006, 544:160-167).

Irusen and colleagues also suggested the possibility of involvement of p38 MAPKα/β on corticosteroid insensitivity via the reduction of binding affinity of the glucocorticoid receptor (GR) in nuclei (Irusen, E. et al., *J. Allergy Clin. Immunol.*, 2002, 109:649-657). Clinical investigations in inflammatory diseases with a range of p38 MAP kinase inhibitors, including AMG548, BIRB 796, VX702, SCIO469 and SCIO323, has been described (Lee, M. R. and Dominguez, C., *Current Med. Chem.*, 2005, 12:2979-2994.). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al. (2007; *American Thoracic Society Abstract A56*) demonstrates that silencing p38 MAPK γ has the potential to restore sensitivity to corticosteroids. Thus, there may be a dual benefit for patients in the use of a p38 MAP kinase inhibitor for the treatment of COPD.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

It has been disclosed previously that compounds that inhibit the activity of both the c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). Taken together with inhibition of p38 MAPK, these are particularly attractive properties for compounds to possess that are intended to treat patients with chronic respiratory diseases.

Certain p38 MAPK inhibitors have also been described as inhibitors of replication of respiratory syncytial virus (Cass L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. Due to the ubiquitous expression of p38 in inflammatory cells it has become an obvious target for investigation in IBD models. Studies investigating the efficacy of p38 inhibitors in animal models of IBD and human biopsies from IBD patients indicated that p38 could be a target for the treatment of IBD (Hove, T. ten et al., *Gut*, 2002, 50:507-512, Docena, G. et al., *J. of Trans. Immunol.*, 2010, 162:108-115). However, these findings are not completely consistent with other groups reporting no effect with p38 inhibitors (Malamut G. et al., *Dig. Dis. Sci,* 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology,* 2006, 4:325-334). A small clinical study investigating the efficacy of CNI-1493, a P38 and Jnk inhibitor, in patients with severe Crohn's disease showed significant improvement in clinical score over 8 weeks (Hommes, D. et al. *Gastroenterology.* 2002 122:7-14).

T cells are known to play key role in mediating inflammation of the gastrointestinal tract. Pioneering work by Powrie and colleagues demonstrated that transfer of naive CD4+ cells into severely compromised immunodeficient (SCID) animals results in the development of colitis which is dependent on the presence of commensal bacteria (Powrie F. et al. *Int Immunol.* 1993 5:1461-71). Furthermore, investigation of mucosal membranes from IBD patients showed an upregulation of CD4+ cells which were either Th1 (IFNg/IL-2) or Th2 (IL5/TGFb) biased depending on whether the patient had Crohn's disease or ulcerative colitis (Fuss I J. et al. *J Immunol.* 1996 157:1261-70.). Similarly, T cells are known to play a key role in inflammatory disorders of the eye with several studies reporting increased levels of T cell associated cytokines (IL-17 and IL-23) in sera of Bechet's patients (Chi W. et al. *Invest Ophthalmol Vis Sci.* 2008 49:3058-64). In support, Direskeneli and colleagues demonstrated that Beçhet's patients have increased Th17 cells and decreased Treg cells in their peripheral blood (Direskeneli H. et al. J Allergy Clin Immunol. 2011 128: 665-6).

One approach to inhibit T cell activation is to target kinases which are involved in activation of the T cell receptor signalling complex. Syk and Src family kinases are known to play a key role in this pathway, where Src family kinases, Fyn and Lek, are the first signalling molecules to be activated downstream of the T cell receptor (Barber E K. et al. *PNAS* 1989 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science.* 1994 10; 264(5165):1599-601).

A clinical trial in rheumatoid arthritis patients with the Syk inhibitor Fostamatinib demonstrated the potential of Syk as an anti-inflammatory target with patients showing improved clinical outcome and reduced serum levels of IL-6 and MMP-3 (Weinblatt M E. et al. *Arthritis Rheum.* 2008 58:3309-18). Syk kinase is widely expressed in cells of the hematopoietic system, most notably in B cells and mature T cells. Through interaction with immunoreceptor tyrosine-based activation (ITAM) motifs it plays an important role in regulating T cell and B cell expansion as well as mediating immune-receptor signalling in inflammatory cells. Syk activation leads to IL-6 and MMP release—inflammatory mediators commonly found upregulated in inflammatory disorders including IBD and rheumatoid arthritis (Wang Y D. et al *World J Gastroenterol* 2007; 13: 5926-5932, Litinsky I et al. *Cytokine.* 2006 January 33:106-10).

In addition to playing key roles in cell signalling events which control the activity of pro-inflammatory pathways, kinase enzymes are now also recognised to regulate the activity of a range of cellular functions, including the maintenance of DNA integrity (Shilo, Y. *Nature Reviews Cancer,* 2003, 3: 155-168) and co-ordination of the complex processes of cell division. Indeed, certain kinase inhibitors (the so-called "Olaharsky kinases") have been found to alter the frequency of micronucleus formation in vitro (Olaharsky, A. J. et al., *PLoS Comput. Biol.,* 2009, 5(7)). Micronucleus formation is implicated in, or associated with, disruption of mitotic processes and is therefore undesirable. Inhibition of glycogen synthase kinase 3α (GSK3α) was found to be a particularly significant factor that increases the likelihood of a kinase inhibitor promoting micronucleus formation. Also, inhibition of the kinase GSK3β with RNAi has been reported to promote micronucleus formation (Tighe, A. et al., *BMC Cell Biology,* 2007, 8:34).

Whilst it may be possible to attenuate the adverse effects of inhibition of Olaharsky kinases such as GSK3α by optimisation of the dose and/or by changing the route of administration of a molecule, it would be advantageous to identify further therapeutically useful molecules with low or negligible inhibition of Olaharsky kinases, such as GSK 3α and/or have low or negligible disruption of mitotic processes (e.g. as measured in a mitosis assay).

Various compounds, including urea derivatives, are disclosed as inhibiting one or more kinases. Examples of such compounds may be found in WO 99/23091, WO 00/043384, WO 00/055139, WO 01/36403, WO 01/4115, WO 02/092576, WO 2003/005999, WO 2003/068228, WO 2003/072569, WO 2004/113352, WO 2005/018624, WO 2007/053394, *Bioorg. Med. Chem. Lett.* 2002, 12, 1559-1562, *Curr. Opin. Drug Devel.* 2004, 7(5), 600-616, *Bioorg. Med. Chem. Lett.* 2007, 17, 354-357 and *Curr. Top. Med. Chem.* 2008, 8, 1452-1467.

Nevertheless, there remains a need to identify and develop new kinase inhibitors, specifically alternative p38 MAP kinase inhibitors that are suitable for the treatment of inflammation. There is particularly a need for such inhibitors that have improved therapeutic potential over currently available treatments or, in particular, that exhibit a superior therapeutic index (e.g. inhibitors that are at least equally efficacious and, in one or more respects, are less toxic at the relevant therapeutic dose than previous agents).

Comparative studies have demonstrated that BIRB 796, in which the pyrazole group bears an aromatic (p-tolyl) substituent in the 2-position, has a much greater affinity for p38 MAP kinase than does the corresponding compound in which the p-tolyl substituent is replaced by methyl (see, for example, Regan et al., *Bioorg. Med. Chem. Lett.* 2003, 13, 3101-3104, Kroe et al., *J. Med. Chem.* 2003, 46, 4669-4675 and Regan et al., *J. Med. Chem.* 2003, 46, 4676-4686). Similarly, superior p38 MAP kinase binding affinity, and correspondingly superior inhibition of cytokine release, has been observed for other urea-based compounds containing N-aryl pyrazole groups, as compared to a structurally related compound containing an N-methyl pyrazole group (see, for example, Dumas et al. *Bioorg. Med. Chem. Lett.* 2000, 10, 2051-2054 and Moss et al. *Bioorg. Med. Chem. Lett.* 2007, 17, 4242-4247).

Diaryl urea-based compounds, including compounds based upon N-alkyl pyrazoles, are disclosed in WO 2005/048948 in connection with the inhibition of a range of different kinases.

We have now discovered, surprisingly, that certain aniline-substituted diaryl ureas inhibit one or more of p38 MAP kinase, Syk and Src family kinases and therefore possess good anti-inflammatory properties.

Thus, according to a first aspect of the invention, there is provided a compound of formula I,

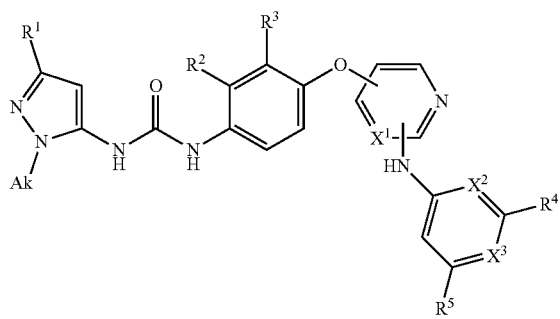

wherein

Ak represents $C_{1-4}$ alkyl;

$R^1$ represents trimethylsilyl, $C_{2-7}$ alkyl, $C_{2-7}$ alkenyl, $C_{2-7}$ alkynyl, $C_{3-7}$ cycloalkyl, phenyl, Het$^1$ or Het$^2$, which latter seven groups are optionally substituted by one or more substituents selected from $C_{1-2}$ alkyl, halo, hydroxy, and $C_{1-2}$ alkoxy;

$R^2$ and $R^3$, together with the C-atoms to which they are attached, form a fused phenyl or pyridyl ring, which latter two rings are optionally substituted by one or more substituents selected from $C_{1-3}$ alkyl, $C_{1-3}$ haloalkyl, cyano and halo, or one of $R^2$ and $R^3$ represents H, halo, cyano, $C_{1-3}$ alkyl or $C_{1-3}$ haloalkyl and the other independently represents halo, cyano, $C_{1-3}$ alkyl or $C_{1-3}$ haloalkyl, or $R^2$ and $R^3$ together combine to form $C_{3-5}$ alkylene or $C_{3-5}$ alkenylene, which latter two groups are optionally substituted by one or more substituents selected from $C_{1-3}$ alkyl, $C_{1-3}$ haloalkyl, cyano and halo;

$X^1$ represents N or CH;

$X^2$ and $X^3$ both represent $CR^Z$ or one of $X^2$ and $X^3$ represents N and the other represents $CR^Z$;

$R^Z$ represents H, halo, cyano, $C_{1-3}$ alkyl or $C_{1-3}$ alkoxy, which latter two groups are optionally substituted by one or more halo atoms;

$R^4$ represents
- $Q^1$-[CH$_2$(CH$_2$)$_{0-1}$CH$_2$—O]$_{1-12}$—CH$_2$(CH$_2$)$_{0-1}$CH$_2$—$R^{6a}$,
- $Q^2$-C($R^{6c}$)($R^{6d}$)—[$C_{1-5}$ alkylene]-$R^{6a}$ or
- —S(O)$_n$$R^{6b}$;

$R^5$ represents $C_{1-3}$ alkoxy or $C_{1-3}$ alkyl, which latter two groups are optionally substituted by one or more halo atoms, or $R^5$ represents H, cyano, halo or $C_{2-3}$ alkynyl;

$R^{6a}$ represents OR$^{7a}$ or N(R$^{7b}$)R$^{7c}$;

$R^{6b}$ represents $C_{1-8}$ alkyl, $C_{3-8}$ cycloalkyl, phenyl, Het$^1$ or Het$^2$, which latter five groups are optionally substituted by one or more substituents selected from halo, hydroxyl, $C_{1-3}$ alkyl and $C_{1-3}$ alkoxy;

$R^{6c}$ and $R^{6d}$ independently represent H or methyl;

$R^7$ to $R^{7c}$ independently represent H or $C_{1-4}$ alkyl optionally substituted by one or more halo atoms, or $R^{7b}$ and $R^{7c}$, together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from halo, hydroxy, oxo, $C_{1-4}$ alkyl and $C_{1-4}$ alkoxy;

$Q^1$ and $Q^2$ independently represent C(O)NH, O or S(O)$_p$;

n and p independently represent 0, 1 or 2,

Het$^1$ represents 5- or 6-membered heterocyclic group that is fully aromatic, which group contains one or more heteroatoms selected from N, O and S; and Het$^2$ represents a 4- to 7-membered heterocyclic group that is fully saturated or partially unsaturated, which group contains one or more heteroatoms selected from N, O and S; or a pharmaceutically acceptable salt, solvate or isotopic derivative thereof, which compounds may be referred to hereinafter as "the compounds of the invention".

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals.

For the avoidance of doubt, compounds of formula I may contain the stated atoms in any of their natural or non-natural isotopic forms. In this respect, embodiments of the invention that may be mentioned include those in which:

(a) the compound of formula I is not isotopically enriched or labelled with respect to any atoms of the compound; and (b) the compound of formula I is isotopically enriched or labelled with respect to one or more atoms of the compound.

References herein to an "isotopic derivative" relate to the second of these two embodiments. In particular embodiments of the invention, the compound of formula I is isotopically enriched or labelled (with respect to one or more atoms of the compound) with one or more stable isotopes. Thus, the compounds of the invention that may be mentioned include, for example, compounds of formula I that are isotopically enriched or labelled with one or more atoms such as deuterium or the like.

Compounds of formula I may exhibit tautomerism. All tautomeric forms and mixtures thereof are included within the scope of the invention.

Unless otherwise specified, alkyl groups and alkoxy groups as defined herein may be straight-chain or, when there is a sufficient number (i.e. a minimum of three) of carbon atoms, be branched. Particular alkyl groups that may be mentioned include, for example, methyl, ethyl, n-propyl, iso-propyl, butyl, n-butyl and tert-butyl. Particular alkoxy groups that may be mentioned include, for example, methoxy, ethoxy, propoxy, and butoxy.

Unless otherwise specified, cycloalkyl groups as defined herein may, when there is a sufficient number (i.e. a minimum of four) of carbon atoms, be part cyclic/acyclic.

Unless otherwise specified, alkylene groups as defined herein may be straight-chain or, when there is a sufficient number (i.e. a minimum of two) of carbon atoms, be branched. In particular embodiments of the invention, alkylene refers to straight-chain alkylene.

Unless otherwise stated, the point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like. Embodiments of the invention that may be mentioned include those in which aryl is phenyl.

For the avoidance of doubt, oxo substituents that may be present on heterocyclic groups represented by N(R$^{7b}$)R$^{7c}$ may be attached to any appropriate atoms in the heterocyclic ring including, where valencies allow, to C-, N- and/or S-atoms within the ring (thereby forming keto, N-oxide, S(O) and/or S(O)$_2$ groups).

Values of Het$^2$ that may be mentioned include oxetanyl (e.g. 3-oxetanyl) or tetrahydropyranyl (e.g. 4-tetrahydropyranyl).

Unless otherwise specified, the term "halo" includes references to fluoro, chloro, bromo or iodo, in particular to fluoro, chloro or bromo, especially fluoro or chloro.

Embodiments of the invention that may be mentioned include those in which the compound of formula I is a compound of formula Ia,

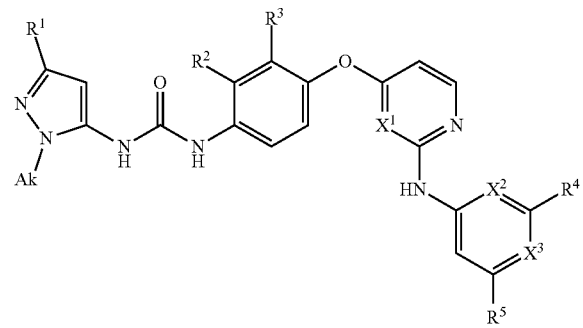

Ia or a pharmaceutically acceptable salt, solvate or isotopic derivative thereof, wherein R$^1$ to R$^5$, Ak and X$^1$ to X$^3$ are as hereinbefore defined.

Embodiments of the invention that may be mentioned include those in which one or more of the following definitions apply to the compounds of formula I and Ia:

(a) Ak represents C$_{1-3}$ alkyl (e.g. C$_{1-2}$ alkyl such as ethyl or, particularly, methyl);
(b) R$^1$ represents trimethylsilyl, C$_{3-5}$ n-alkyl, C$_{4-7}$ branched alkyl, C(C$_{1-2}$ alkyl)$_2$—C≡CH, or C$_{3-5}$ cycloalkyl, which latter group is optionally substituted by C$_{1-2}$ alkyl;
(c) R$^2$ and R$^3$, together with the C-atoms to which they are attached, form a fused phenyl ring, or R$^2$ and R$^3$ independently represent halo or C$_{1-2}$ alkyl;
(d) X$^1$ represents N or CH;
(e) X$^2$ and X$^3$ both represent CH or one of X$^2$ represents CH and X$^3$ represents N or CR$^Z$;
(f) R$^Z$ represents H or halo;
(g) R$^4$ represents
-Q$^1$-[CH$_2$CH$_2$—O]$_{1-8}$—CH$_2$CH$_2$—R$^{6a}$,
-Q$^2$-CH$_2$—[C$_{1-2}$ alkylene]-R$^{6a}$ or
—S(O)$_n$R$^{6b}$;
(h) R$^5$ represents H or, particularly, cyano, chloro, fluoro, C$_{2-3}$ alkynyl, C$_{1-2}$ alkyl or C$_{1-2}$ alkoxy, which latter two groups are optionally substituted by one or more fluoro atoms;
(i) R$^{6a}$ represents OH, O—C$_{1-2}$ alkyl or N(R$^{7b}$)R$^{7c}$;
(j) R$^{6b}$ represents C$_{1-5}$ alkyl or C$_{3-5}$ cycloalkyl;
(k) R$^{7b}$ and R$^{7c}$ independently represent H or C$_{1-2}$ alkyl (e.g. methyl), or R$^{7b}$ and R$^{7c}$, together with the N-atom to which they are attached, form a 4- to 7-membered heterocyclic group that is fully saturated, which heterocyclic group contains one N atom (the atom to which R$^{7b}$ and R$^{7c}$ are attached) and, optionally, one further heteroatom selected from O, S and N, and which heterocyclic group is optionally substituted by one or more C$_{1-2}$ alkyl groups;
(l) Q$^1$ and Q$^2$ independently represent C(O)NH or O;
(m) n represents 0 or 2.

Further embodiments of the invention that may be mentioned include those in which the compound of formula I or Ia is a compound of formula Ib, Ib or a pharmaceutically acceptable salt, solvate or isotopic derivative thereof, wherein R$^1$ to R$^5$, Ak and X$^1$ are as hereinbefore defined.

Embodiments of the invention that may be mentioned include those in which one or more of the following definitions apply to the compounds of formula I, Ia and Ib:

(a) Ak represents ethyl or, particularly, methyl;
(b) R$^1$ represents C$_{4-5}$ branched alkyl (e.g. tert-butyl), C(CH$_3$)$_2$—C≡CH, or cyclopropyl, which latter group is optionally substituted by methyl;
(c) R$^2$ and R$^3$ both represent chloro or, particularly, R$^2$ and R$^3$, together with the C-atoms to which they are attached, form a fused phenyl ring;
(d) X$^1$ represents CH or, particularly, N;
(e) R$^4$ represents
-Q$^1$-[CH$_2$CH$_2$—O]$_{1-7}$—CH$_2$CH$_2$—R$^{6a}$,
—C(O)NH—CH$_2$—[C$_{1-2}$ alkylene]-R$^{6a}$ or
—S(O)$_2$R$^{6b}$;
(f) R$^5$ represents C$_{2-3}$ alkynyl, C$_{1-2}$ alkyl or C$_{1-2}$ alkoxy, which latter two groups are optionally substituted by one or more fluoro atoms (e.g. R$^5$ represents methyl, trifluoromethyl or, particularly, —C≡CH or methoxy, which latter group is optionally substituted by one or more fluoro atoms);
(g) R$^{6a}$ represents O—CH$_3$ or N(R$^{7b}$)R$^{7c}$;
(h) R$^{6b}$ represents C$_{3-5}$ cycloalkyl (e.g. cyclopropyl);
(i) R$^{7b}$ and R$^{7c}$ both represent methyl, or R$^{7b}$ and R$^{7c}$, together with the N-atom to which they are attached, form a 5- or 6-membered heterocyclic group that is fully saturated, which heterocyclic group contains one N atom (the atom to which R$^{7b}$ and R$^{7c}$ are attached) and, optionally, one further heteroatom selected from O, S and N, and which heterocyclic group is optionally substituted by one or more methyl groups;
(j) Q$^1$ represents C(O)NH or O.

Still further embodiments of the invention that may be mentioned include those in which the compound of formula I, Ia or Ib is a compound of formula Ic,

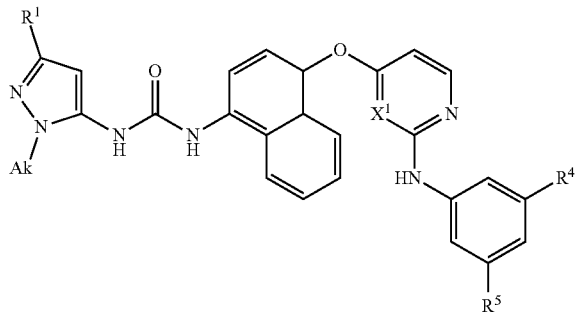

or a pharmaceutically acceptable salt, solvate or isotopic derivative thereof, wherein $R^1$, $R^4$, $R^5$, Ak and $X^1$ are as hereinbefore defined.

Embodiments of the invention that may be mentioned include those in which one or more of the following definitions apply to the compounds of formula I, Ia, Ib and Ic:
(a) Ak represents ethyl or, particularly, methyl;
(b) $R^1$ represents $C_{4-5}$ branched alkyl (e.g. tert-butyl);
(c) $X^1$ represents N;
(d) $R^4$ represents
  -$Q^1$-[$CH_2CH_2$—O]$_{2-6}$—$CH_2CH_2$—$OCH_3$ (e.g. -$Q^1$-[$CH_2CH_2$—O]$_{2-3}$—$CH_2CH_2$—$OCH_3$),
  —C(O)NH—$CH_2$—$CH_2$—N($R^{7b}$)$R^{7c}$ or
  —S(O)$_2$-cyclopropyl;
(e) $R^5$ represents —C≡CH or, particularly, methoxy;
(f) $R^{6a}$ represents O—$CH_3$ or N($R^{7b}$)$R^{7c}$;
(g) $R^{7b}$ and $R^{7c}$ both represent methyl, or $R^{7b}$ and $R^{7c}$, together with the N-atom to which they are attached, form a piperazinyl group optionally substituted by methyl or, particularly, a morpholinyl group; and/or
(h) $Q^1$ represents C(O)NH or, particularly, O.

Further embodiments of the invention that may be mentioned include those in which:
$R^4$ represents
  —C(O)NH—[$CH_2CH_2$—O]$_{2-6}$—$CH_2CH_2$—$OCH_3$ (e.g. —C(O)NH—[$CH_2CH_2$—O]$_{2-3}$—$CH_2CH_2$—$OCH_3$),
  —C(O)NH—$CH_2$—$CH_2$—N($R^{7b}$)$R^{7c}$ or
  —S(O)$_2$-cyclopropyl; and
$R^5$ represents methoxy or, particularly, —C≡CH.

Further embodiments of the invention that may be mentioned include those in which, in the compounds of formula I, Ia, Ib or Ic as defined above:
$X^2$ and $X^3$ both represent CH;
$R^4$ represents
  -$Q^1$-[$CH_2(CH_2)_{0-1}CH_2$—O]$_{1-12}$—$CH_2(CH_2)_{0-1}CH_2$—$R^{6a}$ or
  -$Q^2$-C($R^{6c}$)($R^{6d}$)—[$C_{1-5}$ alkylene]-$R^{6a}$; or
$R^{6b}$ represents $C_{3-8}$ cycloalkyl, phenyl, Het$^1$ or Het$^2$, which latter four groups are optionally substituted by one or more substituents selected from halo, hydroxyl, $C_{1-3}$ alkyl and $C_{1-3}$ alkoxy.

Other compounds of formula I, Ia, Ib or Ic that may be mentioned include the compounds of the examples described hereinafter. Thus, embodiments of the invention that may be mentioned include those in which the compound of formula I, Ia, Ib or Ic is a compound selected from the list:
3-((4-((4-(3-(3-(tert-butyl)-1-methyl-1H-pyrazol-5-yl) ureido)naphthalen-1-yl)oxy)pyrimidin-2-yl)amino)-5-ethynyl-N-(2-morpholinoethyl)benzamide;
1-(3-(tert-butyl)-1-methyl-1H-pyrazol-5-yl)-3-(4-((2-((3-methoxy-5-(2-(2-(2-methoxyethoxy)-ethoxy)ethoxy)phenyl)amino)pyrimidin-4-yl)oxy)naphthalen-1-yl)urea;
1-(3-(tert-butyl)-1-methyl-1H-pyrazol-5-yl)-3-(4-((2-((3-(cyclopropylsulfonyl)-5-methoxy-phenyl)amino)pyrimidin-4-yl)oxy)naphthalen-1-yl)urea;
3-((4-((4-(3-(3-(tert-butyl)-1-methyl-1H-pyrazol-5-yl) ureido)naphthalen-1-yl)oxy)pyrimidin-2-yl)amino)-5-ethynyl-N-(2-(2-methoxyethoxy)ethyl);
1-(3-(tert-butyl)-1-methyl-1H-pyrazol-5-yl)-3-(4-((2-((3-methoxy-5-(2-(2-(2-methoxy-ethoxy)ethoxy)ethoxy)phenyl)amino)pyridin-4-yl)oxy)naphthalen-1-yl);
1-(4-((2-((3-(2,5,8,11,14,17,20-heptaoxadocosan-22-yloxy)-5-methoxyphenyl)amino)-pyrimidin-4-yl)oxy) naphthalen-1-yl)-3-(3-(tert-butyl)-1-methyl-1H-pyrazol-5-yl)urea,
3-((4-((4-(3-(3-(tert-butyl)-1-methyl-1H-pyrazol-5-yl) ureido)naphthalen-1-yl)oxy)pyrimidin-2-yl)amino)-5-ethynyl-N-(2-(2-(2-methoxyethoxy)ethoxy)ethyl)benzamide;
3-((4-((4-(3-(3-(tert-butyl)-1-ethyl-1H-pyrazol-5-yl)ureido) naphthalen-1-yl)oxy)pyrimidin-2-yl)amino)-5-ethynyl-N-(2-(2-(2-methoxyethoxy)ethoxy)ethyl)benzamide;
3-((4-((4-(3-(3-(tert-butyl)-1-methyl-1H-pyrazol-5-yl) ureido)naphthalen-1-yl)oxy)pyridin-2-yl)amino)-5-ethynyl-N-(2-(2-(2-methoxyethoxy)ethoxy)ethyl)benzamide;
3-ethynyl-5-((4-((4-(3-(3-isopropyl-1-methyl-1H-pyrazol-5-yl)ureido)naphthalen-1-yl)oxy)pyrimidin-2-yl)amino)-N-(2-morpholinoethyl)benzamide;
3-ethynyl-5-((4-((4-(3-(3-isopropyl-1-methyl-1H-pyrazol-5-yl)ureido)naphthalen-1-yl)oxy)pyrimidin-2-yl)amino)-N-(2-(2-(2-methoxyethoxy)ethoxy)ethyl)benzamide;
3-((4-((4-(3-(1,3-di-tert-butyl-1H-pyrazol-5-yl)ureido) naphthalen-1-yl)oxy)pyrimidin-2-yl)amino)-5-ethynyl-N-(2-(2-(2-methoxyethoxy)ethoxy)ethyl)benzamide;
3-((4-((4-(3-(3-(tert-butyl)-1-isopropyl-1H-pyrazol-5-yl) ureido)naphthalen-1-yl)oxy)pyrimidin-2-yl)amino)-5-ethynyl-N-(2-(2-(2-methoxyethoxy)ethoxy)ethyl)-benzamide; and
3-((4-((4-(3-(3-(tert-butyl)-1-propyl-1H-pyrazol-5-yl) ureido)naphthalen-1-yl)oxy)pyrimidin-2-yl)amino)-5-ethynyl-N-(2-(2-(2-methoxyethoxy)ethoxy)ethyl)benzamide, or a pharmaceutically acceptable salt, solvate or isotopic derivative thereof.

Examples of salts of compounds of formula I, Ia, Ib or Ic include all pharmaceutically acceptable salts, such as, without limitation, acid addition salts of strong mineral acids such as HCl and HBr salts and addition salts of strong organic acids such as methanesulfonic acid.

References herein to a compound of the invention (a compound of formula I, Ia, Ib or Ic) are intended to include references to the compound and to all pharmaceutically acceptable salts, solvates and/or tautomers of said compound, unless the context specifically indicates otherwise. In this respect, solvates that may be mentioned include hydrates.

The compounds of the invention (compounds of formula I, Ia, Ib or Ic) are p38 MAP kinase inhibitors (especially of the alpha subtype) and are therefore useful in medicine, in particular for the treatment of inflammatory diseases. Further aspects of the invention that may be mentioned therefore include the following.

(a) A pharmaceutical formulation comprising compound of formula I, Ia, Ib or Ic, as hereinbefore defined, or pharmaceutically acceptable salt, solvate or isotopic derivative thereof, in admixture with a pharmaceutically acceptable adjuvant, diluent or carrier.

(b) A combination product comprising
   (A) a compound of formula I, Ia, Ib or Ic, as hereinbefore defined, or pharmaceutically acceptable salt, solvate or isotopic derivative thereof, and
   (B) another therapeutic agent,
   wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of formula I, Ia, Ib or Ic, as hereinbefore defined, or pharmaceutically acceptable salt, solvate or isotopic derivative thereof, and another therapeutic agent, in admixture with a pharmaceutically acceptable adjuvant, diluent or carrier (which formulation is hereinafter referred to as a "combined preparation").

It also encompasses a kit of parts comprising components:
(i) a pharmaceutical formulation including a compound of formula I, Ia, Ib or Ic, as hereinbefore defined, or pharmaceutically acceptable salt, solvate or isotopic derivative thereof, in admixture with a pharmaceutically acceptable adjuvant, diluent or carrier; and
(ii) a pharmaceutical formulation including another therapeutic agent, in admixture with a pharmaceutically-acceptable adjuvant, diluent or carrier,
which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

(c) A process for preparing the pharmaceutical formulation of aspect (a) above, said process comprising the step of admixing the compound of formula I, Ia, Ib or Ic, as hereinbefore defined, or pharmaceutically acceptable salt, solvate or isotopic derivative thereof, with a pharmaceutically acceptable adjuvant, diluent or carrier.

Embodiments of this aspect of the invention that may be mentioned include those in which the pharmaceutically acceptable adjuvant, diluent or carrier is a topically acceptable adjuvant, diluent or carrier (and/or wherein the process is for preparing a topical pharmaceutical formulation, i.e. a pharmaceutical formulation that is adapted for topical administration).

(d) A compound of formula I, Ia, Ib or Ic, as hereinbefore defined, or pharmaceutically acceptable salt, solvate or isotopic derivative thereof, for use in medicine (or for use as a medicament or as a pharmaceutical).

(e) A compound of formula I, Ia, Ib or Ic, as hereinbefore defined, or pharmaceutically acceptable salt, solvate or isotopic derivative thereof, or a pharmaceutical formulation or combination product as defined in connection with aspect (a) or (b) of the invention, for use in the treatment or prevention of an inflammatory disease.

(f) The use of
   a compound of formula I, Ia, Ib or Ic, as hereinbefore defined, or pharmaceutically acceptable salt, solvate or isotopic derivative thereof, or
   a pharmaceutical formulation or combination product as defined in connection with aspect (a) or (b) of the invention,
   for the preparation of a medicament for the treatment or prevention of an inflammatory disease.

(g) A method of treating or preventing an inflammatory disease, said method comprising administering to a subject an effective amount of
   a compound of formula I, Ia, Ib or Ic, as hereinbefore defined, or pharmaceutically acceptable salt, solvate or isotopic derivative thereof, or
   a pharmaceutical formulation or combination product as defined in connection with aspect (a) or (b) of the invention.

(h) A method of sensitizing a subject to the anti-inflammatory effects of a corticosteroid, said method comprising administering to the subject an effective amount of
   a compound of formula I, Ia, Ib or Ic, as hereinbefore defined, or pharmaceutically acceptable salt, solvate or isotopic derivative thereof, or
   a pharmaceutical formulation or combination product as defined in connection with aspect (a) or (b) of the invention.

Embodiments of this aspect of the invention that may be mentioned include those in which the subject is one who has become refractory to the anti-inflammatory effects of a corticosteroid.

Formulations

In relation to aspects (a) and (b) above, diluents and carriers that may be mentioned include those suitable for parenteral, oral, topical, mucosal and rectal administration.

The pharmaceutical formulations and combination products of aspects (a) and (b) above may be prepared e.g. for parenteral, subcutaneous, intramuscular, intravenous, intra-articular, intravitreous, periocular, retrobulbar, subconjunctival, sub-Tenon, topical ocular or peri-articular administration, particularly in the form of liquid solutions, emulsions or suspensions; for oral administration, particularly in the form of tablets or capsules, and especially involving technologies aimed at furnishing colon-targeted drug release (Patel, M. M. *Expert Opin. Drug Deliv.* 2011, 8 (10), 1247-1258); for topical e.g. pulmonary or intranasal administration, particularly in the form of powders, nasal drops or aerosols and transdermal administration; for topical ocular administration, particularly in the form of solutions, emulsions, suspensions, ointments, implants/inserts, gels, jellies or liposomal microparticle formulations (Ghate, D.; Edelhauser, H. F. *Expert Opin. Drug Deliv.* 2006, 3 (2), 275-287); for ocular administration, particularly in the form of biodegradable and non-biodegradable implants, liposomes and nanoparticles (Thrimawithana, T. R. et al. *Drug Discov. Today* 2011, 16 (5/6), 270-277); for mucosal administration e.g. to buccal, sublingual or vaginal mucosa, and for rectal administration e.g. in the form of a suppository or enema.

The pharmaceutical formulations and combination products of aspects (a) and (b) above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration typical excipients include sugars, calcium stearate, magnesium stearate, pregelatinated starch, and the like.

Pharmaceutical formulations and combination products suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate.

Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

A compound of the invention may be administered topically (e.g. to the lung, eye or intestines). Thus, embodiments of aspects (a) and (b) above that may be mentioned include pharmaceutical formulations and combination products that are adapted for topical administration. Such formulations include those in which the excipients (including any adjuvant, diluent and/or carrier) are topically acceptable.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoroethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean aerodynamic diameter (MMAD) of 1-10 µm. The formulation will typically contain a topically acceptable diluent such as lactose, usually of large particle size e.g. an MMAD of 100 µm or more. Examples of dry powder delivery systems include SPINHALER, DISKHALER, TURBOHALER, DISKUS and CLICKHALER.

The compounds of the present invention may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides, e.g., Suppocire. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyoxyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers, polycarbophil and Pemulen®, specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family, vinyl polymers and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

Embodiments of the invention that may be mentioned in connection with the combination products described at (b) above include those in which the other therapeutic agent is one or more therapeutic agents that are known by those skilled in the art to be suitable for treating inflammatory diseases (e.g. the specific diseases mentioned below).

For example, for the treatment of respiratory disorders (such as COPD or asthma), the other therapeutic agent is one or more agents selected from the list comprising:

steroids (e.g. budesonide, beclomethasone dipropionate, fluticasone propionate, mometasone furoate, fluticasone furoate);
  beta agonists (e.g. terbutaline, salbutamol, salmeterol, formoterol); and
  xanthines (e.g. theophylline).

Further, for the treatment of gastrointestinal disorders (such as Crohn's disease or ulcerative colitis), the other therapeutic agent may be, for example, one or more agents selected from the list comprising:

5-aminosalicylic acid, or a prodrug thereof (such as sulfasalazine, olsalazine or bisalazide);
  corticosteroids (e.g. prednisolone, methylprednisolone, or budesonide);
  immunosuppressants (e.g. cyclosporin, tacrolimus, methotrexate, azathioprine or 6-mercaptopurine);
  anti-TNFα antibodies (e.g., infliximab, adalimumab, certolizumab pegol or golimumab);
  anti-IL12/IL23 antibodies (e.g., ustekinumab) or small molecule IL12/IL23 inhibitors (e.g., apilimod);
  Anti-α4β7 antibodies (e.g., vedolizumab);
  MAdCAM-1 blockers (e.g., PF-00547659);
  antibodies against the cell adhesion molecule α4-integrin (e.g., natalizumab);
  antibodies against the IL2 receptor α subunit (e.g., daclizumab or basiliximab);
  JAK3 inhibitors (e.g., tofacitinib or R348);
  Syk inhibitors and prodrugs thereof (e.g., fostamatinib and R-406);
  Phosphodiesterase-4 inhibitors (e.g., tetomilast);
  HMPL-004;
  probiotics;
  Dersalazine;
  semapimod/CPSI-2364; and
  protein kinase C inhibitors (e.g. AEB-071).

For the treatment of eye disorders (such as uveitis), the other therapeutic agent may be, for example, one or more agents selected from the list comprising:

corticosteroids (e.g. dexamethasone, prednisolone, triamcinolone acetonide, difluprednate or fluocinolone acetonide);
  immunosuppressants (e.g. cyclosporin, voclosporin, azathioprine, methotrexate, mycophenolate mofetil or tacrolimus);
  anti-TNFα antibodies (e.g., infliximab, adalimumab, certolizumab pegol, ESBA-105 or golimumab);
  anti-IL-17A antibodies (e.g., secukinumab);
  mTOR inhibitors (e.g., sirolimus);
  VGX-1027;
  JAK3 inhibitors (e.g., tofacitinib or R348); and
  protein kinase C inhibitors (e.g. AEB-071).

Medical Uses

The compounds of the invention may be used as monotherapies for inflammatory diseases, or in combination therapies for such diseases.

Thus, embodiments of aspects (e) to (g) above that may be mentioned include those in which the compound of formula I, Ia, Ib or Ic (or pharmaceutically acceptable salt, solvate or isotopic derivative thereof) is the sole pharmacologically active ingredient utilised in the treatment.

However, in other embodiments of aspects (e) to (g) above, the compound of formula I, Ia, Ib or Ic (or pharmaceutically acceptable salt, solvate or isotopic derivative thereof) is administered to a subject who is also administered one or more other therapeutic agents (e.g. wherein the one or more other therapeutic agents are as defined above in connection with combination products).

When used herein, the term "inflammatory disease" specifically includes references to any one or more of the following:

(i) lung diseases or disorders having an inflammatory component, such as cystic fibrosis, pulmonary hypertension, lung sarcoidosis, idiopathic pulmonary fibrosis or, particularly, COPD (including chronic bronchitis and emphysema), asthma or paediatric asthma;

(ii) skin diseases or disorders having an inflammatory component, such as atopic dermatitis, allergic dermatitis, contact dermatitis or psoriasis;

(iii) nasal diseases or disorders having an inflammatory component, such as allergic rhinitis, rhinitis or sinusitis;

(iv) eye diseases or disorders having an inflammatory component, such as conjunctivitis, allergic conjunctivitis, glaucoma, diabetic retinopathy, macular oedema (including diabetic macular oedema), central retinal vein occlusion (CRVO), dry and/or wet age related macular degeneration (AMD), post-operative cataract inflammation, or, particularly, keratoconjunctivitis sicca (dry eye), uveitis (including posterior, anterior and pan uveitis), corneal graft and limbal cell transplant rejection; and (v) gastrointestinal diseases or disorders having an inflammatory component, such as gluten sensitive enteropathy (coeliac disease), eosinophilic esophagitis, intestinal graft versus host disease or, particularly, Crohn's disease or ulcerative colitis.

References herein to diseases having an inflammatory component include references to diseases that involve inflammation, whether or not there are other (non-inflammatory) symptoms or consequences of the disease.

According to a further aspect of the invention there is provided a process for the preparation of a compound of formula I which process comprises:

(a) reaction of a compound of formula

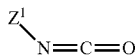

with a compound of formula III,

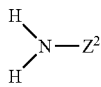

wherein one of $Z^1$ and $Z^2$ is a structural fragment of formula IV

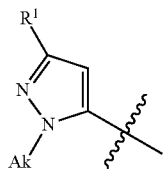

and the other of $Z^1$ and $Z^2$ is a structural fragment of formula V

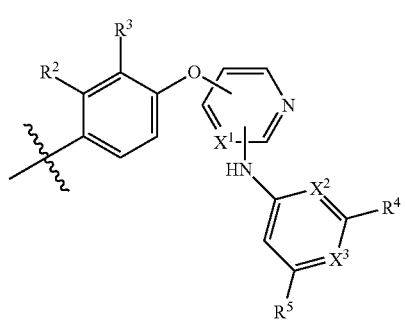

where $R^1$ to $R^5$, Ak and $X^1$ to $X^3$ are as hereinbefore defined, for example under conditions known to those skilled in the art, for example at a temperature from ambient (e.g. 15 to 30° C.) to about 110° C. in the presence of a suitable organic solvent (e.g. a polar aprotic solvent such as DMF, THF, 1,4-dioxane, or mixtures thereof);

(b) reaction of a compound of formula IIa,

wherein $Z^1$ is as defined above, with a suitable azide-forming agent (i.e. a suitable source of a leaving group and activated azide ion, such as diphenyl phosphorazidate; see, for example, Tetrahedron 1974, 30, 2151-2157) under conditions known to those skilled in the art, such as at sub-ambient to ambient temperature (e.g. from an initial temperature of about −5 to 5° C. to ambient temperature post-reaction) in the presence of an amine base (e.g. triethylamine or a sterically hindered base such as N,N-diisopropylethylamine) and a suitable organic solvent (e.g. a polar aprotic solvent such as DMF, THF, 1,4-dioxane, or mixtures thereof), which reaction is followed, without isolation, by thermal rearrangement (e.g. under heating) of the intermediate acyl azide (of formula $Z^1$—C(O)—$N_3$) e.g. at ambient temperature (such as from 15 to 30° C.) to provide, in situ, a compound of formula II, which compound is then reacted with a compound of formula III, as defined above, to provide the compound of formula I;

(c) reaction of a compound of formula IIb,

wherein $LG^1$ represents a suitable leaving group (e.g. imidazolyl, chloro, or aryloxy, such as phenoxy) and $Z^1$ is as defined above, with a compound of formula III, as defined above, for example under conditions known to those skilled in the art, such as at ambient temperature (e.g. from ambient to 80° C.), optionally in the presence of an amine base (e.g. triethylamine or a sterically hindered base like N,N-diisopropylethylamine) and a suitable organic solvent (e.g. an aprotic solvent, such as dichloromethane or an ester such as isopropyl acetate);

(d) reaction of a compound of formula VI,

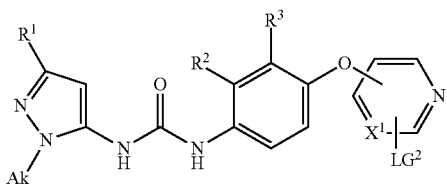

wherein $LG^2$ represents a suitable leaving group (e.g. a halo group such as chloro or bromo) and $R^1$ to $R^3$, Ak and $X^1$ are as hereinbefore defined with a compound of formula VII,

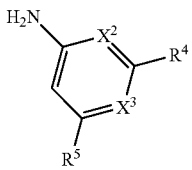

wherein $R^4$, $R^5$, $X^2$ and $X^3$ are as hereinbefore defined, for example under conditions known to those skilled in the art (e.g. as described in *J. Am. Chem. Soc.* 2011, 133, 15686-15696), such as at elevated temperature (e.g. from 50 to 110° C.) in the presence of a suitable organic solvent (e.g. a polar aprotic solvent such as DMF, THF, 1,4-dioxane, or mixtures thereof) and, optionally, an acidic catalyst (e.g. a sulfonic acid such as para-toluenesulfonic acid); or (e) for compounds of formula I in which $R^4$ represents —S(O)$_{1-2}$—[CH$_2$(CH$_2$)$_{0-1}$CH$_2$—O]$_{1-12}$—CH$_2$(CH$_2$)$_{0-1}$CH$_2$—R$^{6a}$, S(O)$_{1-2}$—C(R$^{6c}$)(R$^{6d}$)—[C$_{1-5}$ alkylene]-R$^{6a}$, —S(O)$_{1-2}$R$^{6b}$, oxidation of a corresponding compound of formula I in which, respectively, $R^4$ represents —S—[CH$_2$(CH$_2$)$_{0-1}$CH$_2$—O]$_{1-12}$—CH$_2$(CH$_2$)$_{0-1}$CH$_2$—R$^{5a}$, —S—CH$_2$—[C$_{1-5}$ alkylene]-R$^{6a}$, —S—R$^{6b}$, wherein $R^{6a}$ to $R^{6d}$ are as hereinbefore defined, for example under conditions known to those skilled in the art (e.g. at 0 to 25° C. in the presence of a suitable solvent (such as dichloromethane, methanol or a mixture thereof) and a peracid, such as meta-chloroperbenzoic acid);

(f) for compounds of formula I in which $R^4$ represents

—C(O)NH—[CH$_2$(CH$_2$)$_{0-1}$CH$_2$—O]$_{1-12}$—CH$_2$(CH$_2$)$_{0-1}$CH$_2$—R$^{6a}$ or

—C(O)NH—C(R$^{6c}$)(R$^{6d}$)—[C$_{1-5}$ alkylene]-R$^{6a}$, reaction of a compound of formula VIIa,

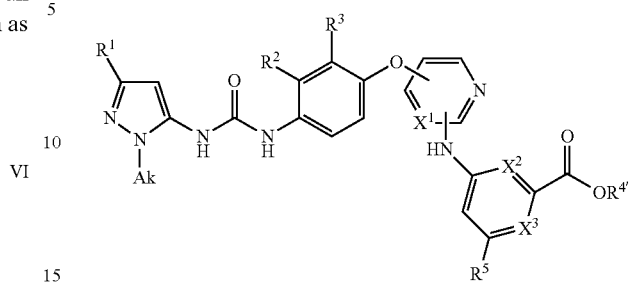

wherein $R^{4'}$ represents H or a C$_{1-3}$ alkyl group (e.g. methyl) and Ak, $R^1$ to $R^3$, $R^5$ and $X^1$ to $X^3$ are as hereinbefore defined, with a compound of formula VIIb or VIIc, H$_2$N—[CH$_2$(CH$_2$)$_{0-1}$CH$_2$—O]$_{1-12}$—CH$_2$(CH$_2$)$_{0-1}$CH$_2$—R$^{6a}$      VIIb H$_2$N—C(R$^{6c}$)(R$^{6d}$)—[C$_{1-5}$ alkylene]-R$^{6a}$ or      VIIc wherein $R^{6a}$, $R^{6c}$ and $R^{6d}$ are as hereinbefore defined, for example under conditions known to those skilled in the art, such as (i) when $R^{4'}$ represents a C$_{1-3}$ alkyl group, reaction at ambient temperature in the presence of a suitable Lewis acidic catalyst (e.g. a trialkyl aluminium reagent such as trimethylaluminium) and an aprotic organic solvent (e.g. THF) or (ii) when $R^{4'}$ represents H, reaction in the presence of a tertiary amine base (e.g. a trialkylamine such as triethylamine or diisopropylethylamine or a cyclic amine such as N-methylpyrrolidine or N-methylmorpholine), an amide (peptide) coupling reagent (e.g. T3P, HATU, CDI, BOP, PyBOP, HOAt, HOBt or a carbodiimide such as DCC or diisopropylcarbodiimide) and an aprotic organic solvent (e.g. a chlorinated solvent such as DCM, an ester such as ethyl acetate, an amide of dimethylamine such as DMF, or a mixture of any such solvents);

(g) deprotection of an protected derivative of a compound of formula I, under conditions known to those skilled in the art, wherein the protected derivative bears a protecting group on an O- or N-atom of the compound of formula I (and, for the avoidance of doubt, a protected derivative of one compound of formula I may or may not represent another compound of formula I).

Compounds of formula II may be prepared according to or by analogy with methods known to those skilled in the art, for example by reaction of a compound of formula IIa, as defined above, with an azide-forming agent, followed by rearrangement of the intermediate acyl azide (as described at (b) above; see, for example, *Tetrahedron* 1974, 30, 2151-2157).

Compounds of formula IIb may be prepared reaction of a compound of formula VIII,

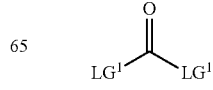

wherein LG¹ is as hereinbefore defined, with a compound of formula IX,

wherein $Z^1$ is as hereinbefore defined, for example under conditions known to those skilled in the art.

Amines of formula IX may be prepared from carboxylic acids of formula IIa through the route described in (b) above, where the intermediate isocyanate II is hydrolysed with water to give a carbamic acid that loses carbon dioxide to furnish IX. By the same token, the intermediate isocyanate II can be reacted with an alcohol, such as t-butanol, to generate a protected version of IX.

Certain compounds of formula III in which $Z^2$ represents a structural fragment of formula V, or compounds of formula IX in which $Z^1$ represents a structural fragment of formula V, may be synthesised employing the route outlined in Organic Synthesis; Wiley, 4th revised edition, 2006; ISBN-10: 0471697540), e.g., a carbamate ester or carboxamide. The sequence starts with the base-mediated $S_NAr$ displacement of $LG^3$ in XI by the aroxides formed when X is treated with base to generate ethers XII. The remaining halogen or methanesulfonyl substituents ($LG^4$) of the ether XII is then displaced i) by an amine of formula VII in a second $S_NAr$ reaction or (ii) via a Buchwald coupling (see, for example, WO 2009/017838) with an amine of formula VII to furnish the desired compound (when FG is $NH_2$), or XIII (when FG is nitro or NH-$PG^2$). When FG is nitro in XIII, the $NH_2$ group may be revealed by a reduction reaction, typically done through hydrogenation employing a suitable catalyst, e.g., palladium on carbon, or employing dissolving metal conditions, such as with iron in glacial acetic acid. Alternatively, when FG is a protecting group, the $NH_2$ group may be revealed by a deprotection reaction. Although only depicted as taking place in the final step of the sequence, it should be noted that the unmasking of the latent $NH_2$ group represented by FG can take place at any stage in the synthetic route shown in Scheme 1.

Scheme 1

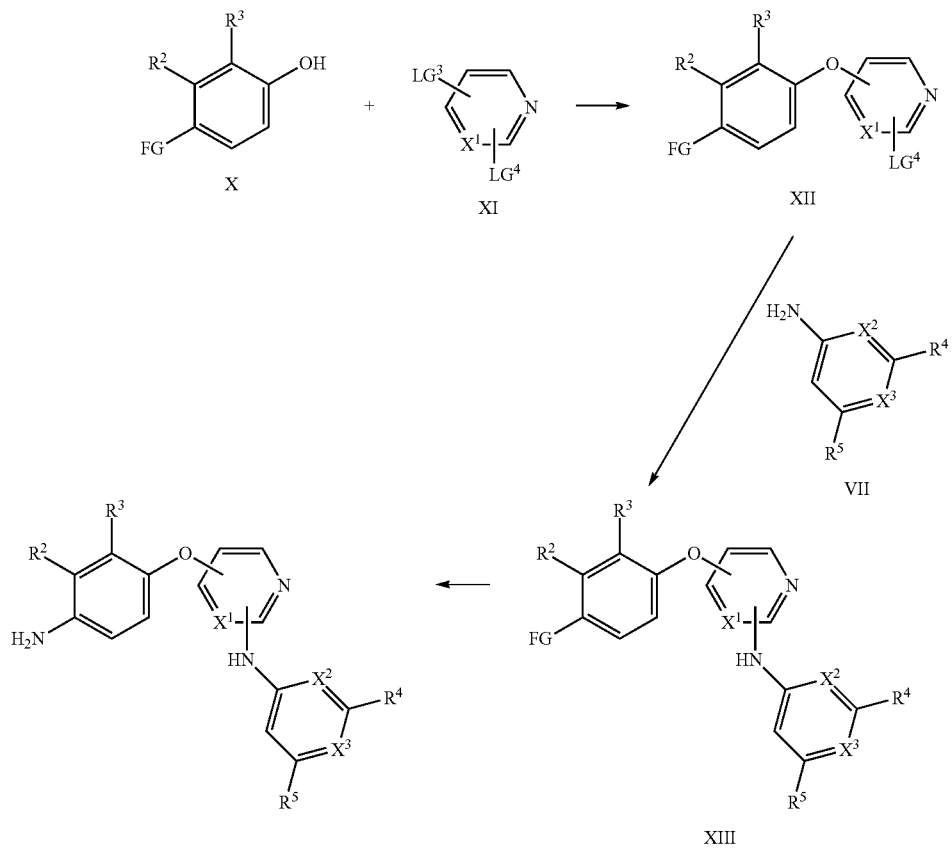

Scheme 1 (see, for example: WO 2003/072569; and WO 2008/046216), wherein $R^2$, $R^3$ and $X^1$ to $X^3$ are as hereinbefore defined, $LG^3$ and $LG^4$ represent leaving groups, e.g., halogen or methanesulfonyl, and FG represents a real or latent $NH_2$ group, i.e., a group that is readily transformed into an $NH_2$ group, such as nitro or a protected variant NH-$PG^2$, where $PG^2$ is a typical protecting group (see, for example: Greene, T. W.; Wuts, P. G. M. *Protective Groups*

Compounds of formula III in which $Z^2$ represents a structural fragment of formula V, or compounds of formula IX in which $Z^1$ represents a structural fragment of formula V, wherein, in the structural fragment of formula V, $R^4$ represents —C(O)NH—[CH$_2$(CH$_2$)$_{0-1}$CH$_2$—O]$_{1-12}$— CH$_2$(CH$_2$)$_{0-1}$CH$_2$—$R^{6a}$ or —C(O)NH—C($R^{6c}$)($R^{6d}$)—[C$_{1-5}$ alkylene]-$R^{6a}$, may be prepared by analogy with processes described herein for preparing compounds of formula I (see process (f) above) and other compounds of formula III (see, for example, Scheme 1 above), for example by reaction of a compound of XIIIa

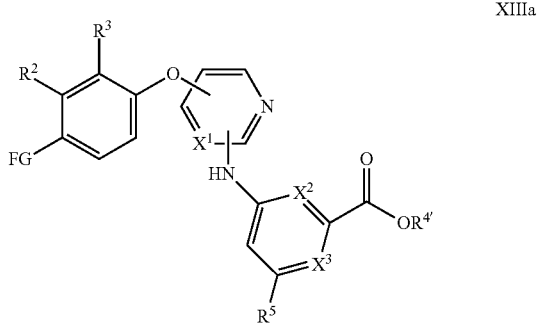

XIIIa wherein FG, $R^2$, $R^3$, $R^{4'}$, $R^5$ and $X^1$ to $X^3$ are as hereinbefore defined, with a compound of formula VIIb or VIIc, as hereinbefore defined, under conditions known to those skilled in the art (for example the peptide coupling conditions described in respect of process (f) above), followed by conversion (if necessary) of FG to $NH_2$, for example as described above in connection with Scheme 1.

Compounds of formula VI may be synthesised by analogy with the compounds of formula I (see, for example, alternative processes (a) to (c) above). For example, compounds of formula VI can be prepared by reaction of a compound of formula IIx with a compound of formula IIIx, wherein the compounds of formulae IIx and IIIx take the same definitions as the compounds of formulae II and III, with the exception that one of $Z^1$ and $Z^2$ represents a structural fragment of formula IV, as hereinbefore defined, and the other of $Z^1$ and $Z^2$ represents a structural fragment of formula Va, Va

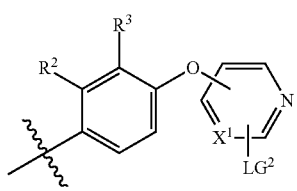

Compounds of formula VII may be prepared according to or by analogy with procedures known to those skilled in the art, for example as described below.

(i) For compounds of formula VII in which $R^4$ represents
—O—$[CH_2(CH_2)_{0-1}CH_2$—$O]_{1-12}$—$CH_2(CH_2)_{0-1}CH_2$—$R^{6a}$ or
—O—$C(R^{6c})(R^{6d})$—$[C_{1-5}$ alkylene]-$R^{6a}$,
reaction of a compound of formula XIV,

XIV

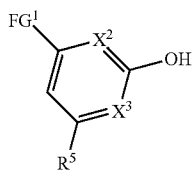

wherein $FG^1$ either represents FG or $C(O)O$—($C_{1-6}$ alkyl), and FG, $R^5$, $X^2$ and $X^3$ are as hereinbefore defined, with a compound of formula XVa or XVb

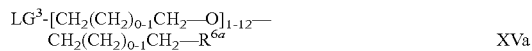

XVa

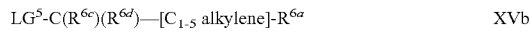

XVb wherein $LG^5$ represents a suitable leaving group such as halo, (perfluoro)alkane-sulfonate or arylsulfonate (e.g. methanesulfonate or p-toluenesulfonate) and $R^{6a}$, $R^{6c}$ and $R^{6d}$ are as hereinbefore defined, under conditions known to those skilled in the art (e.g. in the presence of an organic solvent and either a suitable base, followed by when $FG^1$ represents $NH$-$PG^2$, removal of the $PG^2$ protecting group, when $FG^1$ represents $NO_2$, reduction of $NO_2$ to $NH_2$ or when $FG^1$ represents $C(O)O$—($C_{1-6}$ alkyl), saponification to provide the corresponding carboxylic acid and then reaction with a suitable azide-forming agent and thermal rearrangement of the resulting acyl azide (see, for example, process (b) above).

(ii) For compounds of formula VII in which $R^4$ represents
—O—$[CH_2(CH_2)_{0-1}CH_2$—$O]_{1-12}$—$CH_2(CH_2)_{0-1}CH_2$—$R^{6a}$ or
—O—$C(R^{6c})(R^{6d})$—$[C_{1-5}$ alkylene]-$R^{6a}$
reaction of a compound of formula XIV, as hereinbefore defined, with a compound of formula XVIa or XVIb

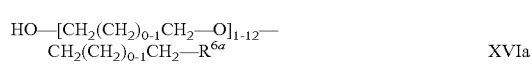

XVIa

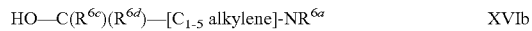

XVIb wherein $R^{6a}$, $R^{6c}$ and $R^{6d}$ are as hereinbefore defined, under conditions known to those skilled in the art (e.g. under Mitsunobu conditions, i.e. in the presence of using triphenylphosphine and an azodicarboxylate, such as diethyl azodicarboxylate or diisopropyl azodicarboxylate), followed by when $FG^1$ represents $NH$-$PG^2$, removal of the $PG^2$ protecting group, when $FG^1$ represents $NO_2$, reduction of $NO_2$ to $NH_2$ or when $FG^1$ represents $C(O)O$—($C_{1-6}$ alkyl), saponification to provide the corresponding carboxylic acid and then reaction with a suitable azide-forming agent and thermal rearrangement of the resulting acyl azide (see, for example, process (b) above).

(iii) For compounds of formula VII in which $R^4$ represents
—S—$[CH_2(CH_2)_{0-1}CH_2$—$O]_{1-12}$—$CH_2(CH_2)_{0-1}CH_2$—$R^{6a}$,
—S—$C(R^{6c})(R^{6d})$—$[C_{1-5}$ alkylene]-$R^{6a}$ or
—S—$R^{6b}$,
reaction of a compound of formula XVII.

XVII

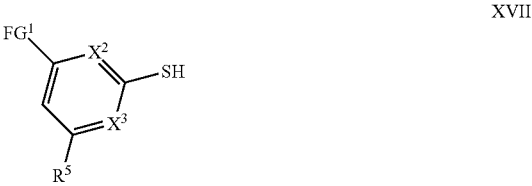

wherein $FG^1$, $R^5$, $X^2$ and $X^3$ are as hereinbefore defined, with a compound of formula XVa or XVb, as hereinbefore defined, or a compound of formula XVIII

XVIII wherein $LG^5$ and $R^{6b}$ are as hereinbefore defined, under conditions known to those skilled in the art (e.g. in the presence of a suitable base and an organic solvent), followed by
when $FG^1$ represents $NH-PG^2$, removal of the $PG^2$ protecting group,
when $FG^1$ represents $NO_2$, reduction of $NO_2$ to $NH_2$ or
when $FG^1$ represents $C(O)O-(C_{1-6}$ alkyl), saponification to provide the corresponding carboxylic acid and then reaction with a suitable azide-forming agent and thermal rearrangement of the resulting acyl azide (see, for example, process (b) above).

(iv) For compounds of formula VII in which $X^2$ and $X^3$ both represent $CR^Z$ and $R^4$ represents
—$S(O)_{1-2}$—$[CH_2(CH_2)_{0-1}CH_2$—$O]_{1-12}$—$CH_2(CH_2)_{0-1}CH_2$—$R^{6a}$,
—$S(O)_{1-2}$—$C(R^{6c})(R^{6d})$—$[C_{1-5}$ alkylene]-$R^{6a}$ or
—$S(O)_{1-2}$—$R^{6b}$,
oxidation of a compound of formula XIX,

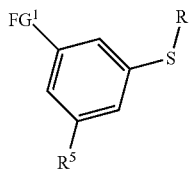

XIX wherein R represents
—$[CH_2(CH_2)_{0-1}CH_2$—$O]_{1-12}$—$CH_2(CH_2)_{0-1}CH_2$—$R^{6a}$,
—$C(R^{6c})(R^{6d})$—$[C_{1-5}$ alkylene]-$R^{6a}$ or
—$R^{61a}$,
and $FG^1$ and $R^5$ are as hereinbefore defined, under conditions known to those skilled in the art (e.g. in the presence of a peracid, such as meta-chloroperbenzoic acid), followed by
when $FG^1$ represents $NH-PG^2$, removal of the $PG^2$ protecting group,
when $FG^1$ represents $NO_2$, reduction of $NO_2$ to $NH_2$ or
when $FG^1$ represents $C(O)O-(C_{1-6}$ alkyl), saponification to provide the corresponding carboxylic acid and then reaction with a suitable azide-forming agent and thermal rearrangement of the resulting acyl azide (see, for example, process (b) above).

(v) For compounds of formula VII in which $R^4$ represents —$S$—$R^{6b}$, coupling of a compound of formula XX

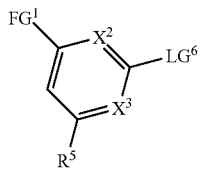

XX wherein $LG^6$ represents a suitable leaving group such as halo or trifluoromethanesulfonate, $FG^1$, $R^5$, $X^2$ and $X^3$ are as hereinbefore defined, with a compound of formula XXI,

H—S—$R^{6b}$    XXI wherein $R^{6b}$ is as hereinbefore defined, under conditions known to those skilled in the art (e.g. in the presence of a Pd(0) catalyst, Cu(I) iodide and a suitable base), followed by when $FG^1$ represents $NH-PG^2$, removal of the $PG^2$ protecting group,
when $FG^1$ represents $NO_2$, reduction of $NO_2$ to $NH_2$ or
when $FG^1$ represents $C(O)O-(C_{1-6}$ alkyl), saponification to provide the corresponding carboxylic acid and then reaction with a suitable azide-forming agent and thermal rearrangement of the resulting acyl azide (see, for example, process (b) above).

(vi) For compounds of formula VII in which $R^4$ represents
-$Q^1$-$[CH_2(CH_2)_{0-1}CH_2$—$O]_{1-12}$—$CH_2(CH_2)_{0-1}CH_2$—$R^{6a}$
wherein $Q^1$ and $R^{6a}$ are as hereinbefore defined, reaction of a compound of formula XXII

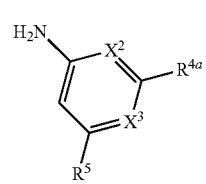

XXII in which $R^{4a}$ represents
-$Q^1$-$[CH_2(CH_2)_{0-1}CH_2$—$O]_x$—$CH_2(CH_2)_{0-1}CH_2$—OH
with a compound of formula XXIII,

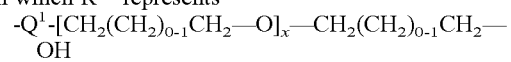

XXIII wherein x and y are integers from 0 to 11, the sum of x and y being from 0 to 11, and $Q^1$, $LG^5$ and $R^{6a}$ are as hereinbefore defined, under conditions known to those skilled in the art (e.g. at ambient temperature in the presence of a base such as sodium hydride and a polar organic solvent such as DMF).

(vii) For compounds of formula VII in which $X^2$ and $X^3$ both represent $CR^Z$ and $R^4$ represents
—$S$—$C(R^{6c})(R^{6d})$—$[C_{1-5}$ alkylene]-$N(R^{7b})R^{7c}$
reaction of a compound of formula XXIV,

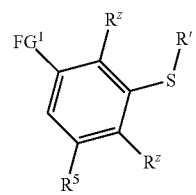

XXIV wherein R' represents
—$C(R^{6b})(R^{6d})$—$[C_{1-5}$ alkylene]-$LG^6$
with a compound of formula $HN(R^{7b})R^{7c}$, wherein $FG^1$, $R^5$, $R^{6b}$, $R^{6c}$, $R^{7b}$, $R^{7c}$, $R^Z$ and $LG^6$ are as hereinbefore defined, under conditions known to those skilled in the art (for example in the presence of a suitable organic solvent (e.g. acetone) and, optionally, catalyst for nucleophilic displacement, such as an iodide sale (e.g. sodium iodide)), followed by
when $FG^1$ represents $NH-PG^2$, removal of the $PG^2$ protecting group,
when $FG^1$ represents $NO_2$, reduction of $NO_2$ to $NH_2$ or
when $FG^1$ represents $C(O)O-(C_{1-6}$ alkyl), saponification to provide the corresponding carboxylic acid and then reaction with a suitable azide-forming agent and thermal rearrangement of the resulting acyl azide (see, for example, process (b) above).

(viii) For compounds of formula VII in which $R^4$ represents
—C(O)NH—[CH$_2$(CH$_2$)$_{0-1}$CH$_2$—O]$_{1-12}$—CH$_2$(CH$_2$)$_{0-1}$CH$_2$—R$^{6a}$ or
—C(O)NH—C(R$^{6b}$)(R$^{6d}$)—[C$_{1-5}$ alkylene]-R$^{6a}$,
reaction of a compound of formula XXV,

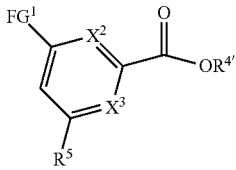

XXV wherein FG$^1$, R$^{4'}$, R$^5$, R$^{6a}$, R$^{6b}$ and R$^{6d}$, X$^2$ and X$^3$ are as hereinbefore defined, with a compound of formula VIIb or VIIc, as hereinbefore defined, under conditions known to those skilled in the art (for example the peptide coupling conditions described in respect of process (f) above), followed by
when FG$^1$ represents NH-PG$^2$, removal of the PG$^2$ protecting group,
when FG$^1$ represents NO$_2$, reduction of NO$_2$ to NH$_2$ or
when FG$^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(ix) For compounds of formula VII in which $R^4$ represents —S(O)$_2$—R$^{6b}$, coupling of a compound of formula XXVI,

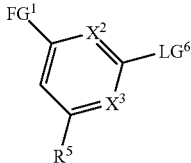

XXVI wherein R$^5$, X$^2$, X$^3$, FG$^1$ and LG$^6$ are as hereinbefore defined, with a compound of formula XXVII, $(M^{s+})(^-O—S(O)—R^{6b})_s$   XXVII wherein M$^{s+}$ is a metal cation, s is 1 or 2 (e.g. s is 1 and M is an alkali metal such as potassium or, particularly, sodium) and R$^{6b}$ is as hereinbefore defined, under conditions known to those skilled in the art (e.g. at elevated temperature (e.g. 80 to 100° C.) in the presence of: a suitable transition metal catalyst, such as Cu(I) iodide; an aprotic organic solvent, such as DMSO; a suitable base, such as an alkali metal hydroxide (e.g. NaOH); and, optionally, an organic ligand for Cu(I), such as L-proline), followed by
when FG$^1$ represents NH-PG$^2$, removal of the PG$^2$ protecting group,
when FG$^1$ represents NO$_2$, reduction of NO$_2$ to NH$_2$ or
when FG$^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

Compounds of formula XXIV in which LG$^6$ represents halo can be prepared according to or by analogy with procedures known to those skilled in the art, for example by reaction of a compound of formula XXVIII,

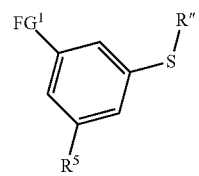

XXVIII wherein R" represents —CH$_2$—[C$_{1-5}$ alkylene]-OH, with a halogenating agent (e.g. a mixture of 2,4,6-trichloro,1,3,5-triazine and dimethylformamide).

It will be understood by persons skilled in the art that compounds represented by formulae II, IIb and IIx are generally reactive intermediates. These intermediates may be formed in situ and reacted directly, without isolation, with compounds of formula III to provide compounds of formula I. Furthermore, it will be understood by those skilled in the art that the use of appropriate protective groups may be required during the processes described above for any of the groups Z$^1$ and Z$^2$ which possess chemically-sensitive functional groups, for example, a hydroxyl group or an amino function.

Many of the compounds illustrated in the Schemes are either commercially available, or can be obtained using the cited procedures, or can be readily prepared by conventional methods by those skilled in the art. See for example Regan, J. et al.; *J. Med. Chem.* 2003, 46, 4676-4686, WO 2000/043384, WO 2007/053346, WO 2007/087448, WO 2007/089512, WO 2009/117080 and WO 2014/027209.

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, have a better pharmacokinetic and/or pharmacodynamic profile than, have more suitable solid state morphology than, have better long term stability than, or may have other useful pharmacological properties over, similar compounds, combinations, methods (treatments) or uses known in the prior art for use in the treatment of those conditions or otherwise.

The compounds of the invention may additionally (or alternatively):
exhibit potent inhibition of kinases (particularly p38 MAP kinase) relative to corresponding compounds in which the group Ak is replaced by an aryl or heteroaryl substituent;
exhibit a long duration of action and/or persistence of action (e.g. in comparison to other previously disclosed p38 MAP kinase inhibitors such as, for example, BIRB796);
not strongly inhibit GSK 3α (e.g. they may have an IC$_{50}$ against GSK 3α of 1500 nM or greater; such as 2,000, 3,000, 4,000, 5,000, 6,000, 7,000, 8,000, 9,000 or 10,000 nM or greater);
maintain a relatively high drug concentration between doses (e.g. a high concentration relative to other previously disclosed p38 MAP kinase inhibitors such as, for example, BIRB796); and/or establish and maintain a relatively high drug concentration in a target tissue following (e.g. topical) administration (e.g. a high concentration relative to other previously disclosed p38 MAP kinase inhibitors such as, for example, BIRB796).

Experimental Methods

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under a balloon of hydrogen. Microwave reactions were performed in a CEM Discover and Smithcreator microwave reactor, heating to a constant temperature using variable power microwave irradiation.

Normal phase column chromatography was routinely carried out on an automated flash chromatography system such as CombiFlash Companion or CombiFlash RF system using pre-packed silica (230-400 mesh, 40-63 μm) cartridges. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Analytical Methods

Analytical HPLC was carried out using an Agilent Zorbax Extend C18, Rapid Resolution HT 1.8 μm column eluting with a gradient of either 0.1% formic acid in MeCN in 0.1% aqueous formic acid or a gradient of MeCN in 10 mM Ammonium Bicarbonate; a Waters Xselect CSH C18 3.5 μm eluting with a gradient of 0.1% formic acid in MeCN in 0.1% aqueous formic acid. UV spectra of the eluted peaks were measured using either a diode array or variable wavelength detector on an Agilent 1100 system.

Analytical LCMS was carried out using an Agilent Zorbax Extend C18, Rapid Resolution HT 1.8 μm column eluting with a gradient of either 0.1% formic acid in MeCN in 0.1% aqueous formic acid or a gradient of MeCN in 10 mM Ammonium Bicarbonate; a Waters Xselect CSH C18 3.5 μm eluting with a gradient of 0.1% formic acid in MeCN in 0.1% aqueous formic acid. UV and mass spectra of the eluted peaks were measured using a variable wavelength detector on either an Agilent 1100 with or an Agilent Infinity 1260 LC with 6120 quadrupole mass spectrometer with positive and negative ion electrospray.

Preparative HPLC was carried out using an Agilent Prep-C18 5 μm Preparative Cartridge using either a gradient of either 0.1% formic acid in MeCN in 0.1% aqueous formic acid or a gradient of MeCN in 10 mM Ammonium Bicarbonate; or a Waters Xselect CSH C18 5 μm column using a gradient 0.1% MeCN in 0.1% aqueous formic acid. Fractions were collected following detection by UV at 254 nm.

$^1$H NMR Spectroscopy:

$^1$H NMR spectra were acquired on a Bruker Avance III spectrometer at 400 MHz. Either the central peaks of chloroform-d, dimethylsulfoxide-$d_6$ or an internal standard of tetramethylsilane were used as references.

PREPARATION OF COMPOUNDS OF THE INVENTION

Example 1

3-((4-((4-(3-(3-(tert-Butyl)-1-methyl-1H-pyrazol-5-yl)ureido)naphthalen-1-yl)oxy)pyrimidin-2-yl)amino)-5-ethynyl-N-(2-morpholinoethyl)benzamide

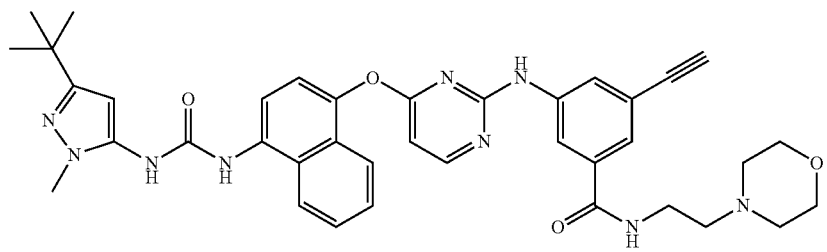 [SMILES: C#Cc1cc(Nc2nccc(Oc3ccc(NC(=O)Nc4cc(C(C)(C)C)nn4C)c4ccccc34)n2)cc(C(=O)NCCN2CCOCC2)c1]

(i) 3-Amino-5-bromo-N-(2-morpholinoethyl)benzamide

T3P (50% w/w in EtOAc, 56.2 ml, 94 mmol), was added carefully to a solution of 3-amino-5-bromobenzoic acid (13.6 g, 63.0 mmol), 2-morpholineethanamine (16.52 mL, 126 mmol) and $Et_3N$ (26.3 mL, 189 mmol) in DCM (200 mL). An ice bath was used sporadically to prevent temperature rising above 35° C. Reaction stirred at room temperature for 1 h. Partitioned with sat. aq. $NaHCO_3$ solution (250 mL). Aqueous separated and partitioned with fresh DCM (250 mL). Organics separated, bulked and partitioned with 20% w/w NaCl solution (250 mL). The organic layer was separated, dried ($MgSO_4$), filtered and solvent evaporated. The crude product was dissolved in DCM (100 mL) and the sub-title compound (13 g) crystallised out on standing as a light tan crystalline solid.

$^1$H NMR (400 MHz, DMSO-d6) δ 8.29 (t, 1H), 7.06 (t, 1H), 6.98 (t, 1H), 6.85 (t, 1H), 5.59 (s, 2H), 3.57 (t, 4H), 3.41-3.26 (m, 2H), 2.48-2.33 (m, 6H).

LCMS m/z 328/330 (M+H)$^+$ (ES$^+$)

(ii) 3-Amino-N-(2-morpholinoethyl)-5-((triisopropylsilyl)ethynyl)benzamide $Pd(PPh_3)_4$ (2.90 g, 2.51 mmol) was added to a degassed suspension of the compound from step (i) above (16.5 g, 50.3 mmol), CuI (0.479 g, 2.51 mmol), and ethynyltriisopropylsilane (16.92 mL, 75 mmol) in Et$_3$N (30 mL) and DMF (150 mL). Reaction heated at 85° C. (block temp.) for 5 h then cooled and filtered (Whatman glass fibre pad GF/C). Solvents evaporated and the residue partitioned between EtOAc (500 mL) and 20% w/w NaCl solution (500 mL). Aqueous layer separated and washed with fresh EtOAc (500 mL). Organic layers bulked, washed with fresh 20% w/w NaCl solution (500 mL), dried (MgSO$_4$), filtered and solvent evaporated to a thick brown oil. The crude product was purified by chromatography on silica gel (220 g column, 2% MeOH:DCM to 10%) to afford the sub-title compound (18.5 g) as a pale yellow glass.

$^1$H NMR (400 MHz, DMSO-d6) δ 8.29 (t, 1H), 7.04 (dd, 1H), 7.02 (t, 1H), 6.79 (dd, 1H), 5.44 (s, 2H), 3.57 (t, 4H), 3.37-3.28 (m, 2H), 2.47-2.36 (m, 6H), 1.11 (s, 21H). LCMS m/z 430 (M+H)$^+$ (ES$^+$)

(iii)
3-Amino-5-ethynyl-N-(2-morpholinoethyl)benzamide

The compound from step (ii) above (18.5 g, 43.1 mmol) was dissolved in EtOAc (250 mL) and TBAF (1.0 M in THF, 43.1 mL, 43.1 mmol) added. The reaction was stirred for 1 h, then partitioned between water (500 mL) and ethyl acetate (200 mL). Organic layer was separated, washed with 20% w/w NaCl solution (400 mL), dried (MgSO$_4$), filtered and solvents evaporated. The crude product was slurried in Et$_2$O (100 mL) for 30 minutes, filtered and washed with fresh Et$_2$O (20 mL). The solid was oven dried at 45° C. to afford the sub-title compound (9.2 g).

$^1$H NMR (400 MHz, DMSO-d6) δ 8.28 (t, 1H), 7.12-6.97 (m, 2H), 6.76 (t, 1H), 5.45 (s, 2H), 4.08 (s, 1H), 3.57 (t, 4H), 3.41-3.25 (m, 2H), 2.48-2.32 (m, 6H).
LCMS m/z 274 (M+H)$^+$ (ES$^+$)

(iv) tert-Butyl (4-((2-((3-ethynyl-5-((2-morpholinoethyl)carbamoyl)phenyl)amino)pyrimidin-4-yl)oxy) naphthalen-1-yl)carbamate A solution of tert-butyl (4-((2-chloropyrimidin-4-yl)oxy) naphthalen-1-yl)carbamate (see, for example, Ito, K. et al., WO 2010/067130, 17 Jun. 2010; 6.46 g, 17.37 mmol), the compound from step (iii) above (7.12 g, 26.0 mmol) and p-TSA monohydrate (5.62 g, 29.5 mmol) in DMF (60 mL) was heated at 55° C. (internal temperature) for 7 h. The mixture was cooled and added dropwise to sat. aq. NaHCO$_3$ (1 L). Solid filtered and washed with water (50 mL) then isohexane (100 mL). The amorphous solid was stirred in MeOH (200 mL) and product crystallised. Slurried overnight, filtered and the solid washed with MeOH (20 mL) and dried to give the sub-title compound (9 g).

$^1$H NMR (400 MHz, DMSO-d6) δ 9.76 (s, 1H), 9.32 (s, 1H), 8.45 (d, 1H), 8.41-8.33 (m, 1H), 8.16-8.03 (m, 2H), 7.90 (t, 1H), 7.85-7.78 (m, 1H), 7.67-7.51 (m, 3H), 7.48-7.37 (m, 2H), 6.58 (d, 1H), 4.16 (s, 1H), 3.56 (t, 4H), 3.46-3.27 (m, 2H), 2.49-2.30 (m, 6H), 1.52 (s, 9H).
LCMS m/z 609 (M+H)$^+$ (ES$^+$)

(v) 3-((4-((4-Aminonaphthalen-1-yl)oxy)pyrimidin-2-yl)amino)-5-ethynyl-N-(2-morpholino ethyl)benzamide TFA (22 mL, 286 mmol) was added dropwise to a stirred solution of the compound from step (iv) above (9 g, 14.05 mmol) in DCM (50 mL). The reaction was stirred at room temperature for 2 h. The mixture was added dropwise to stirred water (100 mL) and 1.0 M K$_2$O$_3$ solution (280 mL, 280 mmol) and stirring continued until effervescence ceased. The mixture was extracted with DCM (2×250 mL) then the combined organic phases were dried (MgSO$_4$) and concentrated under reduced pressure. The crude product was purified by chromatography on the Companion (120 g column, 2% MeOH:DCM to 6%) to afford the sub-title compound (6.7 g) as a pale brown foam.

$^1$H NMR (400 MHz, DMSO-d6) δ 9.77 (s, 1H), 8.39 (t, 1H), 8.36 (d, 1H), 8.17-8.10 (m, 1H), 8.06 (s, 1H), 7.94 (dd, 1H), 7.67-7.59 (m, 1H), 7.49-7.38 (m, 3H), 7.15 (d, 1H), 6.70 (d, 1H), 6.37 (d, 1H), 5.79 (s, 2H), 4.20 (s, 1H), 3.56 (t, 4H), 3.41-3.30 (m, 2H), 2.48-2.34 (m, 6H)
LCMS m/z 509 (M+H)$^+$ (ES$^+$)

(vi) Phenyl (3-(tert-butyl)-1-methyl-1H-pyrazol-5-yl)carbamate

Phenyl chloroformate (0.8 mL, 6.38 mmol) was added to a stirred solution of 3-(tert-butyl)-1-methyl-1H-pyrazol-5-amine (0.93 g, 6.07 mmol) and sodium bicarbonate (1.1 g, 13.09 mmol) in THF (10 mL) and DCM (10 mL) and stirring continued for 2 h. The mixture was washed with water (20 mL) and the organic layer separated, dried (MgSO$_4$), filtered and evaporated to a colourless foam which was stirred in cyclohexane (20 mL) to give the sub-title compound (1.5 g) as a colourless solid.

$^1$H NMR (400 MHz, DMSO-d6) δ 10.12 (s, 1H), 7.44 (t, 2H), 7.35-7.14 (m, 3H), 6.05 (s, 1H), 3.66 (s, 3H), 1.21 (s, 9H).
LCMS m/z 274 (M+H)$^+$ (ES$^+$)

(vii) 3-((4-((4-(3-(3-(tert-Butyl)-1-methyl-1H-pyrazol-5-yl)ureido)naphthalen-1-yl)oxy)-pyrimidin-2-yl)amino)-5-ethynyl-N-(2-morpholinoethyl)benzamide Triethylamine (5 μL, 0.036 mmol) was added to a mixture of the compound from step (vi) above (50 mg, 0.183 mmol) and the compound from step (v) above (95 mg, 0.187 mmol) in iPrOAc (3 mL) and the mixture heated at 50° C. (block temperature) for 6 h. The reaction was cooled to room temperature and left stirring for 72 h. The resulting solid was filtered off, washed with iPrOAc (1 mL) and dried to give the title compound (102 mg) as a colourless solid.

$^1$H NMR (400 MHz, DMSO-d6) δ 9.76 (s, 1H), 8.99 (s, 1H), 8.85 (s, 1H), 8.44 (d, 1H), 8.35 (t, 1H), 8.18 (d, 1H), 8.10-8.03 (m, 1H), 7.99 (d, 1H), 7.91-7.80 (m, 2H), 7.75-7.64 (m, 1H), 7.64-7.54 (m, 1H), 7.50-7.34 (m, 2H), 6.57 (d, 1H), 6.12 (s, 1H), 4.12 (s, 1H), 3.69 (s, 3H), 3.63-3.47 (m, 4H), 3.42-3.33 (m, 2H), 2.48-2.31 (m, 6H), 1.23 (s, 9H).
LCMS m/z 688 (M+H)$^+$ (ES$^+$)

Example 2

1-(3-(tert-Butyl)-1-methyl-1H-pyrazol-5-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea

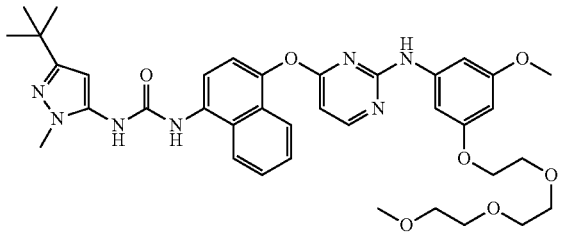 [SMILES: COCCOCCOCCOc1cc(Nc2nccc(Oc3ccc(NC(=O)Nc4cc(C(C)(C)C)nn4C)c4ccccc34)n2)cc(OC)c1]

(i) 3-Methoxy-5-nitrophenol

A mixture of KOH (29.0 g, 517 mmol) and 1-bromo-3-methoxy-5-nitrobenzene (30 g, 129 mmol) in water (70 mL) and dioxane (70 mL) was degassed for 5 minutes prior to the addition of di-tert-butyl(2',4',6'-triisopropyl-[1,1'-biphenyl]-2-yl)phosphine (1.263 g, 2.97 mmol) and Pd$_2$(dba)$_3$ (1.184 g, 1.293 mmol). The resulting mixture was degassed for a further 2 minutes then heated under a nitrogen atmosphere at 100° C. for 2 h. The mixture was cooled, then acidified with 5 M HCl to ~pH 1 and extracted with EtOAc (2×500 mL). The organic layer was washed with saturated brine (200 mL), dried (MgSO$_4$), filtered and concentrated under reduced pressure. The crude product was purified through a pad of silica eluting with 30% EtOAc/isohexane to afford the sub-title compound (20.76 g) as a yellow solid.

$^1$H NMR (400 MHz; DMSO-d6) δ 10.46 (s, 1H), 7.20 (s, 1H), 7.19 (s, 1H), 6.76 (s, 1H), 3.82 (s, 3H).

LCMS m/z 168 (M−H)$^−$ (ES$^−$)

(ii) 1-Methoxy-3-(2-(2-(2-methoxyethoxy)ethoxy)ethoxy)-5-nitrobenzene

To a stirred suspension of the product from step (i) above (8.14 g, 45.7 mmol) and K$_2$CO$_3$ (12.64 g, 91 mmol) in acetone (150 mL) was added 1-bromo-2-(2-(2-methoxy-ethoxy)ethoxy)ethane (8.85 mL, 48.0 mmol). The resulting mixture was refluxed overnight, cooled and filtered. The filtrate was evaporated under reduced pressure and the residue purified by chromatography on silica gel (220 g column, 0-60% EtOAc/isohexane) to afford the sub-title compound (13.41 g) as a yellow oil.

$^1$H NMR (DMSO-d6) 400 MHz, δ: 7.34-7.32 (m, 2H), 6.98 (t, 1H), 4.22-4.20 (m, 2H), 3.85 (s, 3H), 3.77-3.74 (m, 2H), 3.60-3.57 (m, 2H), 3.54-3.50 (m, 4H), 3.44-3.40 (m, 2H), 3.23 (s, 3H)

LCMS m/z 316 (M+H)$^+$ (ES$^+$)

(iii) 3-Methoxy-5-(2-(2-(2-methoxyethoxy)ethoxy)ethoxy)aniline

The product from step (ii) above (13.4 g, 42.5 mmol) was dissolved in ethanol (150 mL) and Fe powder (13 g, 233 mmol) was added followed by a solution of NH$_4$Cl (2.3 g, 43.0 mmol) in water (150 mL). The resulting suspension was heated at 80° C. for 3 h. The reaction was cooled to room temperature and filtered through Celite. The filtrate was concentrated in vacuo then partitioned between water (250 mL) and EtOAc (400 mL). The organic layer was separated, dried (MgSO$_4$), filtered and concentrated under reduced pressure. The crude product was purified by chromatography on silica gel (120 g column, 0-4% MeOH/DCM) to afford the sub-title compound (10.95 g) as an oil.

$^1$H NMR (400 MHz, DMSO-d6) δ 5.76-5.73 (m, 2H), 5.68 (t, 1H), 5.07 (s, 2H), 3.98-3.89 (m, 2H), 3.72-3.65 (m, 2H), 3.63 (s, 3H), 3.60-3.48 (m, 6H), 3.47-3.40 (m, 2H), 3.24 (s, 3H)

LCMS m/z 286 (M+H)$^+$ (ES$^+$)

(iv) tert-Butyl (4-((2-((3-methoxy-5-(2-(2-(2-methoxyethoxy)ethoxy)ethoxy)phenyl)amino)-pyrimidin-4-yl)oxy)naphthalen-1-yl)carbamate tert-Butyl (4-((2-chloropyrimidin-4-yl)oxy)naphthalen-1-yl)carbamate (see, for example, Ito, K. et al., WO 2010/067130, 17 Jun. 2010; 1 g, 2.69 mmol), the product of step (iii) above (1.15 g, 4.03 mmol) and p-TSA monohydrate (0.100 g, 0.526 mmol) in DMF (10 mL) was heated at 55° C. (internal temperature) for 14 h. The mixture was cooled and added dropwise to sat. aq. NaHCO$_3$ (100 mL) then partitioned with EtOAc (2×50 mL). Organics were bulked and washed with 20% w/w NaCl solution (50 mL), then dried (MgSO$_4$), filtered and solvent evaporated. The crude product was purified by chromatography on silica gel (40 g column) to afford the sub-title compound (1.14 g) as a clear brown oil.

$^1$H NMR (400 MHz, DMSO-d6) δ 9.44 (s, 1H), 9.34 (s, 1H), 8.42 (d, 1H), 8.11 (d, 1H), 7.86-7.76 (m, 1H), 7.66-7.49 (m, 3H), 7.39 (d, 1H), 6.85 (s, 2H), 6.56 (d, 1H), 6.05 (t, 1H), 3.88 (dd, 2H), 3.71-3.63 (m, 2H), 3.59-3.48 (m, 9H), 3.46-3.38 (m, 2H), 3.22 (s, 3H), 1.52 (s, 9H)

LCMS m/z 621 (M+H)$^+$ (ES$^+$)

(v) 4-((4-Aminonaphthalen-1-yl)oxy)-N-(3-methoxy-5-(2-(2-(2-methoxyethoxy)ethoxy)-ethoxy)phenyl)pyrimidin-2-amine TFA (2.8 mL, 36.3 mmol) was added dropwise to a stirred solution of the product of step (iv) above (1.1 g, 1.772 mmol) in DCM (5 mL). The reaction was stirred at room temperature for 2 h. The mixture was added dropwise to stirred water (10 mL) and 1 M K$_2$CO$_3$ solution (35 mL, 35.0 mmol) and stirring continued until effervescence ceased. The mixture was extracted with DCM (2×25 mL) then the combined organic phases were dried (MgSO$_4$) and concentrated under reduced pressure. The crude product was purified by chromatography on silica gel (40 g column, 2% MeOH:DCM to 5%) to afford a brown gum. Recrystallised from iPrOAc (3 mL) afforded the sub-title compound (0.80 g) as a colourless solid.

$^1$H NMR (400 MHz, DMSO-d6) δ 9.42 (s, 1H), 8.33 (d, 1H), 8.22-8.03 (m, 1H), 7.69-7.56 (m, 1H), 7.51-7.35 (m, 2H), 7.11 (d, 1H), 6.87 (d, 2H), 6.68 (d, 1H), 6.35 (d, 1H), 6.04 (t, 1H), 5.79 (s, 2H), 3.94-3.78 (m, 2H), 3.74-3.64 (m, 2H), 3.60-3.47 (m, 9H), 3.46-3.38 (m, 2H), 3.22 (s, 3H)

LCMS m/z 521 (M+H)$^+$ (ES$^+$)

(vi) 1-(3-(tert-Butyl)-1-methyl-1H-pyrazol-5-yl)-3-(4-((2-((3-methoxy-5-(2-(2-(2-methoxy-ethoxy)ethoxy)phenyl)amino)pyrimidin-4-yl)oxy)naphthalen-1-yl)urea Triethylamine (5 µL, 0.036 mmol) was added to a mixture of phenyl (3-(tert-butyl)-1-methyl-1H-pyrazol-5-yl)carbamate (see Example 1(vi) above; 50 mg, 0.183 mmol) and the product from step (v) above (95 mg, 0.182 mmol) in iPrOAc (3 mL) and the mixture heated at 50° C. (block temperature) for 6 h during which time a thick gel-like precipitate formed. The reaction was cooled to room temperature and the solid isolated by filtration, washing with iPrOAc. The material was further purified by column chromatography on the Companion (12 g column, 1-5% MeOH in DCM) to afford the title compound (48 mg) as a white, glassy solid.

$^1$H NMR (400 MHz, DMSO-d6) δ: 9.43 (s, 1H), 9.01 (s, 1H), 8.87 (s, 1H), 8.42 (d, 1H), 8.18 (d, 1H), 8.01 (d, 1H), 7.85 (d, 1H), 7.68 (t, 1H), 7.59 (t, 1H), 7.41 (d, 1H), 6.82 (d, 2H), 6.54 (d, 1H), 6.12 (s, 1H), 6.04 (s, 1H), 3.87 (t, 2H), 3.69 (s, 3H), 3.66 (t, 2H), 3.49-3.56 (m, 9H), 3.42 (dd, 2H), 3.22 (s, 3H), 1.23 (s, 9H).

LCMS m/z 351 (M+2H)$^{2+}$ (ES$^+$)

Example 3

1-(3-(tert-Butyl)-1-methyl-1H-pyrazol-5-yl)-3-(4-((2-((3-(cyclopropylsulfonyl)-5-methoxy-phenyl)amino)pyrimidin-4-yl)oxy)naphthalen-1-yl)urea

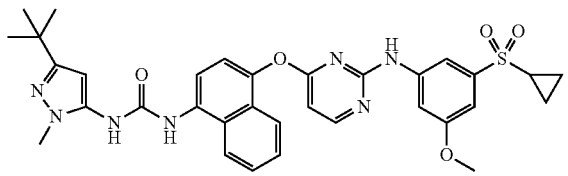 [SMILES: COc1cc(Nc2nccc(Oc3ccc(NC(=O)Nc4cc(C(C)(C)C)nn4C)c4ccccc34)n2)cc(S(=O)(=O)C2CC2)c1]

(i) 1-(Cyclopropylsulfonyl)-3-methoxy-5-nitrobenzene

A mixture of 1-bromo-3-methoxy-5-nitrobenzene (9.05 g, 39.0 mmol), sodium cyclopropanesulfinate (6.5 g, 50.7 mmol), copper(I) iodide (0.743 g, 3.90 mmol), L-proline (0.908 g, 7.88 mmol) and NaOH (0.315 g, 7.88 mmol) in DMSO (50 mL) was heated at 90° C. for 18 h and 100° C. for 12 h. The mixture was partitioned between EtOAc (500 mL) and water (300 mL), the organic layer separated, washed with brine (200 mL), dried (MgSO$_4$), filtered and evaporated under reduced pressure. The crude product was purified by chromatography on silica gel (120 g column, 0-40% EtOAc/isohexane) to afford the sub-title compound (4.226 g) as a solid.

$^1$H NMR (400 MHz; DMSO-d6) δ 8.31 (s, 1H), 7.97 (s, 1H), 7.73 (s, 1H), 3.98 (s, 3H), 2.55-2.49 (m, 1H), 1.48-1.36 (m, 2H), 1.15-1.10 (m, 2H).

(ii) 3-(Cyclopropylsulfonyl)-5-methoxyaniline

A mixture of the product from step (i) above (4.22 g, 16.40 mmol), Fe powder (4.3 g, 77 mmol) and NH$_4$Cl (0.439 g, 8.20 mmol) in EtOH (40 mL) and water (20 mL) was heated under reflux for 1 h. The mixture was cooled, diluted with EtOH (50 mL) and filtered through celite. The filtrate was evaporated, partitioned between EtOAc (300 mL) and brine (200 mL), the organic layer separated, dried (MgSO$_4$), filtered, and evaporated under reduced pressure. The residue was triturated with ether and filtered to afford the sub-title compound (3.308 g).

LCMS m/z 228 (M+H)$^+$ (ES$^+$)

(iii) tert-Butyl (4-((2-((3-(cyclopropylsulfonyl)-5-methoxyphenyl)amino)pyrimidin-4-yl)oxy)-naphthalen-1-yl)carbamate A mixture of tert-butyl (4-((2-chloropyrimidin-4-yl)oxy)naphthalen-1-yl)carbamate (see, for example, Ito, K. et al., WO 2010/067130, 17 Jun. 2010; 2.92 g, 7.86 mmol), the product from step (ii) above (2.5 g, 11.00 mmol) and p-TSA monohydrate (0.3 g, 1.577 mmol) in THF (40 mL) was heated at 55° C. for 4 h. The mixture was cooled, partitioned between EtOAc (150 mL) and water (100 mL), the organic layer separated, washed with brine (50 mL), dried (MgSO$_4$), filtered and evaporated under reduced pressure. The crude product was purified by chromatography on silica gel (120 g column, 0-50% EtOAc/isohexane) to give a solid which was recrystallised from ether to afford the sub-title compound (3.8 g) as a white solid.

LCMS m/z 563 (M+H)$^+$ (ES$^+$)

(iv) 4-((4-Aminonaphthalen-1-yl)oxy)-N-(3-(cyclopropylsulfonyl)-5-methoxyphenyl)-pyrimidin-2-amine A mixture of the product from step (iii) above (3.8 g, 6.75 mmol) and TFA (3 mL, 38.9 mmol) in DCM (50 mL) was stirred at room temperature for 18 h. A further 5 mL of TFA was added and stirred for a further 2 h. The solvent was evaporated under reduced pressure and the residue partitioned between DCM (150 mL) and sat. aq. NaHCO$_3$ solution (150 mL). The organic layer was separated, washed with brine, dried (MgSO$_4$), filtered and evaporated under reduced pressure. The crude product was purified by chromatography on silica gel (120 g column, 0-2% MeOH/DCM) to afford a foam which was recrystallised from DCM/ether to afford the sub-title compound (2.332 g) as a solid.

$^1$H NMR (400 MHz; CDCl$_3$) δ 8.29 (d, 1H), 7.87-7.81 (m, 2H), 7.52-7.45 (m, 4H), 7.22 (s, 1H), 7.11 (d, 1H), 6.97 (s, 1H), 6.78 (d, 1H), 6.38 (d, 1H), 4.18 (s, 2H), 3.68 (s, 3H), 2.42-2.36 (m, 1H), 1.32-1.28 (m, 2H), 1.01-0.96 (m, 2H).

LCMS m/z 463 (M+H)$^+$ (ES$^+$); 461 (M−H)$^-$ (ES$^-$)

(v) 1-(3-(tert-Butyl)-1-methyl-1H-pyrazol-5-yl)-3-(4-((2-((3-(cyclopropylsulfonyl)-5-methoxyphenyl)amino)pyrimidin-4-yl)oxy)naphthalen-1-yl)urea Triethylamine (6.00 μL, 0.043 mmol) was added to a mixture of phenyl (3-(tert-butyl)-1-methyl-1H-pyrazol-5-yl)carbamate (see Example 1(vi) above; 60 mg, 0.220 mmol) and the product from step (iv) above (100 mg, 0.216 mmol) in iPrOAc (3 mL) and the mixture heated at 50° C. (block temperature) for 6 h during which time a thick gel-like precipitate formed. The reaction was cooled to room temperature and the solid isolated by filtration, washing with further iPrOAc to afford the title compound (82 mg) as a solid.

$^1$H NMR (400 MHz, DMSO-d6) δ: 9.85 (s, 1H), 9.02 (s, 1H), 8.88 (s, 1H), 8.48 (d, 1H), 8.19 (d, 1H), 8.02 (d, 1H), 7.85 (d, 1H), 7.74 (s, 1H), 7.69 (t, 1H), 7.60 (t, 1H), 7.52 (s, 1H), 7.43 (d, 1H), 6.87 (s, 1H), 6.64 (d, 1H), 6.13 (s, 1H), 3.65 (s, 3H), 3.32 (s, 3H), 2.70-2.76 (m, 1H), 1.24 (s, 9H), 0.99-1.09 (m, 4H).

LCMS m/z 322 (M+2H)$^{2+}$ (ES$^+$)

Example 4

3-((4-((4-(3-(3-(tert-Butyl)-1-methyl-1H-pyrazol-5-yl)ureido)naphthalen-1-yl)oxy)pyrimidin-2-yl)amino)-5-ethynyl-N-(2-(2-methoxyethoxy)ethyl)

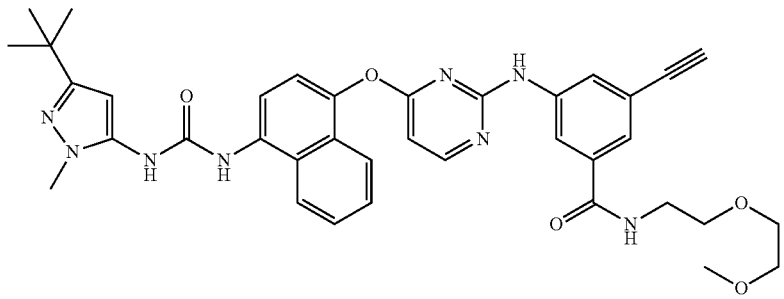 [SMILES: C#Cc1cc(Nc2nccc(Oc3ccc(NC(=O)Nc4cc(C(C)(C)C)nn4C)c4ccccc34)n2)cc(C(=O)NCCOCCOC)c1]

(i) 3-Amino-5-bromo-N-(2-(2-methoxyethoxy)ethyl)benzamide

A stirred mixture of 3-amino-5-bromobenzoic acid (800 mg, 3.59 mmol), 2-(2-methoxyethoxy)ethanamine (856 mg, 7.18 mmol) and Et$_3$N (1.5 mL, 10.76 mmol) in DCM (13 mL) was cooled in an ice bath. T3P (50 w/w in EtOAc, 3.2 mL, 5.38 mmol) was added dropwise, the ice bath was removed and the reaction mixture allowed to warm to room temperature. DMF (2 mL) was added to aid solubility and the reaction stirred at room temperature overnight. The reaction mixture was partitioned between sat. aq. NaHCO$_3$ (50 mL) and DCM (50 mL). The aqueous phase was back extracted with fresh DCM (50 mL). The combined organic extracts were washed with water (100 mL), brine (100 mL), dried (MgSO$_4$), filtered and concentrated in vacuo to afford an orange oil. The crude product was purified by chromatography on silica gel (40 g column, 0-5% MeOH) to afford the sub-title compound (880 mg) as an orange oil.

$^1$H NMR (DMSO-d6) 400 MHz, δ: 8.36 (t, 1H), 7.07 (t, 1H), 7.00-6.99 (m, 1H), 6.84 (t, 1H), 5.57 (s, 2H), 3.53-3.48 (m, 4H), 3.44-3.42 (m, 2H), 3.35 (q, 2H), 3.23 (s, 3H).

LCMS m/z 317/319 (M+H)$^+$ (ES$^+$)

(ii) 3-Amino-N-(2-(2-methoxyethoxy)ethyl)-5-((triisopropylsilyl)ethynyl)benzamide To a degassed solution of the product from step (i) above (830 mg, 2.59 mmol), ethynyltriisopropylsilane (880 μL, 3.92 mmol), copper(I) iodide (24.67 mg, 0.130 mmol) and Et$_3$N (1.55 mL, 11.12 mmol) in DMF (8 mL) was added Pd(PPh$_3$)$_4$ (150 mg, 0.130 mmol). The reaction was heated at 85° C. for 3 h. The reaction was cooled to room temperature then partitioned between EtOAc (50 mL) and brine (50 mL). The aqueous phase was back extracted with EtOAc (50 mL). The combined organic extracts were washed with brine (100 mL), dried (MgSO$_4$), filtered and concentrated in vacuo to afford a brown semi-solid (1.65 g). The crude product was purified by chromatography on silica gel (80 g column, 0-3% MeOH in DCM) to afford the sub-title compound (796 mg) as a beige solid.

$^1$H NMR (DMSO-d6) 400 MHz, δ: 8.39 (t, 1H), 7.05-7.04 (m, 1H), 7.03 (t, 1H), 6.79-6.78 (m, 1H), 5.44 (br s, 2H), 3.53-3.48 (m, 4H), 3.44-3.42 (m, 2H), 3.35 (q, 2H), 3.23 (s, 3H), 1.10 (s, 21H).

LCMS m/z 419 (M+H)$^+$ (ES$^+$)

(iii) 3-Amino-5-ethynyl-N-(2-(2-methoxyethoxy)ethyl)benzamide

To a stirred solution of the product from step (ii) above (717 mg, 1.473 mmol) in EtOAc (9 mL) was added TBAF (1.0 M in THF, 1473 μL, 1.473 mmol). The reaction was stirred at room temperature for 1 h. The reaction mixture was partitioned between water (30 mL) and EtOAc (20 mL). The organic layer was washed with brine (20 mL), dried (MgSO$_4$), filtered and concentrated to afford a brown oil. The crude product was dissolved in the minimum quantity of MeOH and loaded onto SCX. The column was eluted with MeOH followed by 1% NH$_3$ in MeOH. The filtrate was concentrated in vacuo to afford a brown oil at ~70% purity. The crude product was purified by chromatography on silica gel (40 g column, 0-5% MeOH in DCM) to afford the sub-title compound (377 mg) as an orange oil.

$^1$H NMR (DMSO-d6) 400 MHz, δ: 8.36 (t, 1H), 7.06-7.04 (m, 2H), 6.75-6.74 (m, 1H), 5.45 (s, 2H), 4.07 (s, 1H), 3.53-3.47 (m, 4H), 3.44-3.42 (m, 2H), 3.37-3.33 (m, 2H), 3.23 (s, 3H).

LCMS m/z 263 (M+H)$^+$ (ES$^+$)

(iv) 4-((2-Chloropyrimidin-4-yl)oxy)naphthalen-1-amine

A solution of tert-butyl (4-((2-chloropyrimidin-4-yl)oxy)naphthalen-1-yl)carbamate (see, for example, Ito, K. et al., WO 2010/067130, 17 Jun. 2010; 5 g, 13.45 mmol) in DCM (100 mL) was treated dropwise with TFA (41 mL, 532 mmol). The resultant brown solution was stirred at room temperature for 3 h and 20 min, then concentrated in vacuo and the residue partitioned between saturated NaHCO$_3$ solution (200 mL) and EtOAc (200 mL). The organic phase was washed with saturated NaHCO$_3$ solution (2×50 mL), water (2×50 mL), and saturated brine (50 mL). The organic phase was dried (Na$_2$SO$_4$), filtered and concentrated in vacuo to afford the sub-title compound (3.27 g) as a brown solid.

$^1$H NMR (400 MHz, DMSO-d6) δ 8.57 (d, 1H), 8.20-8.14 (m, 1H), 7.61-7.54 (m, 1H), 7.45 (dt, 2H), 7.14 (d, 1H), 7.05 (d, 1H), 6.69 (d, 1H), 5.90 (s, 2H)

LCMS m/z 272 (M+H)$^+$ (ES$^+$)

(v) 1-(3-(tert-Butyl)-1-methyl-1H-pyrazol-5-yl)-3-(4-((2-chloropyrimidin-4-yl)oxy)-naphthalen-1-yl)urea Triethylamine (25 μL, 0.179 mmol) was added to a stirred mixture of phenyl (3-(tert-butyl)-1-methyl-1H-pyrazol-5-yl)

carbamate (see Example 1(vi) above; 250 mg, 0.905 mmol) and the product from step (iv) above (259 mg, 0.905 mmol) in iPrOAc (10 mL). The resulting mixture was heated at 70° C. for 2 h. The reaction was cooled to room temperature and the solvent removed in vacuo. The crude product was purified by chromatography on silica gel (80 g column, 0-10% MeOH in DCM) to afford the sub-title compound (238 mg) as a pale pink solid.

$^1$H NMR (400 MHz, DMSO-d6) δ: 9.11 (s, 1H), 8.99 (d, 1H), 8.66 (d, 1H), 8.23 (d, 1H), 8.01 (d, 1H), 7.81 (d, 1H), 7.72-7.68 (m, 1H), 7.62-7.58 (m, 1H), 7.44 (d, 1H), 7.27 (d, 1H), 6.13 (s, 1H), 3.69 (s, 3H), 1.23 (s, 9H).

LCMS m/z 451 (M+H)$^+$ (ES$^+$)

(vi) 3-((4-((4-(3-(3-(tert-Butyl)-1-methyl-1H-pyrazol-5-yl)ureido)naphthalen-1-yl)oxy)-pyrimidin-2-yl)amino)-5-ethynyl-N-(2-(2-methoxyethoxy)ethyl) benzamide The product from step (v) above (100 mg, 0.222 mmol) was dissolved in DMF (2 mL) then the product from step (iii) above (70 mg, 0.267 mmol) and p-TSA monohydrate (10 mg, 0.053 mmol) added and the mixture stirred at 50° C. (block temperature) for 16 h. The mixture was poured into sat. aq. NaHCO₃ solution (10 mL) and the product extracted with EtOAc (2×10 mL). The organic phase was washed with 20% w/w NaCl solution (20 ml), separated, dried (MgSO₄), filtered and evaporated. The crude product was purified by chromatography on silica gel (12 g column, 2% MeOH: DCM to 100%) then recrystallised from MeCN (3 mL) and stirred in Et₂O to give the title compound (49 mg) as a solid.

$^1$H NMR (400 MHz, DMSO-d6) δ 9.76 (s, 1H), 8.99 (s, 1H), 8.85 (s, 1H), 8.54-8.37 (m, 2H), 8.18 (d, 1H), 8.11-8.04 (m, 1H), 7.99 (d, 1H), 7.93-7.80 (m, 2H), 7.73-7.63 (m, 1H), 7.63-7.55 (m, 1H), 7.51-7.34 (m, 2H), 6.56 (d, 1H), 6.12 (s, 1H), 4.12 (s, 1H), 3.69 (s, 3H), 3.58-3.47 (m, 4H), 3.47-3.35 (m, 4H), 3.23 (s, 3H), 1.24 (s, 9H).

LCMS m/z 677 (M+H)$^+$ (ES$^+$); 675 (M-H)$^-$ (ES$^-$)

Example 5

1-(3-(tert-Butyl)-1-methyl-1H-pyrazol-5-yl)-3-(4-((2-((3-methoxy-5-(2-(2-(2-methoxy-ethoxy)ethoxy)ethoxy)phenyl)amino)pyridin-4-yl)oxy)naphthalen-1-yl)

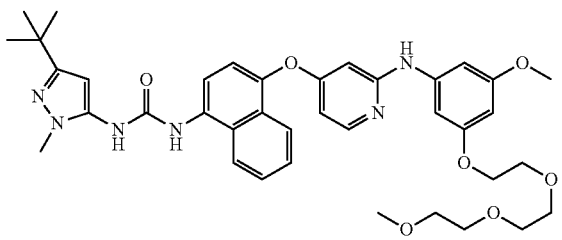 [SMILES: COCCOCCOCCOc1cc(Nc2cc(Oc3ccc(NC(=O)Nc4cc(C(C)(C)C)nn4C)c4ccccc34)ccn2)cc(OC)c1]

(i) 4-((2-Chloropyridin-4-yl)oxy)naphthalen-1-amine

KOtBu (25.8 g, 230 mmol) was added portionwise to a stirred mixture of 4-aminonaphthalen-1-ol hydrochloride (15 g, 77 mmol) in DMF (250 mL) at −20° C. under N₂. The mixture was stirred for 20 min then 2-chloro-4-fluoropyridine (10.4 mL, 115 mmol) was added and the mixture warmed to 0-5° C. After stirring for 2 h, activated charcoal (20 g) was added, stirred for 30 min then filtered. The filtrate was partitioned between ether (400 mL) and water (400 mL), the ether layer was separated and the aqueous layer washed with ether (300 mL). The combined ether layers were washed with water (200 mL), dried (MgSO₄) and activated charcoal (15 g) added. The mixture was stirred for 30 min then filtered and evaporated under reduced pressure. The residue was triturated with ether (100 mL), filtered and washed with ether (3×50 mL) to afford the sub-title compound (5.44 g).

$^1$H NMR (400 MHz; CDCl₃) δ 8.18 (d, 1H), 7.88 (d, 1H), 7.77 (d, 1H), 7.56-7.46 (m, 2H), 7.05 (d, 1H), 6.79-6.76 (m, 3H), 4.24 (br s, 2H).

LCMS m/z 271 (M+H)$^+$ (ES$^+$)

(ii) tert-Butyl (4-((2-chloropyridin-4-yl)oxy)naphthalen-1-yl)carbamate

A mixture of the product from step (i) above (1000 mg, 3.69 mmol) and di-tert-butyl dicarbonate (750 mg, 3.44 mmol) in t-BuOH (10 mL) was stirred at reflux for 18 h. The mixture was diluted with water (15 mL) and collected by filtration. The solid was triturated in Et₂O to yield the sub-title compound (1002 mg) as a pale grey solid.

$^1$H NMR (DMSO-d₆) 400 MHz, δ: 9.37 (s, 1H), 8.28 (d, 1H), 8.16 (d, 1H), 8.82 (dd, 1H), 7.66 (d, 1H), 7.66-7.54 (m, 2H), 7.40 (d, 1H), 7.03 (d, 1H), 6.91 (dd, 1H), 1.52 (s, 9H).

LCMS m/z 371 (M+H)$^+$ (ES$^+$); 369 (M-H)$^-$ (ES$^-$)

(iii) tert-Butyl (4-((2-((3-methoxy-5-(2-(2-(2-methoxyethoxy)ethoxy)ethoxy)phenyl)amino)-pyridin-4-yl)oxy)naphthalen-1-yl)carbamate Pd₂(dba)₃ (22 mg, 0.024 mmol) and BINAP (30 mg, 0.048 mmol) were stirred in 1,4-dioxane (1 mL) for 10 minutes under N₂. In a separate vessel, purged with N₂, CS₂CO₃ (455 mg, 1.396 mmol), 3-methoxy-5-(2-(2-(2-methoxyethoxy)ethoxy)ethoxy)aniline (265 mg, 0.930 mmol) and the product from step (ii) above (345 mg, 0.930 mmol) were stirred in 1,4-dioxane (5 mL). The catalyst solution was added to the main reaction mixture and the whole was heated to 90° C. for 48 h. Pd₂(dba)₃ (22 mg, 0.024 mmol) and BINAP (30 mg, 0.048 mmol) were added and the mixture was stirred for a further 18 h. Water was added (15 mL) and the mixture was extracted with EtOAc (3×15 mL). The combined organic phases were washed with saturated brine (15 mL), dried (MgSO₄) and concentrated under reduced pressure. The crude product was purified by chromatography on the Companion (40 g column, 50-100% EtOAc/isohexane) to afford the sub-title compound (194 mg) as a sticky brown oil.

$^1$H NMR (DMSO-d₆) 400 MHz, δ: 9.35 (s, 1H), 8.89 (s, 1H), 8.18-8.08 (m, 2H), 7.84 (d, 1H), 7.67-7.52 (m, 3H), 7.35 (d, 1H), 6.91 (s, 1H), 6.79 (s, 1H), 6.58 (dd, 1H), 6.07-6.02 (m, 2H), 4.01-3.95 (m, 2H), 3.74-6.67 (m, 2H), 3.65 (s, 3H), 3.60-3.48 (m, 6H), 3.46-3.39 (m, 2H), 3.23 (s, 3H), 1.52 (s, 9H).

LCMS m/z 620 (M+H)$^+$ (ES$^+$); 618 (M-H)$^-$ (ES$^-$)

(iv) 4-((4-Aminonaphthalen-1-yl)oxy)-N-(3-methoxy-5-(2-(2-(2-methoxyethoxy)ethoxy)-ethoxy)phenyl)pyridin-2-amine A solution of the product from step (iii) above (190 mg, 0.307 mmol) in DCM (0.5 mL) was treated with TFA (500 μL, 6.49 mmol) and stirred at room temperature for 3 h. The mixture was diluted with water (10 mL) and DCM (10 mL).

The mixture was neutralised with sat. aq. NaHCO₃ and passed through a phase separation cartridge. The organic phase was dried (MgSO₄) and concentrated to give the sub-title compound (135 mg) as a brown gum.

¹H NMR (DMSO-d₆) 400 MHz, δ: 8.08 (s, 1H), 8.20-8.10 (m, 1H), 8.05 (d, 1H), 7.67-7.59 (m, 1H), 7.49-7.39 (m, 2H), 7.09 (d, 1H), 6.89 (s, 1H), 6.76 (s, 1H), 6.71 (d, 1H), 6.52 (dd, 1H), 6.06-5.55 (m, 2H), 5.83 (s, 2H), 4.00-3.90 (m, 2H), 3.74-3.66 (m, 2H), 3.64 (s, 3H), 3.60-3.47 (m, 6H), 3.46-3.38 (m, 2H), 3.23 (s, 3H).

LCMS m/z 520 (M+H)⁺ (ES⁺)

(v) 1-(3-(tert-Butyl)-1-methyl-1H-pyrazol-5-yl)-3-(4-((2-((3-methoxy-5-(2-(2-(2-methoxy ethoxy) ethoxy)ethoxy)phenyl)amino)pyridin-4-yl)oxy)naphthalen-1-yl)

Triethylamine (6 µL, 0.043 mmol) was added to a mixture of phenyl (3-(tert-butyl)-1-methyl-1H-pyrazol-5-yl)carbamate (see Example 1(vi) above; 50 mg, 0.183 mmol) and the product from step (iv) above (90 mg, 0.173 mmol) in iPrOAc (3 mL) and the mixture heated at 50° C. (block temperature) for 6 h. The reaction was diluted with EtOAc and concentrated onto silica gel. The material was purified by column chromatography on the Companion (12 g column, 1-5% MeOH in DCM) to afford the product as a pink foam. The material was suspended in Et₂O and the supernatant decanted away. The product was dried at 40° C. under vacuum affording the title compound (86 mg) as a pink solid.

¹H NMR (400 MHz, DMSO-d6) δ: 9.05 (s, 1H), 8.89 (s, 1H), 8.87 (s, 1H), 8.21 (d, 1H), 8.11 (d, 1H), 8.02 (d, 1H), 7.87 (d, 1H), 7.69-7.73 (m, 1H), 7.59-7.63 (m, 1H), 7.38 (d, 1H), 6.90 (s, 1H), 6.78 (s, 1H), 6.58 (dd, 1H), 6.12 (s, 1H), 6.09 (d, 1H), 6.04 (t, 1H), 3.97-3.99 (m, 2H), 3.69-3.72 (m, 2H), 3.68 (s, 3H), 3.66 (s, 3H), 3.56-3.58 (m, 2H), 3.50-3.54 (m, 4H), 3.43 (dd, 2H), 3.23 (s, 3H), 1.23 (s, 9H).

LCMS m/z 350 (M+2H)²⁺ (ES⁺)

Example 6

1-(4-((2-((3-(2,5,8,11,14,17,20-Heptaoxadocosan-22-yloxy)-5-methoxyphenyl)amino)-pyrimidin-4-yl)oxy)naphthalen-1-yl)-3-(3-(tert-butyl)-1-methyl-1H-pyrazol-5-yl)urea

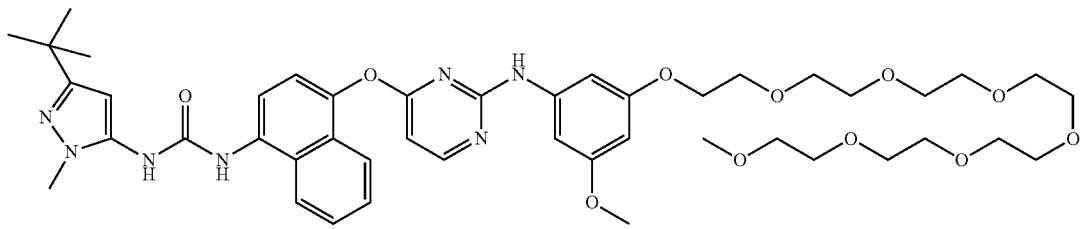 [SMILES: COCCOCCOCCOCCOCCOCCOCCOc1cc(Nc2nccc(Oc3ccc(NC(=O)Nc4cc(C(C)(C)C)nn4C)c4ccccc34)n2)cc(OC)c1]

(i) 2-(3-Methoxy-5-nitrophenoxy)-2,5,8,11,14,17,20-heptaoxadocosane

DIAD (2.76 mL, 14.19 mmol) was added dropwise to a stirred solution of 3-methoxy-5-nitrophenol (2 g, 11.82 mmol), 2,5,8,11,14,17,20-heptaoxadocosan-22-ol (4.03 g, 11.82 mmol) and PPh₃ (3.72 g, 14.19 mmol) in THF (15 mL) at 0-5° C. The mixture was warmed to rt, stirred for 18 h then evaporated under reduced pressure. The crude product was purified by chromatography on silica gel (220 g) column, EtOAc then 0-10% EtOH/EtOAc) to afford the sub-title compound (3.905 g, 70% purity) as an oil.

¹H NMR (400 MHz; CDCl₃) δ 7.38 (s, 1H), 7.36 (s, 1H), 6.78 (s, 1H), 4.19-4.17 (m, 2H), 3.89-3.85 (m, 5H), 3.73-3.62 (m, 22H), 3.56-3.53 (m, 2H), 3.38 (s, 3H).

(ii) 3-(2,5,8,11,14,17,20-Heptaoxadocosan-22-yloxy)-5-methoxyaniline

The product from step (i) above (3.90 g, 5.55 mmol) was dissolved in EtOH (30 mL) and Fe powder (3.10 g, 55.5 mmol) was added followed by a solution of NH₄Cl (2.97 g, 55.5 mmol) in water (15 mL). The resulting suspension was heated at 80° C. for 1 h. The reaction was cooled to rt and filtered. The filtrate was concentrated in vacuo, basified to pH 10 by the addition of sat. aq. NaHCO₃ (80 mL), then extracted with EtOAc (3×100 mL). The combined organic extracts were dried (MgSO₄), filtered and concentrated in vacuo to afford an orange oil (3.7 g). The crude product was dissolved in the minimum of MeOH and loaded onto SCX. The column was eluted first with MeOH (3 column volumes) and then 1% NH₃ in MeOH (3 column volumes). The product-containing fraction was concentrated in vacuo to afford the sub-title compound (2.54 g) as a brown oil.

¹H NMR (400 MHz, DMSO-d6) δ: 5.75-5.74 (m, 2H), 5.68 (t, 1H), 5.04 (s, 2H), 3.95-3.93 (m, 2H), 3.69-3.67 (m, 2H), 3.62 (s, 3H), 3.58-3.49 (m, 22H), 3.43-3.41 (m, 2H), 3.23 (s, 3H).

LCMS m/z 462 (M+H)⁺ (ES⁺)

(iii) tert-Butyl (4-((2-((3-(2,5,8,11,14,17,20-heptaoxadocosan-22-yloxy)-5-methoxyphenyl)amino) pyrimidin-4-yl)oxy)naphthalen-1-yl)carbamate To a stirred solution of tert-butyl (4-((2-chloropyrimidin-4-yl)oxy)naphthalen-1-yl)carbamate (289 mg, 0.701 mmol) and the product from step (ii) above (500 mg, 1.051 mmol) in DMF (20 mL) was added pTSA monohydrate (67 mg, 0.352 mmol). The resulting solution was heated at 60° C. for 48 h. The reaction was cooled to rt and partitioned between EtOAc (80 mL) and sat. aq. NaHCO₃ (50 mL). The aqueous phase was back-extracted with EtOAc (80 mL). The combined organic extracts were washed with water (3×50 mL), brine (50 mL), dried (MgSO₄), filtered and concentrated in vacuo to afford an orange oil. The crude product was purified by chromatography on silica gel (40 g column, 0-2% MeOH in EtOAc) to afford the sub-title compound (498 mg) as an orange oil.

¹H NMR (400 MHz, DMSO-d6) δ: 9.40 (s, 1H), 9.30 (s, 1H), 8.41 (d, 1H), 8.12-8.09 (m, 1H), 7.82-7.80 (m, 1H), 7.62-7.52 (m, 3H), 7.38 (d, 1H), 6.85 (s, 2H), 6.54 (d, 1H), 6.04 (t, 1H), 3.90-3.84 (m, 2H), 3.69-3.63 (m, 2H), 3.58-3.48 (m, 25H), 3.42-3.40 (m, 2H), 3.22 (s, 3H), 1.52 (s, 9H).

(iv) N-(3-(2,5,8,11,14,17,20-heptaoxadocosan-22-yloxy)-5-methoxyphenyl)-4-((4-aminonaphthalen-1-yl)oxy)pyrimidin-2-amine To a stirred solution of the product from step (iii) above (452 mg, 0.567 mmol) in DCM (10 mL) was added TFA (2.2 mL, 28.6 mmol). The resulting solution was stirred at rt for 1 h. The reaction mixture was concentrated in vacuo, dissolved in the minimum of MeOH then loaded onto SCX. The column was eluted with MeOH (3 column volumes) then 1% $NH_3$ in MeOH (3 column volumes). The product-containing fraction was concentrated in vacuo to afford the sub-title compound (258 mg) as a dark orange oil.

$^1$H NMR (400 MHz, DMSO-d6) δ: 9.30 (s, 1H), 8.32 (d, 1H), 8.14-8.10 (m, 1H), 7.66-7.63 (m, 1H), 7.45-7.39 (m, 2H), 7.10 (d, 1H), 6.87 (s, 2H), 6.70 (d, 1H), 6.34 (d, 1H), 6.04 (t, 1H), 5.68 (s, 2H), 3.89-3.87 (m, 2H), 3.69-3.67 (m, 2H), 3.60-3.47 (m, 25H), 3.45-3.41 (m, 2H), 3.23 (s, 3H).

LCMS m/z 349 (M+2H)$^{2+}$ (ES$^+$)

(v) 1-(4-((2-((3-(2,5,8,11,14,17,20-Heptaoxadocosan-22-yloxy)-5-methoxyphenyl)amino) pyrimidin-4-yl)oxy)naphthalen-1-yl)-3-(3-(tert-butyl)-1-methyl-1H-pyrazol-5-yl)urea A mixture of phenyl (3-(tert-butyl)-1-methyl-1H-pyrazol-5-yl)carbamate (see Example 1(vi) above; 53 mg, 0.190 mmol), the product from step (iv) above (120 mg, 0.170 mmol) and triethylamine (5 μL, 0.036 mmol) in i-PrOAc (2 mL) was heated at 70° C. for 1 h. The reaction was cooled to rt and concentrated in vacuo. The crude product was purified by chromatography on silica gel (40 g column, 0-10% MeOH in EtOAc) to afford a colourless oil. The oil was dissolved in MeCN and water (3 mL, 1:1) and freeze-dried overnight to afford the title compound (86 mg) as a sticky white solid.

$^1$H NMR (400 MHz, DMSO-d6) δ: 9.41 (s, 1H), 9.01 (s, 1H), 8.86 (s, 1H), 8.41 (d, 1H), 8.18 (d, 1H), 8.00 (d, 1H), 7.84 (d, 1H), 7.70-7.66 (m, 1H), 7.61-7.57 (m, 1H), 7.40 (d, 1H), 6.82-6.80 (m, 2H), 6.53 (d, 1H), 6.12 (s, 1H), 6.03 (t, 1H), 3.88-3.85 (m, 2H), 3.68 (s, 3H), 3.67-3.64 (m, 2H), 3.57-3.48 (m, 25H), 3.42-3.39 (m, 2H), 3.22 (s, 3H), 1.23 (s, 9H).

LCMS m/z 876 (M+H)$^+$, 439 (M+2H)$^{2+}$ (ES$^+$)

Example 7

3-((4-((4-(3-(3-(tert-Butyl)-1-methyl-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide

(i) 3-Amino-5-((triisopropylsilyl)ethynyl)benzoic acid

Pd(PPh$_3$)$_4$ (9.36 g, 8.10 mmol) was added to a degassed suspension of 3-amino-5-bromobenzoic acid (50 g, 231 mmol), CuI (1.499 g, 7.87 mmol) and ethynyltriisopropylsilane (80 mL, 356 mmol) in Et$_3$N (300 mL) and DMF (300 mL). The mixture was heated to 90° C. for 2 h. The mixture was cooled and carefully poured into ice-cold HCl (2.0 M aq.) (1100 mL, 2200 mmol) and diluted with diethyl ether (500 mL). The biphasic mixture was filtered to remove palladium residues. The layers of the filtrate were separated and the aqueous phase was extracted with a further portion of diethyl ether (300 mL). The organic phases were combined and washed with 20% brine (2×300 mL), 40% brine (300 mL), dried (MgSO$_4$), filtered and concentrated in vacuo affording a pale orange solid. The solid was recrystallised in acetonitrile (250 mL) and collected by filtration, washing with fresh acetonitrile (2×30 mL) affording the product as a yellow solid. The solid was slurried in hexane (250 mL) for 5 h then filtered, washing with more hexane to afford the sub-title compound (45.5 g) as a pale yellow solid.

$^1$H NMR (400 MHz, DMSO-d6) δ: 12.87 (bs, 1H), 7.18 (t, 1H), 7.10 (t, 1H), 6.86 (t, 1H), 5.54 (bs, 2H), 1.10 (s, 21H).

LCMS m/z 318 (M+H)$^+$ (ES$^+$); 316 (M−H)$^−$ (ES$^−$)

(ii) 3-((4-((4-((tert-Butoxycarbonyl)amino)naphthalen-1-yl)oxy)pyrimidin-2-yl)amino)-5-((triisopropylsilyl)ethynyl)benzoic acid A suspension of tert-butyl (4-((2-chloropyrimidin-4-yl)oxy)naphthalen-1-yl)carbamate (see, for example, Ito, K. et al., WO 2010/067130, 17 Jun. 2010; 42.6 g, 115 mmol), the compound from step (i) above (40.00 g, 126 mmol), BINAP (6.42 g, 10.31 mmol) and caesium carbonate (74.6 g, 229 mmol) in 1,4-dioxane (500 mL) was degassed with nitrogen for 10 min. Pd$_2$(dba)$_3$ (4.20 g, 4.58 mmol) was added and the mixture was heated to 90° C. for 2.5 h. The mixture was diluted with diethyl ether (600 mL) then washed with water (600 mL), followed by 0.5 M HCl solution (500 mL) and saturated brine (500 mL). The organic phase was dried (MgSO$_4$), filtered and concentrated in vacuo affording the sub-title compound (96 g) as a red foam which was used in the next step without further purification.

(iii) 3-((4-((4-((tert-butoxycarbonyl)amino)naphthalen-1-yl)oxy)pyrimidin-2-yl)amino)-5-ethynylbenzoic acid The compound from step (ii) above (96 g) was dissolved in THF (60 mL) and diluted with MeCN (400 mL). 1.0 M TBAF in THF (235 mL, 235 mmol) was added and the reaction stirred at rt overnight. The reaction was diluted with

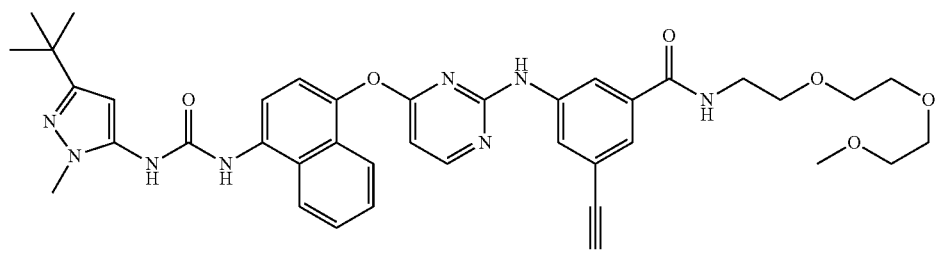 [SMILES: C#Cc1cc(Nc2nccc(Oc3ccc(NC(=O)Nc4cc(C(C)(C)C)nn4C)c4ccccc34)n2)cc(C(=O)NCCOCCOCCOC)c1]

MeCN (300 mL) and water (600 mL), then 1M HCl solution (100 mL, 1 eq.) was added and stirring continued resulting in the precipitation of a pink solid which was collected by filtration. The pink solid was triturated in MeCN at 80° C., collected by filtration and dried at 40° C. under vacuum for 2 h. The solid was re-suspended in (9:1) EtOAc/THF (400 mL) and heated to 60° C. for 90 mins then cooled to rt and stirred overnight. The suspended solid was collected by filtration, washing with EtOAc affording the sub-title compound (47 g) as a pale yellow/beige solid.

$^1$H NMR (400 MHz, DMSO-d6) δ: 13.12 (bs, 1H), 9.83 (s, 1H), 9.32 (s, 1H), 8.46 (d, 1H), 8.28 (s, 1H), 8.10 (d, 1H), 8.01 (s, 1H), 7.82 (d, 1H), 7.54-7.63 (m, 3H), 7.49 (s, 1H), 7.42 (d, 1H), 6.61 (d, 1H), 4.17 (s, 1H), 1.52 (s, 9H).

LCMS m/z 497 (M+H)$^+$ (ES$^+$); 495 (M−H)$^−$ (ES$^−$)

(iv) tert-Butyl (4-((2-((3-ethynyl-5-((2-(2-(2-methoxyethoxy)ethoxy)ethyl)carbamoyl)-phenyl)amino)pyrimidin-4-yl)oxy)naphthalen-1-yl)carbamate T3P, 50% w/w in EtOAc (54.0 ml, 91 mmol) was added to a solution of the product from step (iii) above (30 g, 60.4 mmol), 2-(2-(2-methoxyethoxy)ethoxy)ethanamine (11.83 g, 72.5 mmol), and TEA (20 mL, 143 mmol) in DMF (400 mL). The mixture was stirred at rt for 18 h. The mixture was diluted with water (700 mL) and saturated NaHCO$_3$ solution (500 mL) and the mixture was extracted with ethyl acetate (3×400 mL). The combined organic phases were washed with 20% brine (3×500 mL), saturated brine (3×500 mL), dried (MgSO$_4$), filtered and concentrated in vacuo. The crude product was purified in two batches by chromatography on the companion (330 g column, 1-5% MeOH in DCM) to afford the sub-title compound (24.4 g) as a pale yellow foam.

$^1$H NMR (400 MHz, DMSO-d6) δ: 9.74 (s, 1H), 9.31 (s, 1H), 8.44-8.47 (m, 2H), 8.11 (s, 1H), 8.10 (d, 1H), 7.91 (s, 1H), 7.82 (d, 1H), 7.54-7.63 (m, 3H), 7.46 (s, 1H), 7.42 (d, 1H), 6.58 (d, 1H), 4.15 (s, 1H), 3.49-3.53 (m, 8H), 3.36-3.41 (m, 4H), 3.21 (s, 3H), 1.52 (s, 9H).

LCMS m/z 642 (M+H)$^+$ (ES$^+$); 640 (M−H)$^−$ (ES$^−$)

(v) 3-((4-((4-Aminonaphthalen-1-yl)oxy)pyrimidin-2-yl)amino)-5-ethynyl-N-(2-(2-(2-methoxyethoxy)ethoxy)ethyl)benzamide TFA (30 mL, 389 mmol) was added dropwise to a stirred solution of the product from step (iv) above (12.0 g, 18.70 mmol) in DCM (200 mL). The reaction was stirred at rt for 3 h. The reaction was concentrated in vacuo and the residue partitioned between DCM (300 mL) and sat. NaHCO$_3$ soln. (400 mL). The aqueous phase was separated and extracted with DCM (200 mL). The combined organics were dried (MgSO$_4$), filtered and concentrated in vacuo to give a beige foam. The crude product was purified by chromatography on the Companion (220 g column, 1-5% MeOH in DCM) to afford the sub-title compound (9.0 g) as a pale pink foam.

$^1$H NMR (400 MHz, DMSO-d6) δ: 9.74 (s, 1H), 8.46 (t, 1H), 8.36 (d, 1H), 8.12-8.14 (m, 1H), 8.07 (s, 1H), 7.94 (s, 1H), 7.62-7.64 (m, 1H), 7.41-7.46 (m, 3H), 7.15 (d, 1H), 6.70 (d, 1H), 6.38 (d, 1H), 5.76 (s, 2H), 4.18 (s, 1H), 3.49-3.53 (m, 8H), 3.36-3.41 (m, 4H), 3.21 (s, 3H).

LCMS m/z 542 (M+H)$^+$ (ES$^+$); 540 (M−H)$^−$ (ES$^−$)

(vi) 3-((4-((4-(3-(3-(tert-Butyl)-1-methyl-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide A stirred solution of phenyl (3-(tert-butyl)-1-methyl-1H-pyrazol-5-yl)carbamate (see Example 1(vi) above; 90 mg, 0.329 mmol), the product from step (v) above (150 mg, 0.277 mmol) and Et$_3$N (20 μL, 0.143 mmol) in isopropyl acetate (5 mL) was heated to 60° C. (block temp) for 2 h. The mixture was concentrated under reduced pressure and the residue was purified by chromatography on the Companion (40 g column, EtOAc) to afford a cream solid. The solid was recrystallised from acetonitrile twice to yield the title compound (93 mg) as a white solid.

$^1$H NMR (400 MHz, DMSO-d6) δ: 9.76 (s, 1H), 9.00 (s, 1H), 8.86 (s, 1H), 8.50-8.37 (m, 2H), 8.18 (d, 1H), 8.07 (s, 1H), 7.99 (d, 1H), 7.87 (s, 1H), 7.85 (d, 1H), 7.68 (ddd, 1H), 7.60 (ddd, 1H), 7.48-7.39 (m, 2H), 7.56 (d, 1H), 6.12 (s, 1H), 4.12 (s, 1H), 3.69 (s, 3H), 3.57-3.43 (m, 8H), 3.44-3.35 (m, 4H), 3.21 (s, 3H), 1.23 (s, 9H).

LCMS m/z 721 (M+H)$^+$ (ES$^+$); 719 (M−H)$^−$ (ES$^−$)

Example 8

3-((4-((4-(3-(3-(tert-Butyl)-1-ethyl-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide

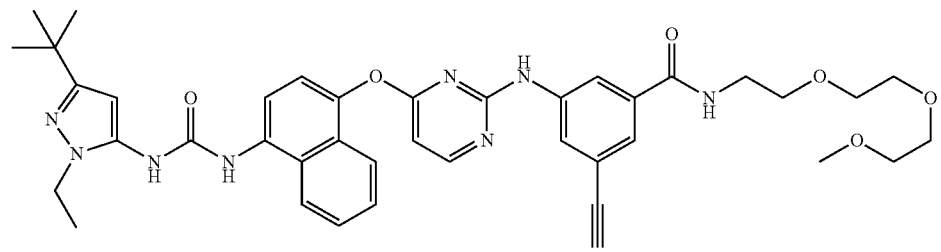 [SMILES: C#Cc1cc(Nc2nccc(Oc3ccc(NC(=O)Nc4cc(C(C)(C)C)nn4CC)c4ccccc34)n2)cc(C(=O)NCCOCCOCCOC)c1]

3-((4-((4-Aminonaphthalen-1-yl)oxy)pyrimidin-2-yl)amino)-5-ethynyl-N-(2-(2-(2-methoxyethoxy)ethoxy)ethyl)benzamide A stirred solution of phenyl (3-(tert-butyl)-1-ethyl-1H-pyrazol-5-yl)carbamate (90 mg, 0.313 mmol), 3-((4-((4-aminonaphthalen-1-yl)oxy)pyrimidin-2-yl)amino)-5-ethynyl-N-(2-(2-(2-methoxyethoxy)ethoxy)ethyl)benzamide (see Example 7(v) above; 150 mg, 0.277 mmol) and Et₃N (20 μL, 0.143 mmol) in isopropyl acetate (5 mL) was heated to 60° C. (block temp) for 6 h. The resulting precipitate was collected by filtration then recrystallised in acetonitrile to yield the title compound (48 mg).

¹H NMR (DMSO-d6) 400 MHz, δ: 9.76 (s, 1H), 8.98 (s, 1H), 8.78 (s, 1H), 8.48-8.43 (m, 1H), 8.44 (d, 1H), 8.18 (d, 1H), 8.07 (s, 1H), 7.99 (d, 1H), 7.87 (s, 1H), 7.85 (d, 1H), 7.69 (ddd, 1H), 7.60 (ddd, 1H), 7.47-7.44 (m, 1H), 7.43 (d, 1H), 6.56 (d, 1H), 6.13 (s, 1H), 4.11 (s, 1H), 4.02 (q, 2H), 3.56-3.44 (m, 8H), 3.43-3.35 (m, 4H), 3.21 (s, 3H), 1.35 (t, 3H), 1.24 (s, 9H).

LCMS m/z 735 (M+H)⁺ (ES⁺)

Example 9

3-((4-((4-(3-(3-(tert-Butyl)-1-methyl-1H-pyrazol-5-yl)ureido)naphthalen-1-yl)oxy)pyridin-2-yl)amino)-5-ethynyl-N-(2-(2-(2-methoxyethoxy)ethoxy)ethyl)benzamide

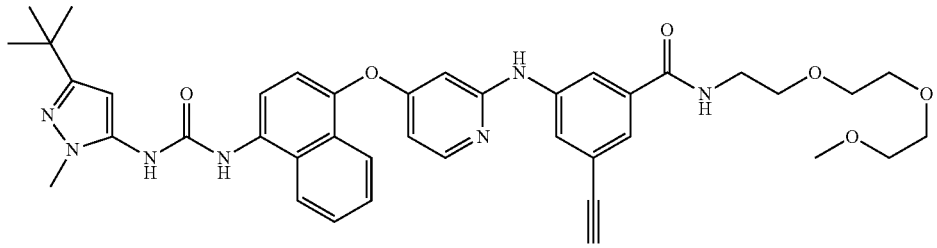 [SMILES: C#Cc1cc(Nc2cc(Oc3ccc(NC(=O)Nc4cc(C(C)(C)C)nn4C)c4ccccc34)ccn2)cc(C(=O)NCCOCCOCCOC)c1]

(i) 3-((4-((4-((tert-Butoxycarbonyl)amino)naphthalen-1-yl)oxy)pyridin-2-yl)amino)-5-((triisopropylsilyl)ethynyl)benzoic acid N₂ was bubbled through a mixture of tert-butyl (4-((2-chloropyridin-4-yl)oxy)naphthalen-1-yl)carbamate (see Example 5(ii) above; 0.5 g, 1.348 mmol), 3-amino-5-((triisopropylsilyl)ethynyl)benzoic acid (see Example 7(i) above; 0.490 g, 1.544 mmol), Cs₂CO₃ (0.966 g, 2.97 mmol), BINAP (0.078 g, 0.125 mmol) and Pd₂dba₃ (0.056 g, 0.061 mmol) in dioxane (15 mL) for 10 min then heated at 90° C. for 4 h. The mixture was partitioned between ether (100 mL) and 1M HCl (50 mL), the organic layer separated, washed with water, dried (MgSO₄), filtered and evaporated under reduced pressure. The residue was triturated with ether/isohexane, filtered and dried to afford the crude sub-title compound (760 mg).

(ii) 3-((4-((4-((tert-Butoxycarbonyl)amino)naphthalen-1-yl)oxy)pyridin-2-yl)amino)-5-ethynylbenzoic acid 1.0 M TBAF in THF (2.5 mL, 2.500 mmol) was added to a stirred solution of the crude product from step (i) above (760 mg) in THF (15 mL). The mixture was stirred for 2 h then water (10 mL) added and acidified to pH-4 with 1 M HCl. The mixture was partitioned between EtOAc (70 mL) and water (40 mL), the organic phase washed with sat brine (50 mL), dried (MgSO₄), filtered and evaporated under reduced pressure. The crude product was purified by chromatography on silica gel (40 g column, 0-100% EtOAc/isohexane) to afford the sub-title compound (344 mg) as a foam.

¹H NMR (DMSO-d6) 400 MHz, δ: 13.07 (s, 1H), 9.39 (s, 1H), 9.29 (s, 1H), 8.18-8.13 (m, 4H), 7.84 (d, 1H), 7.66-7.56 (m, 3H), 7.44 (s, 1H), 7.38 (d, 1H), 6.66 (dd, 1H), 6.07 (d, 1H), 4.22 (s, 1H), 1.53 (s, 9H).

LCMS m/z 496 (M+H)⁺ (ES⁺)

(iii) tert-Butyl (4-((2-((3-ethynyl-5-((2-(2-(2-methoxyethoxy)ethoxy)ethyl)carbamoyl)-phenyl)amino)pyridin-4-yl)oxy)naphthalen-1-yl)carbamate HATU (500 mg, 1.315 mmol) was added to a stirred solution of the product from step (ii) above (500 mg, 1.009 mmol), 2-(2-(2-methoxyethoxy)ethoxy)ethanamine (277 mg, 1.695 mmol) and triethylamine (250 μL, 1.796 mmol) in N,N-dimethylformamide (10 mL). The mixture was stirred at room temperature for 18 h. The mixture was diluted with EtOAc (50 mL) and washed with water (50 mL), 20% brine (3×50 mL) and saturated brine (50 mL). The organic phase was dried (MgSO₄), filtered and concentrated under reduced pressure. The crude product was purified by chromatography on the Companion (40 g column, EtOAc) to afford the sub-title compound (580 mg) as a tan foam.

LCMS m/z 641 (M+H)⁺ (ES⁺); 639 (M–H)⁻ (ES⁻)

(iv) 3-((4-((4-Aminonaphthalen-1-yl)oxy)pyridin-2-yl)amino)-5-ethynyl-N-(2-(2-(2-methoxy-ethoxy)ethoxy)ethyl)benzamide TFA (1 mL, 12.98 mmol) was added to a solution of the product from step (iii) above (580 mg, 0.905 mmol) in DCM (5 mL) at rt and stirred overnight. The volatiles were removed under reduced pressure and the residue was redissolved in DCM (20 mL). The organic phase was washed with saturated sodium bicarbonate solution (20 mL), dried (MgSO₄) and concentrated under reduced pressure to yield the sub-title compound (475 mg).

LCMS m/z 541 (M+H)⁺ (ES⁺); 539 (M–H)⁻ (ES⁻)

(v) 3-((4-((4-(3-(3-(tert-Butyl)-1-methyl-1H-pyrazol-5-yl)ureido)naphthalen-1-yl)oxy)-pyridin-2-yl)amino)-5-ethynyl-N-(2-(2-(2-methoxyethoxy)ethoxy)ethyl)benzamide A stirred solution of phenyl (3-(tert-butyl)-1-methyl-1H-pyrazol-5-yl)carbamate (see Example 1(vi) above; 90 mg, 0.329 mmol), the product from step (iv) above (150 mg, 0.277 mmol) and Et₃N (10 μL, 0.072 mmol) in isopropyl acetate (5 mL) was heated to 50° C. (block temp) for 18 h. The mixture was concentrated under reduced pressure and the residue was purified by chromatography on the Companion (40 g column, EtOAc) to afford a gum. The gum was purified by preparative HPLC (Gilson, Acidic (0.1% Formic acid), Acidic, Waters X-Select Prep-C18, 5 μm, 19×50 mm column, 25-70% MeCN in Water). Pure fractions were combined and concentrated to remove acetonitrile before basifying with saturated NaHCO₃ solution (10 mL). The free compound was extracted with ethyl acetate, washed with saturated brine (20 mL), dried (MgSO₄) and concentrated under reduced pressure to afford the title compound (86 mg) as a tan foam.

¹H NMR (400 MHz, DMSO-d6) δ: 9.22 (s, 1H), 9.06 (s, 1H), 8.87 (s, 1H), 8.47 (dd, 1H), 8.21 (d, 1H), 8.15 (d, 1H), 8.13-8.09 (m, 1H), 8.03 (d, 1H), 7.95-7.91 (m, 1H), 7.88 (d, 1H), 7.71 (ddd, 1H), 7.62 (ddd, 1H), 7.42 (dd, 1H), 7.39 (d, 1H), 6.61 (dd, 1H), 6.14 (d, 1H), 6.13 (s, 1H), 4.19 (s, 1H), 3.69 (s, 3H), 3.56-3.45 (m, 8H), 3.43-3.35 (m, 4H), 3.21 (s, 3H), 1.24 (s, 9H)

LCMS m/z 720 (M+H)⁺ (ES⁺); 718 (M−H)⁻ (ES⁻)

Example 10

3-Ethynyl-5-((4-((4-(3-(3-isopropyl-1-methyl-1H-pyrazol-5-yl)ureido)naphthalen-1-yl)oxy)pyrimidin-2-yl)amino)-N-(2-morpholinoethyl)benzamide

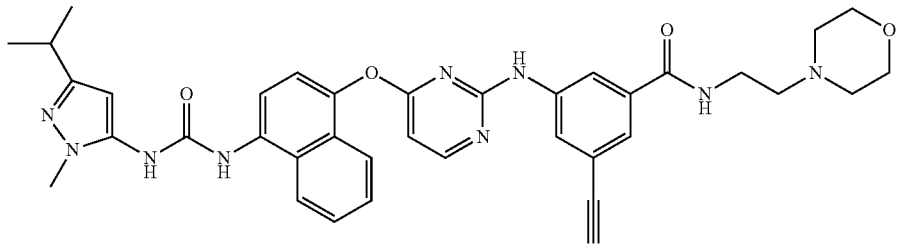 [SMILES: C#Cc1cc(Nc2nccc(Oc3ccc(NC(=O)Nc4cc(C(C)C)nn4C)c4ccccc34)n2)cc(C(=O)NCCN2CCOCC2)c1]

(i) Phenyl (3-isopropyl-1-methyl-1H-pyrazol-5-yl)carbamate

Phenyl chloroformate (950 µL, 7.57 mmol) was added to a stirred mixture of 3-isopropyl-1-methyl-1H-pyrazol-5-amine (1 g, 7.18 mmol) and NaHCO₃ (1.21 g, 14.40 mmol) in THF (10 mL) and DCM (20 mL). The mixture was stirred for 18 h, partitioned between DCM (150 mL) and water (100 mL), the organic layer was washed with brine (50 mL), dried (MgSO₄), filtered and evaporated under reduced pressure. The residue was triturated with ether/isohexane then filtered to afford the sub-title compound (1.06 g) as a white solid.

1H NMR (CDCl₃) 400 MHz, δ: 7.44-7.21 (m, 5H), 6.82 (brs, 1H), 6.11 (s, 1H), 3.78 (s, 3H), 2.94 (sept, 1H), 1.27 (d, 6H).

LCMS m/z 260 (M+H)⁺ (ES⁺)

(ii) 3-Ethynyl-5-((4-((4-(3-(3-isopropyl-1-methyl-1H-pyrazol-5-yl)ureido)naphthalen-1-yl)oxy)pyrimidin-2-yl)amino)-N-(2-morpholinoethyl)benzamide TEA (10 µL, 0.072 mmol) was added to a solution of the product from step (i) above (60 mg, 0.231 mmol) and 3-((4-((4-aminonaphthalen-1-yl)oxy)pyrimidin-2-yl)amino)-5-ethynyl-N-(2-morpholinoethyl)benzamide (see Example 1(v) above; 100 mg, 0.197 mmol) in THF (2 mL) at 60° C. (block temperature) and the reaction heated for 5 h. The reaction was cooled to rt and left stirring overnight. The resulting solid was filtered off, washed with THF (1 mL) and dried to afford the title compound (58 mg) as a colourless solid.

¹H NMR (400 MHz, DMSO-d6) δ 9.76 (s, 1H), 8.99 (s, 1H), 8.88 (s, 1H), 8.44 (d, 1H), 8.35 (t, 1H), 8.18 (d, 1H), 8.06 (s, 1H), 7.99 (d, 1H), 7.92-7.76 (m, 2H), 7.73-7.63 (m, 1H), 7.63-7.53 (m, 1H), 7.47-7.40 (m, 2H), 6.57 (d, 1H), 6.08 (s, 1H), 4.12 (s, 1H), 3.68 (s, 3H), 3.56 (t, 4H), 3.41-3.33 (m, 2H), 2.81 (hept, 1H), 2.47-2.33 (m, 6H), 1.19 (d, 6H).

LCMS m/z 674 (M+H)⁺ (ES⁺)

Example 11

3-Ethynyl-5-((4-((4-(3-(3-isopropyl-1-methyl-1H-pyrazol-5-yl)ureido)naphthalen-1-yl)oxy)pyrimidin-2-yl)amino)-N-(2-(2-(2-methoxyethoxy)ethoxy)ethyl)benzamide

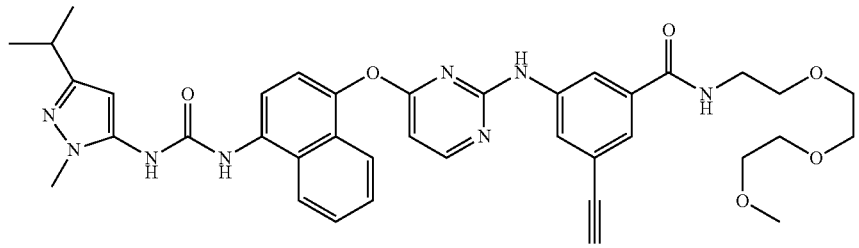 [SMILES: C#Cc1cc(Nc2nccc(Oc3ccc(NC(=O)Nc4cc(C(C)C)nn4C)c4ccccc34)n2)cc(C(=O)NCCOCCOCCOC)c1]

TEA (10 µL, 0.072 mmol) was added to a solution of phenyl (3-isopropyl-1-methyl-1H-pyrazol-5-yl)carbamate (see Example 10(i) above; 60 mg, 0.231 mmol) and 3-((4-((4-aminonaphthalen-1-yl)oxy)pyrimidin-2-yl)amino)-5-ethynyl-N-(2-(2-(2-methoxyethoxy)-ethoxy)ethyl)benzamide (see Example 7(v) above; 100 mg, 0.185 mmol) in THF (2 mL) at 60° C. (block temperature) and the reaction heated for 16 h. The resulting solid was filtered off, washed with THF (1 mL) and dried to give a pale pink glass. The crude product was purified by preparative HPLC (Gilson, Basic (0.1% Ammonium Bicarbonate), Basic, Waters X-Bridge Prep-C18, 5 μm, 19×50 mm column, 25-70% MeCN in Water) to afford the title compound (4 mg) as a pale tan solid.

$^1$H NMR (400 MHz, DMSO-d6) δ 9.76 (s, 1H), 9.31 (s, 1H), 9.27 (s, 1H), 8.50-8.35 (m, 2H), 8.22 (d, 1H), 8.07 (s, 1H), 7.97 (d, 1H), 7.92-7.79 (m, 2H), 7.71-7.63 (m, 1H), 7.63-7.54 (m, 1H), 7.50-7.35 (m, 2H), 6.57 (d, 1H), 6.07 (s, 1H), 4.13 (s, 1H), 3.68 (s, 3H), 3.55-3.46 (m, 8H), 3.44-3.35 (m, 4H), 3.21 (s, 3H), 2.80 (hept, 1H), 1.18 (d, 6H).

LCMS m/z 707 (M+H)$^+$ (ES$^+$)

Example 12

3-((4-((4-(3-(1,3-Di-tert-butyl-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide DCM) to afford an off-white solid. The material was triturated with iPrOAc and hexane then collected by filtration. The residue was dissolved in DCM (10 mL) and THF (2 mL) and the solution washed with 1M HCl solution (10 mL). The organic phase was dried via hydrophobic frit and concentrated in vacuo affording the title compound (31 mg) as a white solid.

$^1$H NMR (400 MHz, DMSO-d6) δ: 9.78 (s, 1H), 9.17 (s, 1H), 8.17 (t, 1H), 8.44 (d, 1H), 8.40 (s, 1H), 8.25 (d, 1H), 8.07 (s, 1H), 7.97 (d, 1H), 7.87 (s, 1H), 7.83 (d, 1H), 7.67 (t, 1H), 7.59 (t, 1H), 7.45 (s, 1H), 7.43 (d, 1H), 6.57 (d, 1H), 6.09 (s, 1H), 4.14 (s, 1H), 3.48-3.51 (m, 8H), 3.36-3.41 (m, 4H), 3.21 (s, 3H), 1.61 (s, 9H), 1.24 (s, 9H).

LCMS m/z 763 (M+H)$^+$ (ES$^+$)

Example 13

The following compounds were prepared by methods analogous to those described above.

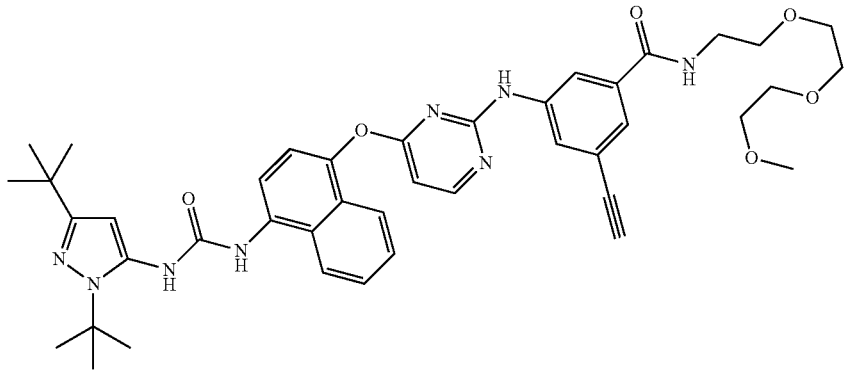 [SMILES: C#Cc1cc(Nc2nccc(Oc3ccc(NC(=O)Nc4cc(C(C)(C)C)nn4C(C)(C)C)c4ccccc34)n2)cc(C(=O)NCCOCCOCCOC)c1]

(i) Phenyl (4-((2-((3-ethynyl-5-((2-(2-(2-methoxyethoxy)ethoxy)ethyl)carbamoyl)phenyl)amino)pyrimidin-4-yl)oxy)naphthalen-1-yl)carbamate Phenyl chloroformate (139 μL, 1.108 mmol) was added to a stirred mixture of 3-((4-((4-aminonaphthalen-1-yl)oxy)pyrimidin-2-yl)amino)-5-ethynyl-N-(2-(2-(2-methoxy-ethoxy)-ethoxy)ethyl)benzamide (see Example 7(v) above; 600 mg, 1.108 mmol) and NaHCO$_3$ (186 mg, 2.216 mmol) in DCM (12 mL) and THF (4 mL) at rt. The mixture was stirred overnight then partitioned between DCM (20 mL) and water (20 mL). The organic layer was separated and dried via a hydrophobic frit, affording the sub-title compound (742 mg) as a pale pink foam LCMS m/z 662 (M+H)$^+$ (ES$^+$)

(ii) 3-((4-((4-(3-(1,3-Di-tert-butyl-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide Triethylamine (5 μL, 0.036 mmol) was added to a mixture of 1,3-di-tert-butyl-1H-pyrazol-5-amine (34 mg, 0.151 mmol) and the product from step (i) above (100 mg, 0.151 mmol) in isopropyl acetate (3 mL) and the mixture heated at 60° C. (block temperature) overnight. The reaction was cooled to rt, diluted with THF and concentrated in vacuo onto silica gel. The crude product was purified by chromatography on the Companion (12 g column, 1-6% MeOH in (a) 3-((4-((4-(3-(3-(tert-Butyl)-1-isopropyl-1H-pyrazol-5-yl)ureido)naphthalen-1-yl)oxy)pyrimidin-2-yl)amino)-5-ethynyl-N-(2-(2-(2-methoxyethoxy)ethoxy)ethyl)-benzamide $^1$H NMR (DMSO-d6) 400 MHz, δ: 9.77 (s, 1H), 8.98 (s, 1H), 8.71 (s, 1H), 8.44-8.49 (m, 2H), 8.18 (d, 1H), 8.08 (s, 1H), 7.98 (d, 1H), 7.83-7.87 (m, 2H), 7.69 (t, 1H), 7.60 (t, 1H), 7.43-7.45 (m, 2H), 6.57 (d, 1H), 6.09 (s, 1H), 4.40-4.50 (m, 1H), 4.13 (s, 1H), 3.48-3.51 (m, 8H), 3.37-3.41 (m, 4H), 3.21 (s, 3H), 1.40 (d, 6H), 1.24 (s, 9H).

LCMS m/z 749 (M+H)$^+$ (ES$^+$)

(b) 3-((4-((4-(3-(3-(tert-Butyl)-1-propyl-1H-pyrazol-5-yl)ureido)naphthalen-1-yl)oxy)-pyrimidin-2-yl)amino)-5-ethynyl-N-(2-(2-(2-methoxyethoxy)ethoxy)ethyl)benzamide $^1$H NMR (DMSO-d6) 400 MHz, δ: 9.78 (s, 1H), 8.99 (s, 1H), 8.76 (s, 1H), 8.44-8.49 (m, 2H), 8.18 (d, 1H), 8.07 (s, 1H), 7.98 (d, 1H), 7.84-7.87 (m, 2H), 7.69 (t, 1H), 7.60 (t, 1H), 7.44-7.46 (m, 2H), 6.57 (d, 1H), 6.13 (s, 1H), 4.13 (s, 1H), 3.93 (t, 2H), 3.48-3.51 (m, 8H), 3.37-3.41 (m, 4H), 3.21 (s, 3H), 1.73-1.82 (m, 2H), 1.24 (s, 9H), 0.91 (t, 3H).

LCMS m/z 749 (M+H)$^+$ (ES$^+$)

Biological Testing: Experimental Methods
Enzyme Inhibition Assays

The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition

The following two assay variants can be used for determination of p38 MAPKα inhibition.

Method 1

The inhibitory activities of test compounds against the p38 MAPKα isoform (MAPK14: Invitrogen), are evaluated indirectly by determining the level of activation/phosphorylation of the down-stream molecule, MAPKAP-K2. The p38 MAPKα protein (80 ng/mL, 2.5 µL) is mixed with the test compound (2.5 µL of either 4 µg/mL, 0.4 µg/mL, 0.04 µg/mL or 0.004 µg/mL) for 2 hr at RT. The mix solution (2.5 µL) of the p38α inactive target MAPKAP-K2 (Invitrogen, 600 ng/mL) and FRET peptide (8 µM; a phosphorylation target for MAPKAP-K2) is then added and the kinase reaction is initiated by adding ATP (40 µM, 2.5 µL). The mixture is incubated for 1 hr at RT. Development reagent (protease, 5 µL) is added for 1 hr prior to detection in a fluorescence microplate reader (Varioskan® Flash, Thermo-Fisher Scientific).

Method 2

This method follows the same steps as Method 1 above, but utilises a higher concentration of the p38 MAPKα protein (2.5 µL of 200 ng/mL protein instead of 2.5 µL of 80 ng/mL protein) for mixing with the test compound.

p38 MAPKγ Enzyme Inhibition

The inhibitory activities of compounds of the invention against p38MAPKγ (MAPK12: Invitrogen), are evaluated in a similar fashion to that described hereinabove. The enzyme (800 ng/mL, 2.5 µL) is incubated with the test compound (2.5 µL at either 4 µg/mL, 0.4 µg/mL, 0.04 µg/mL, or 0.004 µg/mL) for 2 hr at RT. The FRET peptides (8 µM, 2.5 µL), and appropriate ATP solution (2.5 µL, 400 µM) is then added to the enzymes/compound mixtures and incubated for 1 hr. Development reagent (protease, 5 µL) is added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), are evaluated in a similar fashion to that described hereinabove. The relevant enzyme (3000 ng/mL or 2000 ng/mL respectively, 2.5 µL) is incubated with the test compound (either 4 µg/mL, 0.4 µg/mL, 0.04 µg/mL, or 0.004 µg/mL, 2.5 µL each) for 2 hr at RT. The FRET peptides (8 µM, 2.5 µL), and appropriate ATP solutions (2.5 µL, 800 µM for c-Src, and 60 µM ATP for Syk) are then added to the enzymes/compound mixtures and incubated for 1 hr. Development reagent (protease, 5 µL) is added for 1 hr prior to detection in a fluorescence microplate reader (Varioskan® Flash, ThermoFisher Scientific).

GSK 3α Enzyme Inhibition

The following two assay variants can be used for determination of GSK 3α inhibition.

Method 1

The inhibitory activities of compounds of the invention against the GSK 3α enzyme isoform (Invitrogen), are evaluated by determining the level of activation/phosphorylation of the target peptide. The GSK3-α protein (500 ng/mL, 2.5 µL) is mixed with the test compound (2.5 µL at either 4 µg/mL, 0.4 µg/mL, 0.04 µg/mL, or 0.004 µg/mL) for 2 hr at RT. The FRET peptide (8 µM, 2.5 µL), which is a phosphorylation target for GSK3α, and ATP (40 µM, 2.5 µL) are then added to the enzyme/compound mixture and the resulting mixture incubated for 1 hr. Development reagent (protease, 5 µL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction are calculated using the ratio of coumarin emission (donor) over fluorescein emission (acceptor), for which high ratios indicate high phosphorylation and low ratios indicate low phosphorylation levels. The percentage inhibition of each reaction is calculated relative to non-inhibited control and the 50% inhibitory concentration ($IC_{50}$ value) is then calculated from the concentration-response curve.

Method 2

This method follows the same steps as Method 1 above, but utilises a shorter period of mixing of the test compound (105 minutes instead of 2 hours) with the GSK3-α protein.

Cellular Assays

The compounds of the invention were studied using one or more of the following assays.

(a) LPS-Induced TNFα/IL-8 Release in d-U937 Cells

U937 cells, a human monocytic cell line, are differentiated to macrophage-type cells by incubation with phorbol myristate acetate (PMA; 100 ng/mL) for 48 to 72 hr. Cells are pre-incubated with final concentrations of test compound for 2 hr and are then stimulated with 0.1 µg/mL of LPS (from *E. Coli*: O111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 µg/mL of BIRB796 at each concentration of test compound by comparison against vehicle control. The relative 50% effective concentration ($REC_{50}$) is determined from the resultant concentration-response curve. The inhibition of IL-8 production is calculated at each concentration of test compound by comparison with vehicle control. The 50% inhibitory concentration ($IC_{50}$) is determined from the resultant concentration-response curve.

(b) LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 hours before addition of 1 ng/mL LPS (*Escherichia Coli* 0111:B4 from Sigma Aldrich) for 24 hours under normal tissue culture conditions (37° C., 5% $CO_2$). The supernatant is harvested for determination of IL-8 and TNFα concentrations by sandwich ELISA (Duo-set, R&D systems) and read on the fluorescence microplate reader (Varioskan® Flash, Thermo-Fisher Scientific). The concentration at 50% inhibition ($IC_{50}$) of IL-8 and TNFα production is calculated from the dose response curve.

(c) IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD28 monoclonal antibodies (0.3 µg/mL eBioscience and 3 µg/mL BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

(d) IL-1β-Induced IL-8 Release in HT29 Cells

HT29 cells, a human colon adenocarcinoma cell line, are plated in a 96 well plate (24 hrs) and pre-treated with compounds at the desired concentration for 2 hours before addition of 5 ng/mL of IL-1β (Abcam) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells are incubated for 2 hrs and non-adherent cells removed by washing. To differentiate the cells to macrophages the cells are incubated with 5 ng/mL of GM-CSF (Peprotech) for 7 days under normal tissue culture conditions. Compounds are then added to the cells at the desired concentration for a 2 hour pre-treatment before stimulation with 10 ng/mL LPS for 24 hours. Supernatants are harvested and IL-8 and TNFα release determined by Sandwich ELISA (Duo-set, R&D System). The $IC_{50}$ is determined from the dose response curve.

(f) Poly I:C-Induced ICAM-1 Expression in BEAS2B Cells

Poly I:C is used in these studies as a simple, RNA virus mimic. Poly I:C-Oligofectamine mixture (1 μg/mL Poly I:C, ±2% Oligofectamine, 25 μL; Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of test compounds for 2 hr and the level of ICAM1 expression on the cell surface is determined by cell-based ELISA. At a time point 18 hr after poly I:C transfection, cells are fixed with 4% formaldehyde in PBS and then endogenous peroxidase is quenched by the addition of washing buffer (100 μL, 0.05% Tween in PBS: PBS-Tween) containing 0.1% sodium azide and 1% hydrogen peroxide. Cells are washed with wash-buffer (3×200 μL) and after blocking the wells with 5% milk in PBS-Tween (100 μL) for 1 hr, the cells are incubated with anti-human ICAM-1 antibody (50 μL; Cell Signalling Technology, Danvers, Mass.) in 1% BSA PBS overnight at 4° C.

The cells are washed with PBS-Tween (3×200 μL) and incubated with the secondary antibody (100 μL; HRP-conjugated anti-rabbit IgG, Dako Ltd., Glostrup, Denmark). The cells are then incubated with substrate (50 μL) for 2-20 min, followed by the addition of stop solution (50 μL, 1N $H_2SO_4$). The ICAM-1 signal is detected by reading the absorbance at 450 nm against a reference wavelength of 655 nm using a spectrophotometer. The cells are then washed with PBS-Tween (3×200 μL) and total cell numbers in each well are determined by reading absorbance at 595 nm after Crystal Violet staining (50 μL of a 2% solution in PBS) and elution by 1% SDS solution (100 μL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) Cell Mitosis Assay

Peripheral blood mononucleocytes (PBMCs) from healthy subjects are separated from whole blood (Quintiles, London, UK) using a density gradient (Histopaque®-1077, Sigma-Aldrich, Poole, UK). The PBMCs (3 million cells per sample) are subsequently treated with 2% PHA (phytohaemagglutinin, Sigma-Aldrich, Poole, UK) for 48 hr, followed by a 20 hr exposure to varying concentrations of test compounds. At 2 hr before collection, PBMCs are treated with demecolcine (0.1 μg/mL; Invitrogen, Paisley, UK) to arrest cells in metaphase. To observe mitotic cells, PBMCs are permeabilised and fixed by adding Intraprep (50 μL; Beckman Coulter, France), and stained with anti-phospho-histone 3 (0.26 ng/L; #9701; Cell Signalling, Danvers, Mass.) and propidium iodide (1 mg/mL; Sigma-Aldrich, Poole, UK) as previously described (Muehlbauer P. A. and Schuler M. J., *Mutation Research*, 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(h) Rhinovirus-Induced IL-8 Release and ICAM-1 Expression

Human rhinovirus RV16 is obtained from the American Type Culture Collection (Manassas, Va.). Viral stocks are generated by infecting Hela cells with HRV until 80% of the cells are cytopathic.

BEAS2B cells are infected with HRV at an MOI of 5 and incubated for 2 hr at 33° C. with gentle shaking for to promote absorption. The cells are then washed with PBS, fresh media added and the cells are incubated for a further 72 hr. The supernatant is collected for assay of IL-8 concentrations using a Duoset ELISA development kit (R&D systems, Minneapolis, Minn.).

The level of ICAM1 expressing cell surface is determined by cell-based ELISA. At 72 hr after infection, cells are fixed with 4% formaldehyde in PBS. After quenching endogenous peroxidase by adding 0.1% sodium azide and 1% hydrogen peroxide, wells are washed with wash-buffer (0.05% Tween in PBS: PBS-Tween). After blocking well with 5% milk in PBS-Tween for 1 hr, the cells are incubated with anti-human ICAM-1 antibody in 5% BSA PBS-Tween (1:500) overnight. Wells are washed with PBS-Tween and incubated with the secondary antibody (HRP-conjugated anti-rabbit IgG, Dako Ltd.). The ICAM-1 signal is detected by adding substrate and reading at 450 nm with a reference wavelength of 655 nm using a spectrophotometer. The wells are then washed with PBS-Tween and total cell numbers in each well are determined by reading absorbance at 595 nm after Crystal Violet staining and elution by 1% SDS solution. The measured $OD_{450-655}$ readings are corrected for cell number by dividing with the $OD_{595}$ reading in each well. Compounds are added 2 hr before HRV infection and 2 hr after infection when non-infected HRV is washed out.

(i) Assessment of HRV16 Induced CPE in MRC5

MRC-5 cells are infected with HRV16 at an MOI of 1 in DMEM containing 5% FCS and 1.5 mM $MgCl_2$, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 μL, 2% formaldehyde, 10% methanol and 0.175% Methylene Blue) for 2 hr at RT. After washing, 1% SDS in distilled water (100 μL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(j) In Vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at an MOI of 0.001 in the LHC8 Media: RPMI-1640 (50:50) containing 15 mM magnesium chloride and incubated for 1 hr at 37° C. for adsorption. The cells are then washed with PBS (3×200 μL), fresh media (200 μL) is added and incubation continued for 4 days. Where appropriate, cells are pre-incubated with the compound or DMSO for 2 hr, and then added again after washout of the virus.

The cells are fixed with 4% formaldehyde in PBS solution (50 μL) for 20 min, washed with WB (3×200 μL), (washing buffer, PBS including 0.5% BSA and 0.05% Tween-20) and incubated with blocking solution (5% condensed milk in PBS) for 1 hr. Cells are then washed with WB (3×200 μL) and incubated for 1 hr at RT with anti-RSV (2F7) F-fusion protein antibody (40 μL; mouse monoclonal, lot 798760, Cat. No. ab43812, Abcam) in 5% BSA in PBS-tween. After washing, cells are incubated with an HRP-conjugated secondary antibody solution (50 μL) in 5% BSA in PBS-Tween (lot 00053170, Cat.No. PO447, Dako) and then TMB substrate added (50 μL; substrate reagent pack, lot 269472, Cat. No. DY999, R&D Systems, Inc.). This reaction is stopped by the addition of 2N $H_2SO_4$ (50 μL) and the resultant signal is determined colourimetrically (OD: 450 nm with a reference wavelength of 655 nm) in a microplate reader (Varioskan® Flash, ThermoFisher Scientific).

Cells are then washed and a 2.5% crystal violet solution (50 μL; lot 8656, Cat. No. PL7000, Pro-Lab Diagnostics) is applied for 30 min. After washing with WB, 1% SDS in distilled water (100 μL) is added to each well, and plates are shaken lightly on the shaker for 1 hr prior to reading the absorbance at 595 nm. The measured $OD_{450-655}$ readings are corrected to the cell number by dividing the $OD_{450-655}$ by the $OD_{595}$ readings. The percentage inhibition for each well is calculated and the $IC_{50}$ value is calculated from the concentration-response curve generated from the serial dilutions of compound.

(k) Cell Viability Assay: MTT Assay

Differentiated U937 cells are pre-incubated with each test compound (final concentration 1 μg/mL or 10 μg/mL in 200 μL media indicated below) under two protocols: the first for 4 hr in 5% FCS RPMI1640 media and the second in 10% FCS RPMI1640 media for 24 h. The supernatant is replaced with new media (200 μL) and MTT stock solution (10 μL, 5 mg/mL) is added to each well. After incubation for 1 hr the media are removed, DMSO (200 μL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(l) Human Biopsy Assay

Intestinal mucosa biopsies are obtained from the inflamed regions of the colon of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 hr in the organ culture chamber. The supernatant is harvested for determination of IL-6, IL-8, IL-1β and TNFα levels by R&D ELISA. Percentage inhibition of cytokine release by the test compounds is calculated relative to the cytokine release determined for the DMSO control (100%).

(m) Accumulation of β Catenin in d-U937 Cells

U937 cells, a human monocytic cell line, are differentiated into macrophage-type cells by incubation with PMA; (100 ng/mL) for between 48 to 72 hr. The cells are then incubated with either final concentrations of test compound or vehicle for 18 hr. The induction of β-catenin by the test compounds is stopped by replacing the media with 4% formaldehyde solution. Endogenous peroxide activity is neutralised by incubating with quenching buffer (100 μL, 0.1% sodium azide, 1% $H_2O_2$ in PBS with 0.05% Tween-20) for 20 min. The cells are washed with washing buffer (200 μL; PBS containing 0.05% Tween-20) and incubated with blocking solution (200 μL; 5% milk in PBS) for 1 hr, re-washed with washing buffer (200 μL) and then incubated overnight with anti-β-catenin antibody solution (50 μL) in 1% BSA/PBS (BD, Oxford, UK).

After washing with washing buffer (3×200 μL; PBS containing 0.05% Tween-20), cells are incubated with an HRP-conjugated secondary antibody solution (100 μL) in 1% BSA/PBS (Dako, Cambridge, UK) and the resultant signal is determined colourimetrically (OD: 450 nm with a reference wavelength of 655 nm) using TMB substrate (50 μL; R&D Systems, Abingdon, UK). This reaction is stopped by addition of 1N $H_2SO_4$ solution (50 μL). Cells are then washed with washing buffer and 2% crystal violet solution (50 μL) is applied for 30 min. After washing with washing buffer (3×200 μL), 1% SDS (100 μL) is added to each well and the plates are shaken lightly for 1 hr prior to measuring the absorbance at 595 nm (Varioskan® Flash, Thermo-Fisher Scientific).

The measured $OD_{450-655}$ readings are corrected for cell number by dividing the $OD_{450-655}$ by the $OD_{595}$ readings. The percentage induction for each well is calculated relative to vehicle, and the ratio of induction normalised in comparison with the induction produced by a standard control comprising of N-(4-(4-(3-(3-tert-butyl-1-p-tolyl-1H-pyrazol-5-yl)ureido)naphthalen-1-yloxy)pyridin-2-yl)-2-methoxyacetamide (1 μg/mL) which is defined as 100%.

(n) T Cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at 2×10$^5$ cells per well in 100 μL RPMI/10% FBS on 96 well flat bottomed plate (Corning Costar). 25 μL of test compound are diluted to the appropriate concentration (8× final conc.) in normal medium and added to duplicate wells on the plate to achieve a dose response range of 0.03 ng/mL-250 ng/mL. DMSO is added as a negative control. Plates are allowed to pre-incubate for 2 hours before stimulation with 1 μg/mL anti-CD3 (OKT3; eBioscience). After 72 h, the medium in each well is replaced with 150 μL of fresh medium containing 10 μM BrdU (Roche). After 16 h, the supernatant is removed, the plate is dried and the cells fixed by adding 100 μL of fix/denature solution to each well for 20 min as per the manufacturer's instructions (Roche). Plates are washed once with PBS before addition of the anti-BrdU detection antibody and incubated for 90 mins at room temperature. Plates are then washed gently 3× with the wash buffer supplied and developed by addition of 100 μL of substrate solution. The reaction is stopped by addition of 50 μL of 1 M $H_2SO_4$, and read for absorbance at 450 nm on a plate reader (Varioskan® Flash, ThermoFisher Scientific). The $IC_{50}$ is determined from the dose response curve.

(o) IL-2 and IFNγ Release in CD3/CD28 Stimulated LPMC Cells from IBD Patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments 3-4 mm size. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 μm cell strainer, washed twice, resuspended in RPMI-1640 medium (Sigma-Aldrich) containing 10% fetal calf serum, 100 U/mL penicillin and 100 μg/mL streptomycin, and used for cell culture.

Freshly isolated LPMCs ($2 \times 10^5$ cells/well) are stimulated with 1 μg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

(p) Inhibition of Cytokine Release from Myofibroblasts Isolated from IBD Patients Myofibroblasts from inflamed IBD mucosa are isolated as follows:

The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 μg/mL streptomycin, 50 μg/mL gentamycin, and 1 μg/mL amphotericin (Sigma-Aldrich). Established colonies of myofibroblasts are seeded into 25-cm² culture flasks and cultured in DMEM supplemented with 20% FBS and antibiotics to at least passage 4 to provide a sufficient quantity for use in stimulation experiments.

Subconfluent monolayers of myofibroblasts are then seeded in 12-well plates at $3 \times 10^5$ cells per well are starved in serum-free medium for 24 h at 37° C., 5% $CO_2$ before being cultured for 24 h in the presence of either DMSO control or appropriate concentrations of compound. After 24 h the supernatant is removed and assayed for the presence of IL-8 and IL-6 by R&D ELISA. Percentage inhibition of cytokine release by the test compounds is calculated relative to the cytokine release determined for the DMSO control (100%).

(q) Human Neutrophil Degranulation

Neutrophils are isolated from human peripheral blood as follows:

Blood is collected by venepuncture and anti-coagulated by addition of 1:1 EDTA: sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis-Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+ (Hanks buffered salt solution (without phenol red) containing cytochalasin B (5 μg/mL) and 1 mM $CaCl_2$) to achieve $5 \times 10^6$ cells/mL.

$5 \times 10^4$ cells are added to each well of a V-bottom 96 well plate and incubated (30 mins, 37° C.) with the appropriate concentration of test compound (0.3-1000 ng/mL) or vehicle (DMSO, 0.5% final conc). Degranulation is stimulated by addition of fMLP (final conc 1 μM) which after a further incubation (30 mins, 37° C.) the cells are removed by centrifugation (5 mins, 1500 rpm) and the supernatants transferred to a flat bottom 96 well plate. An equal volume of tetramethylbenzidine (TMB) is added and after 10 mins the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

(r) Cell Cytotoxicity Assay $5 \times 10^4$ TK6 cells (lymphoblastic T cell line) are added to the appropriate number of wells of a 96 well plate in 195 μL of media (RPMI supplemented with 10% foetal bovine serum). 5 μL of DMSO control (final concentration 0.5% v/v) or test compound (final concentration either 5 or 1 μg/mL) is added to the wells and incubated at 37° C., 5% $CO_2$. After 24 hours, the plate is centrifuged at 1300 rpm for 3 minutes and the supernatant discarded. Cells are then resuspended in 7.5 μg/mL propidium iodide (PI) in PBS. After 15 minutes, cells are analysed by flow cytometry (BD accuri). The % viability is calculated as the % of cells that are PI negative in the test wells normalised to the DMSO control.

In Vivo Screening: Pharmacodynamics and Anti-Inflammatory Activity (i) LPS-Induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min. After a further 8 hr the animals are anesthetized, their tracheas cannulated and BALF extracted by infusing and then withdrawing from their lungs 1.0 mL of PBS via the tracheal catheter. Total and differential white cell counts in the BALF samples are measured using a Neubaur haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are shown as mean±S.E.M. (standard error of the mean). The percentage inhibition of neutrophil accumulation is calculated for each treatment relative to vehicle treatment.

(ii) Cigarette Smoke Model

A/J mice (males, 5 weeks old) are exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances are administered intra-nasally (35 µL of solution in 50% DMSO/PBS) once daily for 3 days after the final cigarette smoke exposure. At 12 hr after the last dosing, each of the animals is anesthetized, the trachea cannulated and bronchoalveolar lavage fluid (BALF) is collected. The numbers of alveolar macrophages and neutrophils are determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

(iii) DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with dextran sodium sulphate (DSS). On Day 0 of the study DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study animals are weighed every day and stool observations are made and recorded as a score, based on stool consistency. At the time of sacrifice on Day +6 the large intestine is removed and the length and weight are recorded. Sections of the colon are taken for either MPO analysis to determine neutrophil infiltration or for histopathology scoring to determine disease severity.

(iv) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1 or 5 mg/kg) one day before (Day −1) stimulation of the inflammatory response by treatment with 2,4,6-trinitrobenzenesulphonic acid (TNBS) (15 mg/mL in 50% ethanol/50% saline). On Day 0 of the study TNBS (200 µL) is administered intra-colonically via a plastic catheter with BID dosing of the vehicle, reference or test compound continuing for 2 or 4 days. During the study animals are weighed every day and stool observations are made and recorded as a score, based on stool consistency. At the time of sacrifice on Day 2 (or Day 4) the large intestine is removed and the length and weight recorded. Sections of the colon are taken for histopathology scoring to determine disease severity.

(v) Adoptive Transfer in Mice

On Study day 0, female Balb/C mice are terminated and spleens obtained for CD45RB$^{high}$ cell isolation (Using SCID IBD cell Separation protocol). Approximately 4×10$^5$ cells/mL CD45RB$^{high}$ cells are then injected IP (100 µL/mouse) into female SCID animals. On study day 14, mice are weighed and randomized into treatment groups based on body weight. On Day 14 compounds are administered BID, via oral gavage, in a peanut oil vehicle at the dose levels outlined below and a dose volume of 5 mL/kg. Treatment continues until study day 42, at which point the animals are necropsied 4 hours after am administration. The colon length and weight is recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between nave animals and vehicle animals, where higher inhibition implies closer to the non-diseased, nave, phenotype.

(vi) Endotoxin-Induced Uveitis in Rats

Male, Lewis rats (6-8 weeks old, Charles River UK Limited) are housed in cages of 3 at 19-21° C. with a 12 h light/dark cycle (07:00/19:00) and fed a standard diet of rodent chow and water ad libitum. Non-fasted rats are weighed, individually identified on the tail with a permanent marker and receive a single intravitreal administration into the right vitreous humor (5 µL dose volume) of 100 ng/animal, i.v.t. of LPS (*Escherichia coli* 0111:B4 prepared in PBS, Sigma Aldrich, UK) using a 32-gauge needle. Untreated rats are injected with PBS. Test compound, dexamethasone (Dex) or vehicle (20% hydroxypropyl-β-cyclodextrin, 0.1% HPMC, 0.01% Benzalconium chloride, 0.05% EDTA, 0.7% NaCl in deionised water) are administered by the topical route onto the right eye (10 µL) of animals 30 minutes prior to LPS, at the time of LPS administration, and 1, 2 and 4 hours post LPS administration. Before administration, the solution or suspension to be administered is agitated for 5 minutes to ensure a uniform suspension. 6 hours after LPS dosing, animals are euthanized by overdose with pentobarbitone (i.v.). Following euthanasia, the right eye of each animal is enucleated and dissected into front (anterior) and back (posterior) sections around the lens. Each section is weighed and homogenised in 500 µL of sterile phosphate buffered saline followed by 20 minutes centrifugation at 12000 rpm at 4° C. The resulting supernatant is divided into 3 aliquots and stored at −80° C. until subsequent cytokine analysis by R&D DuoSet ELISA.

Summary of In Vitro and In Vivo Screening Results

TABLE 1

Results from in vitro p38 MAPKα (Method 2), c-Src, Syk and GSK3α (Method 2) inhibition assays

| Test Compound Example No. | IC50 Values for Enzyme Inhibition (nM) | | | |
|---|---|---|---|---|
| | p38 MAPKα | c-Src | Syk | GSK3α |
| 1 | 5 | 5 | 149 | 499 |
| 2 | 10 | 5 | 543 | 5226 |
| 3 | 36 | — | — | 1940 |
| 4 | — | — | — | 1011 |
| 5 | 160 | 10 | >1000 | 7487 |
| 6 | — | — | — | 1229 |
| 7 | 11 | 5 | >1000 | 1847 |
| 8 | 20 | 5 | >1000 | 3074 |
| 9 | 66 | 53 | >1000 | 12384 |
| 10 | 9 | 8 | 819 | 14119 |
| 11 | 13 | 9 | >1000 | 9523 |
| 12 | — | — | — | 13108 |
| 13(a) | — | — | — | 8607 |
| 13(b) | — | — | — | 13108 |

By way of comparison, the p38 MAPKα IC50 values (measured by Method 2) for Reference Compounds A and B were 54 and 139 nM, respectively.

Reference Compounds A and B have the following structures.

Reference Compound A 3-((4-((4-(3-(3-(tert-Butyl)-1-(p-tolyl)-1H-pyrazol-5-yl)ureido)naphthalen-1-yl)oxy)-pyrimidin-2-yl)amino)-5-ethynyl-N-(2-morpholinoethyl)benzamide

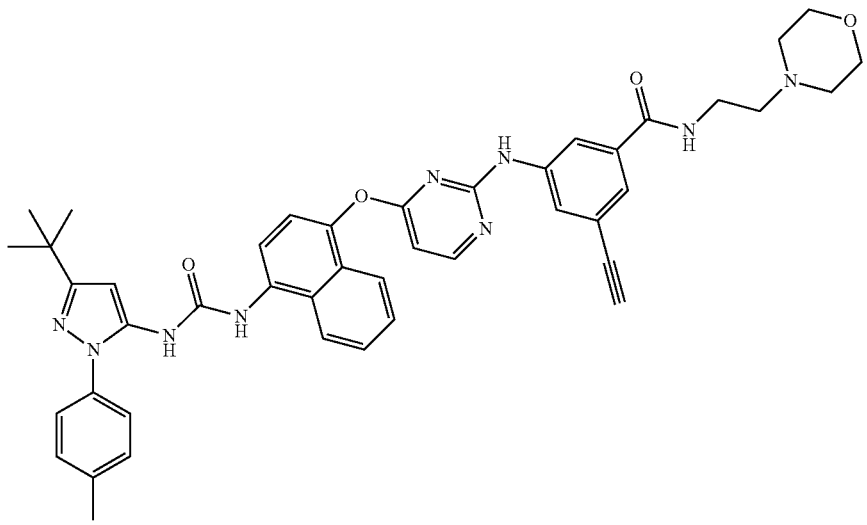 [SMILES: C#Cc1cc(Nc2nccc(Oc3ccc(NC(=O)Nc4cc(C(C)(C)C)nn4-c4ccc(C)cc4)c4ccccc34)n2)cc(C(=O)NCCN2CCOCC2)c1]

Reference Compound B 1-(3-(tert-Butyl)-1-(p-tolyl)-1H-pyrazol-5-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea

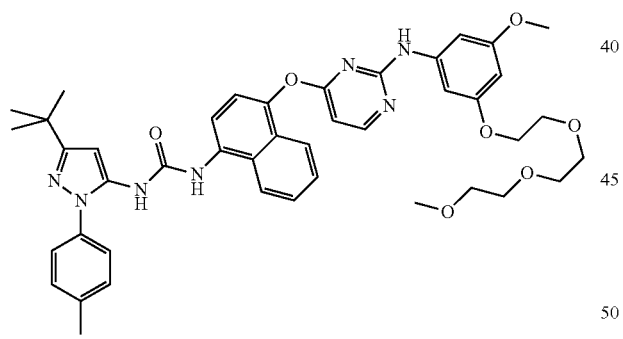

TABLE 2

Inhibition of cytokine release in stimulated cells (the protocols for which are described by assays (a), (b), (c) and (d) above).

| Test Compound Example No. | dU937 cells IL-8 | dU937 cells TNFα | PBMCs IL-8 | PBMCs IL-2 | PBMCs IFNγ | HT29 cells IL-8 |
|---|---|---|---|---|---|---|
| 1 | 6.7 | 2.4 | 1.6 | 17.5 | 4.9 | 33.4 |
| 2 | 1.0 | 2.0 | 3.6 | 11.3 | 6.2 | 16.6 |
| 3 | — | — | 7.2 | — | 22 | — |
| 4 | — | — | 4.7 | — | — | — |
| 5 | — | — | 2.8 | 33.8 | 13.3 | — |

TABLE 2-continued

Inhibition of cytokine release in stimulated cells (the protocols for which are described by assays (a), (b), (c) and (d) above).

| Test Compound Example No. | dU937 cells IL-8 | dU937 cells TNFα | PBMCs IL-8 | PBMCs IL-2 | PBMCs IFNγ | HT29 cells IL-8 |
|---|---|---|---|---|---|---|
| 6 | — | — | 10.7 | — | — | — |
| 7 | — | — | 2.2 | — | 11.8 | — |
| 8 | — | — | 4.8 | — | 13.2 | — |
| 9 | — | — | 3.8 | — | 33.7 | 18.0 |
| 10 | — | — | 15.6 | — | — | 270.4 |
| 11 | — | — | 26.1 | — | — | >1000 |
| 12 | — | — | 546 | — | — | — |
| 13(a) | — | — | 5.4 | — | — | — |
| 13(b) | — | — | 9.3 | — | — | — |

TABLE 3

Effect of compounds of the examples on β-catenin induction (NT = not tested), as determined by assay (m) (values reported are normalised relative to the values for N-(4-(4-(3-(3-tert-butyl-1-p-tolyl-1H-pyrazol-5-yl)ureido)naphthalen-1-yloxy)pyridin-2-yl)-2-methoxyacetamide)

| Test compound | % β-catenin induction Concentration of test compound 1 μg/mL | 5 μg/mL | 10 μg/mL |
|---|---|---|---|
| 1 | −1.5 | 10.5 | NT |
| 2 | −2 | 6.5 | 4.5 |
| 3 | −1 | 25 | 27 |
| 4 | NT | NT | NT |
| 5 | −5.5 | −7 | −2 |
| 6 | NT | NT | NT |
| 7 | 1.5 | 6 | 9.5 |
| 8 | 2.5 | 4 | 3.5 |
| 9 | −2.5 | −1 | 4.5 |
| 10 | NT | NT | NT |

TABLE 3-continued

Effect of compounds of the examples on β-catenin induction (NT = not tested), as determined by assay (m) (values reported are normalised relative to the values for N-(4-(4-(3-(3-tert-butyl-1-p-tolyl-1H-pyrazol-5-yl)ureido)naphthalen-1-yloxy)pyridin-2-yl)-2-methoxyacetamide)

| Test compound | % β-catenin induction Concentration of test compound | | |
|---|---|---|---|
|  | 1 μg/mL | 5 μg/mL | 10 μg/mL |
| 11 | NT | NT | NT |
| 12 | NT | NT | NT |
| 13(a) | NT | NT | NT |
| 13(b) | NT | NT | NT |

As illustrated in Table 4 below, the compounds of Example 1 was also screened in in vivo assay (iv) above, as conducted over 2 days. Histopathology analysis revealed that the compound of Example 1 displayed significant activity in this in vivo model of colonic inflammation. In particular, that compound, when dosed orally at either 1 or 5 mg/kg, demonstrated marked improvements in ulcer grade and epithelial repair compared to the vehicle control. In addition, the compound of Example 1 produced a marked reduction in inflammatory cell infiltrate in the reticular and laminar propria zone.

TABLE 4

Summary of results from studies on TNBS-induced colitis in mice.

| Treatment group | TNBS | | |
|---|---|---|---|
|  | n | Ulcer grade | LP inflammation |
| Non-diseased | 6 | 0.0 ± 0.0 | 0.2 ± 0.2 |
| TNBS + Vehicle | 24 | 4.3 ± 0.2 | 4.7 ± 0.1 |
| Example 1 (1 mg/kg) | 12 | 3.3 ± 0.5 | 4.2 ± 0.2 |
| Example 1 (5 mg/kg) | 12 | 3.2 ± 0.5 | 2.4 ± 0.3 |

As illustrated in Table 5 below, the compound of Example 1 was also screened in cellular assay (I), i.e., the ex-vivo human biopsy model described above, where it demonstrated significant anti-inflammatory effects in biopsies from ulcerative colitis (UC) patients. In contrast to healthy volunteers, intestinal mucosal biopsies from UC patients have been shown to spontaneously release pro-inflammatory cytokines in vitro (Onken, J. E. et al., *J Clin Immunol*, 2008, 126(3): 345-352). Thus, the compounds of Example 1 significantly inhibited cytokine (IL-1β, IL-6 and IL-8) release compared to the DMSO control when incubated, at 1 μg/mL, for 24 hours with biopsies from ulcerative colitis patients.

TABLE 5

Summary of results from assays using intestinal mucosa biopsies from the inflamed regions of the colon of various patients suffering from ulcerative colitis (a form of IBD).

| Treatment group | Cytokine release from biopsies of UC patients | | | | | |
|---|---|---|---|---|---|---|
|  | n | IL-1β release | n | IL-6 release | n | IL-8 release |
| DMSO control |  | 100% |  | 100% |  | 100% |
| Example 1 (1 μg/mL) | 2 | 3 ± 2 | 3 | 8 ± 8 | 3 | 2 ± 2 |

ABBREVIATIONS

AcOH glacial acetic acid
aq aqueous
ATP adenosine-5'-triphosphate
BALF bronchoalveolar lavage fluid
BINAP 2,2'-bis(diphenylphosphino)-1,1'-binaphthyl
BOP (benzotriazol-1-yloxy)tris(dimethylamino)phosphonium hexafluorophosphate
br broad
BSA bovine serum albumin
CatCart® catalytic cartridge
CDI 1,1-carbonyl-diimidazole
COPD chronic obstructive pulmonary disease
d doublet
dba dibenzylideneacetone
DBU 1,8-diazabicyclo[5.4.0]undec-7-ene
DCC dicyclohexylcarbodiimide
DCM dichloromethane
DIAD diisopropyl azodicarboxylate
DIPEA diisopropylethylamine
DMAP 4-dimethylaminopyridine
DMF dimethylformamide
DMSO dimethyl sulfoxide
DPPA diphenylphosphoryl azide
d-U937 cells PMA differentiated U-937 cells
(ES$^+$) electrospray ionization, positive mode
Et ethyl
Et$_3$N triethylamine
EtOAc ethyl acetate
EtOH ethanol
FCS foetal calf serum
FRET fluorescence resonance energy transfer
GSK3α glycogen synthase kinase 3α
HBEC primary human bronchial epithelial cells
HPLC high performance liquid chromatography
hr hour(s)
HATU 2-(1H-7-azabenzotriazol-1-yl)-1,1,3,3-tetramethyl uronium hexafluorophosphate
HOAt 1-hydroxy-7-azabenzotriazole
HOBt hydroxybenzotriazole
HRP horseradish peroxidise
HRV human rhinovirus
ICAM-1 inter-cellular adhesion molecule 1
iPrOAc isopropyl acetate
JNK c-Jun N-terminal kinase
LC liquid chromatography
LPS lipopolysaccharide
(M+H)$^+$ protonated molecular ion
MAPK mitogen-activated protein kinase
MAPKAP-K2 mitogen-activated protein kinase-activated protein kinase-2
mCPBA meta-chloroperbenzoic acid
Me methyl
MeCN acetonitrile
MeOH methanol
MHz megahertz
min minute(s)
MMAD mass median aerodynamic diameter
MOI multiplicity of infection
MTT 3-(4,5-dimethylthiazol-2-yl)-2,5-diphenyltetrazolium bromide
MS mass spectrometry
m/z: mass-to-charge ratio
NMP N-methyl pyrrolidinone
NMR nuclear magnetic resonance (spectroscopy)
PBMC peripheral blood mononuclear cell
PBS phosphate buffered saline
Ph phenyl
PHA phytohaemagglutinin
PMA phorbol myristate acetate p-TsOH 4-methylbenzenesulfonic acid (para-toluenesulfonic acid)
PyBOP (benzotriazol-1-yloxy)tripyrrolidinophosphonium hexafluorophosphate
q quartet
rt room temperature
RP HPLC reverse phase high performance liquid chromatography
RSV respiratory syncytial virus
s singlet
sat saturated
SCX solid supported cation exchange (resin)
SDS sodium dodecyl sulfate
$S_N Ar$ nucleophilic aromatic substitution
t triplet
T3P 1-propanephosphonic acid cyclic anhydride
TBAF tetrabutylammonium fluoride
TBDMS tert-butyldimethylsilyl
$TCID_{50}$ 50% tissue culture infectious dose
TEA triethylamine
THF tetrahydrofuran
TFA trifluoroacetic acid
TMS-Cl trimethylsilyl chloride
TNFα tumor necrosis factor alpha
Prefixes n-, s-, i-, t- and tert- have their usual meanings: normal, secondary, iso, and tertiary.

The invention claimed is:
1. A compound of formula I,

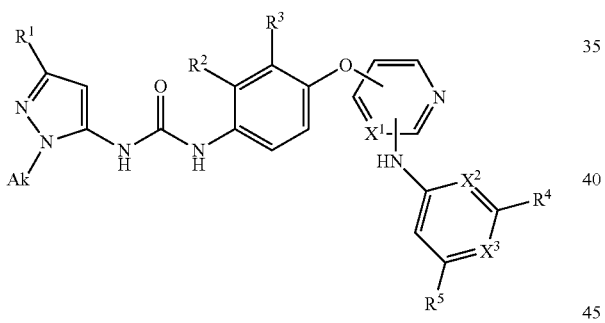

I wherein
Ak represents $C_{1-4}$ alkyl;
$R^1$ represents trimethylsilyl, $C_{2-7}$ alkyl, $C_{2-7}$ alkenyl, $C_{2-7}$ alkynyl, $C_{3-7}$ cycloalkyl, phenyl, $Het^1$ or $Het^2$, which latter seven groups are optionally substituted by one or more substituents selected from the group consisting of $C_{1-2}$ alkyl, halo, hydroxy, and $C_{1-2}$ alkoxy;
$R^2$ and $R^3$, together with the C-atoms to which they are attached, form a fused phenyl or pyridyl ring, which latter two rings are optionally substituted by one or more substituents selected from the group consisting of $C_{1-3}$ alkyl, $C_{1-3}$ haloalkyl, cyano and halo,
or one of $R^2$ and $R^3$ represents H, halo, cyano, $C_{1-3}$ alkyl or $C_{1-3}$ haloalkyl and the other independently represents halo, cyano, $C_{1-3}$ alkyl or $C_{1-3}$ haloalkyl,
or $R^2$ and $R^3$ together combine to form $C_{3-5}$ alkylene or $C_{3-5}$ alkenylene, which latter two groups are optionally substituted by one or more substituents selected from the group consisting of $C_{1-3}$ alkyl, $C_{1-3}$ haloalkyl, cyano and halo;

$X^1$ represents N or CH;
$X^2$ and $X^3$ both represent $CR^Z$ or one of $X^2$ and $X^3$ represents N and the other represents $CR^Z$;
$R^Z$ represents H, halo, cyano, $C_{1-3}$ alkyl or $C_{1-3}$ alkoxy, which latter two groups are optionally substituted by one or more halo atoms;
$R^4$ represents
-$Q^1$-[$CH_2(CH_2)_{0-1}CH_2$—O]$_{1-12}$—$CH_2(CH_2)_{0-1}CH_2$—$R^{6a}$,
-$Q^2$-C($R^{6c}$)($R^{6d}$)—[$C_{1-5}$ alkylene]-$R^{6a}$ or
—S(O)$_n R^{6b}$;
$R^5$ represents $C_{1-3}$ alkoxy or $C_{1-3}$ alkyl, which latter two groups are optionally substituted by one or more halo atoms, or $R^5$ represents H, cyano, halo or $C_{2-3}$ alkynyl;
$R^{6a}$ represents $OR^{7a}$ or $N(R^{7b})R^{7c}$;
$R^{6b}$ represents $C_{1-8}$ alkyl, $C_{3-8}$ cycloalkyl, phenyl, $Het^1$ or $Het^2$, which latter five groups are optionally substituted by one or more substituents selected from the group consisting of halo, hydroxyl, $C_{1-3}$ alkyl and $C_{1-3}$ alkoxy;
$R^{6c}$ and $R^{6d}$ independently represent H or methyl;
$R^{7a}$ to $R^{7c}$ independently represent H or $C_{1-4}$ alkyl optionally substituted by one or more halo atoms, or $R^{7b}$ and $R^{7c}$, together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from the group consisting of halo, hydroxy, oxo, $C_{1-4}$ alkyl and $C_{1-4}$ alkoxy;
$Q^1$ and $Q^2$ independently represent C(O)NH, O or S(O)$_p$;
n and p independently represent 0, 1 or 2,
$Het^1$ represents 5- or 6-membered heterocyclic group that is fully aromatic, which group contains one or more heteroatoms selected from the group consisting of N, O and S; and
$Het^2$ represents a 4- to 7-membered heterocyclic group that is fully saturated or partially unsaturated, which group contains one or more heteroatoms selected from the group consisting of N, O and S;
or a pharmaceutically acceptable salt, solvate or isotopic derivative thereof.

2. A compound as claimed in claim 1, that is a compound of formula Ia, Ib or Ic

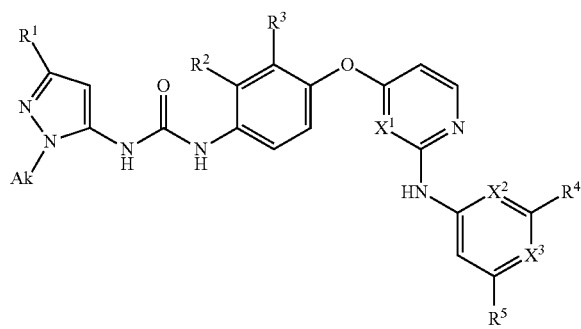

Ia

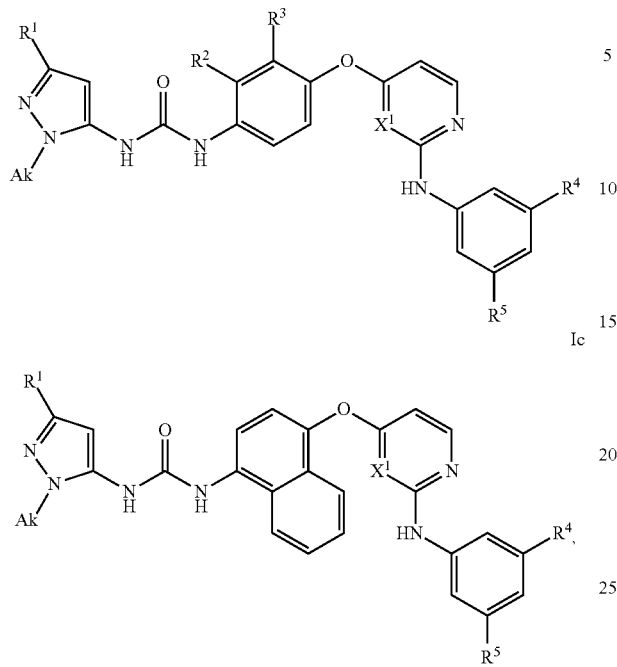

or a pharmaceutically acceptable salt, solvate or isotopic derivative thereof, wherein $R^1$ to $R^5$, Ak and $X^1$ to $X^3$ are as defined in claim 1.

3. A compound as claimed in claim 1, wherein Ak represents $C_{1-3}$ alkyl.

4. A compound as claimed in claim 1, wherein $R^1$ represents trimethylsilyl, $C_{3-5}$ n-alkyl, $C_{4-7}$ branched alkyl, $C(C_{1-2}$ alkyl$)_2$-C≡CH, or $C_{3-5}$ cycloalkyl, which latter group is optionally substituted by $C_{1-2}$ alkyl.

5. A compound as claimed in claim 1, wherein $R^2$ and $R^3$, together with the C-atoms to which they are attached, form a fused phenyl ring, or $R^2$ and $R^3$ independently represent halo or $C_{1-2}$ alkyl.

6. A compound as claimed in claim 1, wherein $X^2$ and $X^3$ both represent CH or one of $X^2$ represents CH and $X^3$ represents N or $CR^Z$, wherein $R^Z$ represents halo.

7. A compound as claimed in claim 1, wherein:
$R^4$ represents
-$Q^1$-[$CH_2CH_2$—O]$_{1-8}$—$CH_2CH_2$—$R^{6a}$,
-$Q^2$-$CH_2$—[$C_{1-2}$ alkylene]-$R^{6a}$ or
—$S(O)_n R^{6b}$; and
n represents 0 or 2.

8. A compound as claimed in claim 1, wherein $R^5$ represents H, cyano, chloro, fluoro, $C_{2-3}$ alkynyl, $C_{1-2}$ alkyl or $C_{1-2}$ alkoxy, which latter two groups are optionally substituted by one or more fluoro atoms.

9. A compound as claimed in claim 1, wherein:
$R^{6a}$ represents OH, O—$C_{1-2}$ alkyl or $N(R^{7b})R^{7c}$; or
$R^{6b}$ represents $C_{1-5}$ alkyl or $C_{3-5}$ cycloalkyl.

10. A compound as claimed in claim 1, wherein $R^{7b}$ and $R^{7c}$ independently represent H or methyl, or $R^{7b}$ and $R^{7c}$, together with the N-atom to which they are attached, form a 4- to 7-membered heterocyclic group that is fully saturated, which heterocyclic group contains one N atom (the atom to which $R^{7b}$ and $R^{7c}$ are attached) and, optionally, one further heteroatom selected from the group consisting of O, S and N, and which heterocyclic group is optionally substituted by one or more $C_{1-2}$ alkyl groups.

11. A compound as claimed in claim 1, wherein $Q^1$ and $Q^2$ independently represent C(O)NH or O.

12. A compound as claimed in claim 1, wherein:
Ak represents methyl;
$R^1$ represents tert-butyl;
$X^1$ represents N;
$R^4$ represents
-$Q^1$-[$CH_2CH_2$—O]$_{2-6}$—$CH_2CH_2$—$OCH_3$,
—C(O)NH—$CH_2$—$CH_2$—$N(R^{7b})R^{7c}$ or
—$S(O)_2$-cyclopropyl;
$R^5$ represents —C≡CH or methoxy;
$R^{6a}$ represents O—$CH_3$ or $N(R^{7b})R^{7c}$;
$R^{7b}$ and $R^{7c}$ both represent methyl, or $R^{7b}$ and $R^{7c}$, together with the N-atom to which they are attached, form a piperazinyl group optionally substituted by methyl or a morpholinyl group; and/or
$Q^1$ represents C(O)NH or O.

13. A compound as claimed in claim 1 which is a compound selected from the group consisting of:
3-((4-((4-(3-(3-(tert-butyl)-1-methyl-1H-pyrazol-5-yl)ureido)naphthalen-1-yl)oxy)pyrimidin-2-yl)amino)-5-ethynyl-N-(2-morpholinoethyl)benzamide;
1-(3-(tert-butyl)-1-methyl-1H-pyrazol-5-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea;
1-(3-(tert-butyl)-1-methyl-1H-pyrazol-5-yl)-3-(4-((2-((3-(cyclopropylsulfonyl)-5-methoxy-phenyl)amino)pyrimidin-4-yl)oxy)naphthalen-1-yl)urea;
3-((4-((4-(3-(3-(tert-butyl)-1-methyl-1H-pyrazol-5-yl)ureido)naphthalen-1-yl)oxy)pyrimidin-2-yl)amino)-5-ethynyl-N-(2-(2-methoxyethoxy)ethyl);
1-(3-(tert-butyl)-1-methyl-1H-pyrazol-5-yl)-3-(4-((2-((3-methoxy-5-(2-(2-(2-methoxy-ethoxy)ethoxy)ethoxy)phenyl)amino)pyridin-4-yl)oxy)naphthalen-1-yl);
1-(4-((2-((3-(2,5,8,11,14,17,20-heptaoxadocosan-22-yloxy)-5-methoxyphenyl)amino)-pyrimidin-4-yl)oxy)naphthalen-1-yl)-3-(3-(tert-butyl)-1-methyl-1H-pyrazol-5-yl)urea,
3-((4-((4-(3-(3-(tert-butyl)-1-methyl-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide;
3-((4-((4-(3-(3-(tert-butyl)-1-ethyl-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide;
3-((4-((4-(3-(3-(tert-butyl)-1-methyl-1H-pyrazol-5-yl)ureido)naphthalen-1-yl)oxy)pyridin-2-yl)amino)-5-ethynyl-N-(2-(2-(2-methoxyethoxy)ethoxy)ethyl)benzamide;
3-ethynyl-5-((4-((4-(3-(3-isopropyl-1-methyl-1H-pyrazol-5-yl)ureido)naphthalen-1-yl)oxy)pyrimidin-2-yl)amino)-N-(2-morpholinoethyl)benzamide;
3-ethynyl-5-((4-((4-(3-(3-isopropyl-1-methyl-1H-pyrazol-5-yl)ureido)naphthalen-1-yl)oxy)pyrimidin-2-yl)amino)-N-(2-(2-(2-methoxyethoxy)ethoxy)ethyl)benzamide;
3-((4-((4-(3-(1,3-di-tert-butyl-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide;
3-((4-((4-(3-(3-(tert-butyl)-1-isopropyl-1H-pyrazol-5-yl)ureido)naphthalen-1-yl)oxy)pyrimidin-2-yl)amino)-5-ethynyl-N-(2-(2-(2-methoxyethoxy)ethoxy)ethyl)-benzamide; and 3-((4-((4-(3-(3-(tert-butyl)-1-propyl-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide, and a pharmaceutically acceptable salt, solvate or isotopic derivative thereof.

14. A pharmaceutical formulation comprising a compound as defined in claim 1, or pharmaceutically acceptable salt, solvate or isotopic derivative thereof, in admixture with a pharmaceutically acceptable adjuvant, diluent or carrier.

15. A combination product comprising
(A) a compound as defined in claim 1, or pharmaceutically acceptable salt, solvate or isotopic derivative thereof, and
(B) another therapeutic agent,
wherein each of components (A) and (B) is formulated in admixture with a pharmaceutically-acceptable adjuvant, diluent or carrier.

16. A method of treating inflammation, ulcerative colitis, uveitis, posterior uveitis, anterior uveitis, pan uveitis, asthma, pediatric asthma or COPD in a subject in need thereof comprising administering to said subject a compound as defined in claim 1 or a pharmaceutically acceptable salt, solvate or isotopic derivative thereof, wherein the inflammation is a component or symptom of a disease selected from the group consisting of cystic fibrosis, pulmonary hypertension, lung sarcoidosis, idiopathic pulmonary fibrosis, COPD, chronic bronchitis, emphysema, asthma, pediatric asthma, atopic dermatitis, allergic dermatitis, contact dermatitis or psoriasis, allergic rhinitis, rhinitis, sinusitis, conjunctivitis, allergic conjunctivitis, keratoconjunctivitis sicca (dry eye), glaucoma, diabetic retinopathy, macular edema, diabetic macular edema, central retinal vein occlusion (CRVO), dry and/or wet age related macular degeneration (AMD), post-operative cataract inflammation, uveitis, posterior uveitis, anterior uveitis pan uveitis, corneal graft and limbal cell transplant rejection, gluten sensitive enteropathy (coeliac disease), eosinophilic esophagitis, intestinal graft versus host disease, Crohn's disease and ulcerative colitis.

17. The method according to claim 16, wherein the inflammatory disease is uveitis, Crohn's disease or ulcerative colitis.

18. The method according to claim 16, wherein the inflammatory disease is asthma or COPD.

19. A process for the preparation of a compound of formula I which process comprises:
(a) reacting a compound of formula II,

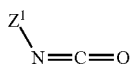

with a compound of formula III,

wherein one of $Z^1$ and $Z^2$ is a structural fragment of formula IV

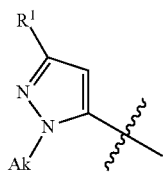

and the other of $Z^1$ and $Z^2$ is a structural fragment of formula V

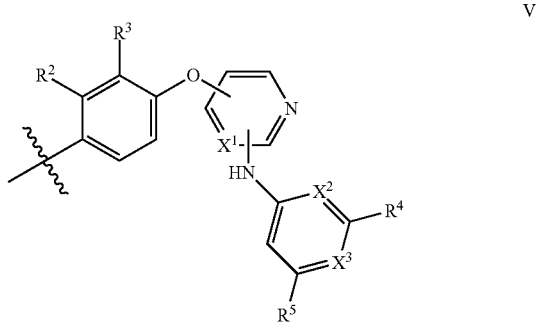

where $R^1$ to $R^5$, Ak and $X^1$ to $X^3$ are as defined in claim 1;
(b) reacting a compound of formula IIa,

wherein $Z^1$ is as defined above, with a suitable azide-forming agent,
which reaction is followed, without isolation, by thermal rearrangement of the intermediate acyl azide (of formula $Z^1$—C(O)—$N_3$) to provide, in situ, a compound of formula II, which compound is then reacted with a compound of formula III as defined above;
(c) reacting a compound of formula IIb,

wherein $LG^1$ represents a leaving group and $Z^1$ is as defined above, with a compound of formula III, as defined above;
(d) reacting a compound of formula VI,

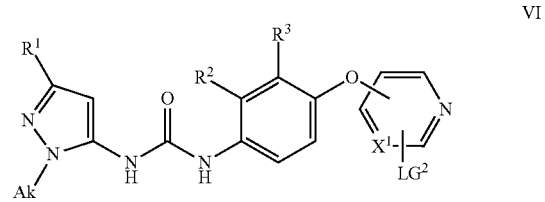

wherein $LG^2$ represents a leaving group and $R^1$ to $R^3$, Ak and $X^1$ are as defined in claim 1, with a compound of formula VII, reacting a compound of formula VIIa,

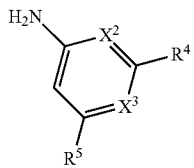

VII

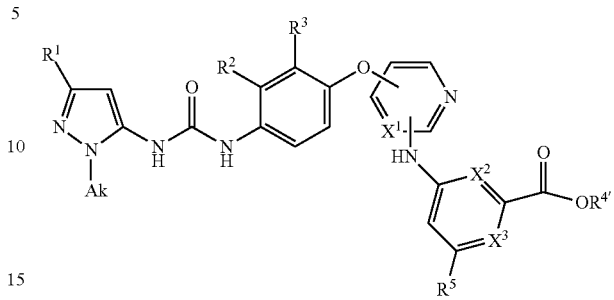

VIIa wherein $R^4$, $R^5$, $X^2$ and $X^3$ are as defined in claim 1;

(e) for compounds of formula I in which $R^4$ represents
—$S(O)_{1-2}$—$[CH_2(CH_2)_{0-1}CH_2$—$O]_{1-12}$—$CH_2(CH_2)_{0-1}CH_2$—$R^{6a}$,
—$S(O)_{1-2}$—$CH_2$—$[C_{1-5}$ alkylene]-$R^{6a}$,
—$S(O)_{1-2}R^{6b}$, oxidizing a corresponding compound of formula I in which, respectively, $R^4$ represents
—$S$—$[CH_2(CH_2)_{0-1}CH_2$—$O]_{1-12}$—$CH_2(CH_2)_{0-1}CH_2$—$R^{6a}$,
—$S$—$CH_2$—$[C_{1-5}$ alkylene]-$R^{6a}$,
—$S$—$R^{6b}$,
wherein $R^{6a}$ to $R^{6d}$ are as defined in claim 1;

(f) for compounds of formula I in which $R^4$ represents
—$C(O)NH$—$[CH_2(CH_2)_{0-1}CH_2$—$O]_{1-12}$—$CH_2(CH_2)_{0-1}CH_2$—$R^{6a}$ or
—$C(O)NH$—$C(R^{6c})(R^{6d})$—$[C_{1-5}$ alkylene]-$R^{6a}$, wherein $R^{4'}$ represents H or a $C_{1-3}$ alkyl group and Ak, $R^1$ to $R^3$, $R^5$ and $X^1$ to $X^3$ are as defined in claim 1, with a compound of formula VIIb or VIIc,

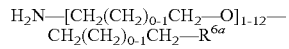 VIIb

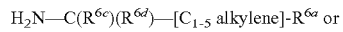 VIIc wherein $R^{6a}$, $R^{6c}$ and $R^{6d}$ are as defined in claim 1; or (g) deprotecting a protected derivative of a compound of formula I, wherein the protected derivative bears a protecting group on an O- or N-atom of the compound of formula I.

\* \* \* \* \*